US008234080B2

(12) United States Patent
Skordalakes

(10) Patent No.: US 8,234,080 B2
(45) Date of Patent: Jul. 31, 2012

(54) METHOD FOR IDENTIFYING A COMPOUND THAT MODULATES TELOMERASE ACTIVITY

(75) Inventor: Emmanuel Skordalakes, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 109 days.

(21) Appl. No.: 12/701,801

(22) Filed: Feb. 8, 2010

(65) Prior Publication Data
US 2010/0216150 A1   Aug. 26, 2010

Related U.S. Application Data

(63) Continuation-in-part of application No. PCT/US2008/080604, filed on Oct. 21, 2008.

(60) Provisional application No. 61/090,726, filed on Aug. 21, 2008, provisional application No. 60/981,548, filed on Oct. 22, 2007.

(51) Int. Cl.
*G01N 33/48* (2006.01)
*G01N 31/00* (2006.01)

(52) U.S. Cl. .......................... 702/27; 702/19

(58) Field of Classification Search .................. None
See application file for complete search history.

(56) References Cited

U.S. PATENT DOCUMENTS

| 5,645,986 | A | 7/1997 | West et al. | 435/6 |
|---|---|---|---|---|
| 5,804,380 | A | 9/1998 | Harley et al. | 435/6 |
| 5,856,096 | A | 1/1999 | Windle et al. | 435/6 |
| 6,342,358 | B1 | 1/2002 | Collins et al. | 435/6 |
| 6,358,687 | B1 | 3/2002 | Chabot et al. | 435/6 |
| 6,517,834 | B1 | 2/2003 | Weinrich et al. | 424/94.5 |
| 6,623,930 | B2 | 9/2003 | Kerwin et al. | 435/6 |
| 6,638,789 | B1 | 10/2003 | Glenn et al. | 438/109 |
| 6,787,133 | B2 | 9/2004 | Weinrich et al. | 424/94.5 |
| 6,906,237 | B2 | 6/2005 | Herron | 800/8 |
| 7,067,283 | B2 | 6/2006 | Weinrich et al. | 435/69.2 |
| 2006/0040307 | A1 | 2/2006 | Cech et al. | 435/6 |

OTHER PUBLICATIONS

Autexier, C. and Lue, N.F. "The Structure and Function of Telomerase Reverse Transcriptase" Annual Review of Biochemistry 2006 vol. 75: 493-517.
Lee et al. "Human Telomerase Reverse Transcriptase Motifs Required for Elongation of a Telomeric Substrate" The Journal of Biological Chemistry 2003 vol. 278(52): 52531-52536.
Peng et al. "Analysis of Telomerase Processivity: Mechanistic Similarity to HIV-1 Reverse Transcriptase and Role in Telomere Maintenance" Molecular Cell 2001 vol. 7: 1201-1211.
Collins, K. and Ghandi, L. "The Reverse Transcriptase Component of the Tetrahymena Telomerase Ribonucleoprotein Complex" Proceedings of the National Academy of Science USA 1998 vol. 95: 8485-8490.
Bryan et al. "Telomerase Reverse Transcriptase Genes Identified in *Tetrahymena Thermophila* and *Oxytricha Trifallax*" Proceedings of the National Academy of Science USA 1998 vol. 95: 8479-8484.
Jacobs et al. "Soluble Domains of Telomerase Reverse Transcriptase Indentified by High-Throughput Screening" Protein Science 2005 vol. 14: 2051-2058.
Friedman, K.L. and Cech, T.R. "Essential Functions of Amino-Terminal Domains in the Yeast Telomerase Catalytic Subunit Revealed by Selection for Viable Mutants" Genes & Development 1999 vol. 13: 2863-2874.
Friedman et al. "N-Terminal Domain of Yeast Telomerase Reverse Transcriptase: Recruitment of Est3p to the Telomerase Complex" Molecular Biology of the Cell 2003 vol. 14: 1-13.
Hammond et al. "The Anchor Site of Telomerase from *Euplotes aediculatus* Revealed by Photo-Cross-Linking to Single- and Double-Stranded DNA Primers" Molecular and Cellular Biology 1997 vol. 17(1): 296-308.
Jacobs et al. "Crystal Structure of the Essential N-Terminal Domain of Telomerase Reverse Transcriptase" Nature Structural and Molecular Biology 2006 vol. 13(3): 218-225.
Wyatt et al. "Characterization of Physical and Functional Anchor Site Interactions in Human Telomerase" Molecular & Cellular Biology 2007 vol. 27(8): 3226-3240.
Lai et al. "RNA Binding Domain of Telomerase Reverse Transcriptase" Molecular and Cellular Biology 2001 vol. 21(4): 990-1000.
Bryan et al. "Telomerase RNA Bound by Protein Motifs Specific to Telomerase Reverse Transcriptase" Molecular Cell 2000 vol. 6: 493-499.
Cunningham, D.D. and Collins, K. "Biological and Biochemical Functions of RNA in the *Tetrahymena* Telomerase Holoenzyme" Molecular and Cellular Biology 2005 vol. 25(11): 4442-4454.
Lai et al. "Template Boundary Definition in *Tetrahymena* Telomerase" Genes & Development 2002 vol. 16: 415-420.
Miller, M.C. and Collins, K. "Telomerase Recognizes its Template by Using an Adjacent RNA Motif" Proceedings of the National Academy of Science USA 2002 vol. 99(10): 6585-6590.
O'Connor et al. "Two Purified Domains of Telomerase Reverse Transcriptase Reconstitute Sequence-Specific Interactions with RNA" The Journal of Biological Chemistry 2005 vol. 280(17): 17533-17539.
Lai et al. "Roles for RNA in Telomerase Nucleotide and Repeat Addition Processivity" Molecular Cell 2003 vol. 11: 1673-1683.
Greider, C.W. and Blackburn, E.H. "A Telomeric Sequence in the RNA of *Tetrahymena* Telomerase Required for Telomere Repeat Synthesis" Nature 1989 vol. 337: 331-337.
Zappulla, D.C. and Cech, T.R. "Yeast Telomerase RNA: A Flexible Scaffold for Protein Subunits" Proceedings of the National Academy of Science USA 2004 vol. 101(27): 10024-10029.
Chen et al. "Secondary Structure of Vertebrate Telomerase RNA" Cell 2000 vol. 100: 503-514. Ly et al. "Comprehensive Structure-Function Analysis of the Core Domain of Human Telomerase RNA" Molecular and Cellular Biology 2003 vol. 23(19): 6849-6856.

(Continued)

*Primary Examiner* — Michael Borin
(74) *Attorney, Agent, or Firm* — Licata & Tyrrell P.C.

(57) ABSTRACT

The present invention embraces methods for identifying compounds that modulate the activity of telomerase. Compounds of the invention are identified by designing or screening for a compound which binds to at least one amino acid residue of the TRBD, "thumb," "finger," and/or "palm" domain; or FP-pocket, PT-pocket or Th-pocket of telomerase and testing the compound for its ability to modulate the activity of telomerase.

1 Claim, 9 Drawing Sheets

OTHER PUBLICATIONS

Chen, J. and Greider, C.W. "Template Boundary Definition in Mammalian Telomerase" Genes & Development 2003 vol. 17: 2747-2752.
Chen, J. and Greider, C.W. "Telomerase RNA Structure and Function: Implications for Dyskeratosis Congenita" Trends in Biochemical Sciences 2004 vol. 29(4): 183-192.
Theimer, C.A. and Feigon, J. "Structure and Function of Telomerase RNA" Current Opinion in Structural Biology 2006 vol. 16 : 307-318.
Licht, J.D. and Collins, K. "Telomerase RNA Function in Recombinant *Tetrahymena* Telomerase" Genes & Development 1999 vol. 13: 1116-1125.
Aisner et al. "Telomerase Regulation: Not Just Flipping the Switch" Current Opinion in Genetics & Development 2002 vol. 12: 80-85.
Cong et al. "Human Telomerase and Its Regulation" Microbiology and Molecular Biology Reviews 2002 vol. 66(3): 407-425.
Dong et al. "Telomerase: Regulation, Function and Transformation" Critical Reviews in Oncology/Hematology 2005 vol. 54: 85-93.
Loayza, D. and de Lange, T. "Telomerase Regulation at the Telomere: A Binary Switch" Cell 2004 vol. 117: 279-280.
Smogorzewska, A. and de Lange, T. "Regulation of Telomerase by Telomeric Proteins" Annual Review of Biochemistry 2004 vol. 73: 177-208.
Smogorzewska et al. "Control of Human Telomere Length by TRF1 and TRF2" Molecular and Cellular Biology 2000 vol. 20(5): 1659-1668.
Witkin, K.L. and Collins, K. "Holoenzyme Proteins Required for the Physiological Assembly and Activity of Telomerase" Genes & Development 2004 vol. 18: 1107-1118.
Witkin et al. "Positive and Negative Regulation of *Tetrahymena* Telomerase Holoenzyme" Molecular and Cellular Biology 2007 vol. 27(6): 2074-2083.
Aigner, S. and Cech, T.R. "The *Euplotes* Telomerase Subunit p43 Stimulates Enzymatic Activity and Processivity in Vitro" RNA 2004 vol. 10(7): 1108-1118.
Aigner et al. "The *Euplotes* La Motif Protein p43 Has Properties of a Telomerase-Specific Subunit" Biochemistry 2003 vol. 42(19): 5736-5747.
O'Connor, C.M. and Collins, K. "A Novel RNA Binding Domain in *Tetrahymena* Telomerase p65 Initiates Hierarchical Assembly of Telomerase Holoenzyme" Molecular and Cellular Biology 2006 vol. 26(6): 2029-2036.
Prathapam et al. "A Telomerase Holoenzyme Protein Enhances Telomerase RNA Assembly with Telomerase Reverse Transcriptase" Nature Structural & Molecular Biology 2005 vol. 12(3): 252-257.
Evans, S.K. and Lundblad, V. "The Est1 Subunit of *Saccharomyces cerevisiae* Telomerase Makes Multiple Contributions to Telomere Length Maintenance" Genetics 2002 vol. 162: 1101-1115.
Hughes et al. "The Role of the *EST* Genes in Yeast Telomere Replication" Ciba Foundation Symposium 1997 vol. 211: 41-52.
Lundblad, V. "Telomere Replication: An Est Fest" Current Biology 2003 vol. 13: R439-R441.
Lundblad, V. and Blackburn, E.H. "RNA-Dependent Polymerase Motifs in EST1: Tentative Identification of a Protein Component of an Essential Yeast Telomerase" Cell 1990 vol. 60: 529-530.
Reichenbach et al. "A Human Homolog of Yeast Est1 Associates with Telomerase and Uncaps Chromosome Ends When Overexpressed" Current Biology 2003 vol. 13: 568-574.
Snow et al. "Functional Conservation of the Telomerase Protein Est1p in Humans" Current Biology 2003 vol. 13: 698-704.
Chandra et al. "Cdc13 Both Positively and Negatively Regulates Telomere Replication" Genes & Development 2001 vol. 15: 404-414.
Evans, S.K. and Lundblad, V. "Est1 and Cdc13 as Comediators of Telomerase Access" Science 1999 vol. 286: 117-120.
Lustig, A.J. "Cdc13 Subcomplexes Regulate Multiple Telomere Functions" Nature Structural Biology 2001 vol. 8(4): 297-299.
Pennock et al. "Cdc13 Delivers Separate Complexes to the Telomere for End Protection and Replication" Cell 2001 vol. 104: 387-396.
Bosoy et al. "Conserved N-Terminal Motifs of Telomerase Reverse Transcriptase Required for Ribonucleoprotein Assembly in Vivo" The Journal of Biological Chemistry 2003 vol. 278(6): 3882-3890.
Xia et al. "Identification of Functionally Important Domains in the N-Terminal Region of Telomerase Reverse Transcriptase" Molecular and Cellular Biology 2000 vol. 20(14): 5196-5207.
Bosoy, D. and Lue, N. F. "Functional Analysis of Conserved Residues in the Putative 'Finger' Domain of Telomerase Reverse Transcriptase" The Journal of Biological Chemistry 2001 vol. 276(49): 46305-46312.
Haering et al. "Analysis of Telomerase Catalytic Subunit Mutants in Vivo and in Vitro in *Schizosaccharomyces pombe*" Proceedings of the National Academy of Science USA 2000 vol. 97(12): 6367-6372.
Hossain et al. "Function Analysis of the C-Terminal Extension of Telomerase Reverse Transcriptase" The Journal of Biological Chemistry 2002 vol. 277(39): 36174-36180.
Lue et al. "A Conserved Telomerase Motif within the Catalytic Domain of Telomerase Reverse Transcriptase Is Specifically Required for Repeat Addition Processivity" Molecular and Cellular Biology 2003 vol. 23(23): 8440-8449.

```
                          β1     α1
                         ──▶   ──○──
TRICA   ----------------MVHYYRLSLKSRQKAP--------------------------      16
MOUSE   FLYSRGDGQERLNPSFLLSNLQPNLTGARRLVEIIFLGSRPRTSGPLCRTHRLSRR----    390
HUMAN   FLYSSGD-KEQLRPSFLLSSLRPSLTGARRLVETIFLGSRPWMPGTPRRLPRLPQR----    385
ARATH   FKFGLSETYSVIPPNHILKTLRPNCSDSKLLMNHIFGEVNVWSTTPSHGKGNCPSGSICL    369
YEAST   FLHKLNINSSSFFPYSKILPSSSSIKKLTDLREAIFPTNLVKIPQRLKVR----------    236
SCHPO   FKQDLYFNLHSICDRNTVHMWLQWIFPRQFGLINAFQVKQLHKVIPLVSQSTVVPKR---    294
TETTH   VFKSSFFNYSEIKKGFQFKVIQEKLQGRQFINSDKIKPDHPQTIIKKTLLKEYQSKNFSC    300
EUPAE   FYCTHFNRNNQFFKKHEFVSNKNNISAMDRAQTIFTNIFRFNRIRKKLKDK---------    292

α2
                      ──────────────────────
TRICA   ---KIVNSKYNSILNIALKNFRLCKKIKTKKPV---------------------------     46
MOUSE   ---YWQMRPLFQQLLVNHAECQYVRLIRSHCR--------FRTANQQVT-----------    428
HUMAN   ---YWQMRPLFLELLGNHAQCPYGVLIKTHCP--------LRAAVTPAAGVCAREKPQGS    434
ARATH   ---YHSLLKSLKNLIGKTKSSHLKMLIDKHCPVLLQEDALKSGTTSQSSRRQKADKLPH    426
YEAST   ------INLTLQKLLKRHKRLNYVSIINSICP----------------------------    262
SCHPO   ---LLKVYPLIEQTAKRLHRISLSKVYNHYCP----------------------------    323
TETTH   QEERDLFLEFTEKIVQNFHNINFNYLIKKFCKLP-----------ENYQSLKSQVKQIVQ    349
EUPAE   ------VIEKIAYMLEKVKDFNFNYYITKSCPLP-----------ENWRERKQKIE    331
                                   MOTIF CP

α3        α4        α5
                                 ──○──     ──○── ──────○──────
TRICA   -------------------------QILALLQEII----PKSYFGTTTNLKRFYKVVEKI     77
MOUSE   ----DALNTSPPHLMDLLRLHSSPWQVYGFLRACLCKVVSASLWGTRHNERRFFKRNLKKF    484
HUMAN   VAAPEEEDTDPRRLVQLLRQHSSPWQVYGFVRACLRRLVPPGLWGSRHNERRFLRNTKKF    494
ARATH   GSSSSQTGKPKCPSVEERKLYCTNDQVVSFIWAICRYIVPESLLGTTHQMRVLRKNIAWF    486
YEAST   -------PLEGTVLDLSHLSRQSPKERVLKFIIVILQKLLPQEMFGSKKNKGKIIKNLNLL    316
SCHPO   -------YIDTHDDEKILSYSLKPNQVFAFLRSILVRVFPKLIWGNQRIFEIILKDLETF    376
TETTH   SENKANQQSCENLFNSLYDTEISYKQITNFLRQIIQNCVPNQLLG-KKNFKVFLEKYEF    408
EUPAE   NLINKTREEKSKYYEELFSYTTDNKCVTQFINEFFYNILPKDFLTGRNRKN-FQKKVKKY    390

β2 α6  α7                                    α8
          ──▶──○──○──                                ──────○──────
TRICA   LTQSSFECIHLSVLHKCYDYDAIPWLQN----------------VEPNLRPKLLLKHNLFL    122
MOUSE   ISLGKYGKLSLQELMWKMKVEDCHWLRS------SPGKDRVPAAEHRLRERILATFLFWL    538
HUMAN   ISLGKHAKLSLQELTWKMSVRDCAWLRR------SPGVGCVRAAEHRLREEILAKFLHWL    548
ARATH   VSRRRNEKCTVNQFLHKVKPSDFPFFARKELCCMVNGHELQSESIRSTQQMLCTKWISWL    546
YEAST   LSLPLNGYLPFDSLLKKLRLKDFRWLFIS--------DIWFTKHNFENLNQLAICFISWL    368
SCHPO   LKLSRYESFSLHYLMSNIKISEIEWLVLG-----KRSNAKMCLSDFEKRKQIFAEFIYWL    431
TETTH   VQMKRFENQKVLDYICFMDVFDVEWFVDLK-----NQKFTQKRKYISDKRKILGDLIVFI    463
EUPAE   VELNKHELIHKNLLLEKINTREISWMQVET-------SAKHFYYFDHENIYVLWKLLRWI    443

β3        β4         α9
          ──────▶───────▶──○──────────────
TRICA   LDNIVKPIIA-FYYKPIKTLNGHEIKFIRKEEYISFESKVFHKLKKMKYLVEVQDEVK-    179
MOUSE   MDTYVVQLLRSFFYITESTFQKNRLFFYRKSVWSKLQSIGVRQHLERVRLRELSQEEVRH    598
HUMAN   MSVYVVELLRSFFYVTETTFQKNRLFFYRKSVWSKLQSIGIRQHLKRVQLRELSEAEVRQ    608
ARATH   FLEIVKKLVHFNFYATESQGGRLNIYYYRKEVWTRLISKEISKALDGYVLVDDAEAESSR    606
YEAST   FRQLIPKIIQTFFYCTEIS-STVTIVYFRHDTWNKLITPFIVEYFKTYLVENNVCRN--H    425
SCHPO   YNSFIIPILQSFFYITESSDLRNRTVYFRKDIWKLLCRPFITS--MKMEAFEKINENNVR    489
TETTH   INKIVIPVLRYNFYITEKHKEGSQIFYYRKPIWKLVSKLTIVKLEEENLEKVEEKLIP--    521
EUPAE   FEDLVVSLIRCFFYVTEQQKSYSKTYYYRKNIWDVIMKMSIADLKKETLAEVQEKEVEEW    503
                                MOTIF T

β5        β6                                α10
          ──────▶───────▶                          ──────○──────
TRICA   --------PRGVLNIIPKQDNFRAIVSIFPDSAR-------------KPFFKLL    212
MOUSE   HQDTWLAMPICRLRFIPKPNGLRPIVNMSYSMGTRALGRRKQAQHFTQRLKTLFSMLNYE    658
HUMAN   HREARPALLTSRLRFIPKPDGLRPIVNMDYVVGARTFRREKRAERLTSRVKALFSVLNYE    668
ARATH   KK------LSKFRFLPKANGVRMVLDFSSSSRQSLR----------DTHAVIKDI    646
YEAST   NSYTLSNFNHSKMRIIPKKSNNEFRILAIPCRGADEEEFTIYKENHKNAIQPTQKILEYL    485
SCHPO   MDTQKTTLPPAVIRLLPKKNTFRLITNLRKRFLIKMGSNKKMLVSTNQTLRPVASILKHL    549
TETTH   -EDSFQKYPQGKLRIIPKKGSFRPIMTFLRKDKQKNIKLN----LNQILMDSQLVFRNL    575
EUPAE   KKS--LGFAPGKLRLIPKKTTFRPIMTFN-KKIVNSDRKTTKLTTNTKLLNSHLMLKTLK    560
                 MOTIF 1 MOTIF 2                           K210
```

FIG. 3A

```
                        α11              β7         α12
        ○──────○────────○──────         ───▶────○────○
TRICA TSKIYKVLEEKYKTSGSLYTCWSEFTQKTQG------QI YGIKVDIRDAYGNVKIPVLCK  266
MOUSE RTKHPHLMGSSVLGMNDIYRTWRAFVLRVRALD-QTPRM YFVKADVTGAYDAIPQGKLVE  717
HUMAN RARRPGLLGASVLGLDDIHRAWRTFVLRVRAQD-PPPEL YFVKVDVTGAYDTIPQDRLTE  727
ARATH QLKEPDVLGSSVFDHDDFYRNLCPYLIHLRSQSGELPPL YFVMKADVFKAFDSVDQGKLLH  706
YEAST RNKRPTSFTKIYSPTQIADRIKEFKQRLLKKNNVLPEL  YFMKFDVKSCYDSIPRMECMR   545
SCHPO INEE----SSGIPFNLEVYMKLLTFKKDLLKHRMFGRKK YFVRIDIKSCYDRIKQDLMFR  605
TETTH KDMLGQKIGYSVFDNKQISEKFAQFIEKWKNKG--RPQI YYVTLDIKKCYDSIDQMKLLN  633
EUPAE NRMFKDPFGFAVFNYDDVMKKYEEFVCKWKQVG--QPKL FFATMDIEKCYDSVNREKLST  618
                                              MOTIF A

α13
       ○
TRICA LIQS--------------------------------------------------------  270
MOUSE VVAN-MIRHSESTYCIRQYAVVRRDSQGQVHKSFRR------------------------  752
HUMAN VIAS--IIKP-QNTYCVRRYAVVQKAAHGHVRKAFKS-----------------------  761
ARATH VIQS--FLKD---EYILNRCRLVCCGK----RSNWVN-----------------------  734
YEAST ILKD--ALKN----------------------ENGFFV---------------------   559
SCHPO IVKK--KLKD--PEFVIRKYATIHATSDR--ATKNFVS---------------------   637
TETTH FFNQSDLIQD---TYFINKYLLFQRNKRPLLQIQQTNNLNSAMEIEEEKINKKPFKMDNI  690
EUPAE FLKTTKLLSS--DFWIMTAQILKRKNNIVIDSKNFRKK----------------------  654
      IFD MOTIF
                                                            α14
                                                           ○───○
TRICA -------------------------------------------IPTHLLDSEKKNFIV  285
MOUSE --------QVTTLSDLQPYMGQFLKHLQDSDASALRNSVVIEQSISMNESSSSLFDFFL  803
HUMAN ----------HVSTLTDLQPYMRQFVAHLQET--SPLRDAVVIEQSSSLNEASSGLFDVFL  810
ARATH ----------KILVSSDKNSNFSRFTSTVPYN----ALQSIVVDKGENHRVRKKDLMVWIG  781
YEAST ----------RSQYFFNTNTGVLKLFNVVNASR-VPKPYELYIDNVRTVHLSNQDVINVVE  609
SCHPO ----------EAFSYFDMVP-FEKVVQLLSMKT----SDTLFVDFVDYWTKSSSEIFKMLK  683
TETTH ----------NFPYYFNLKERQIAYSLYDDDDQILQKGFKEISDDRPFIVINQDKPRCITKDIIHNHLK  750
EUPAE ----------EMKDYFRQKFQKIALEGGQYPTLFSVLENEQNDLNAKKTLIVEAKQRNYFKKDNLLQPVI  714
                                                            IFD MOTIF

β8    β9                 α15
       ▶──  ▶──         ○─────────○
TRICA DHISNQFVAFRRKIYKWNHGLLQGDPLSGCLCELYMAFMDRLYFSNLDKDA-------  336
MOUSE HFLRHSVVKIGDRCYTQCQGIPQGSSLSTLLCSLCFGDMENKLFAEVQRDG--------  854
HUMAN RFMCHHAVRIRGKSYVQCQGIPQGSILSTLLCSLCYGDMENKLFAGIRRDG--------  861
ARATH NMLKNNMLQLDKSFYVQIAGIPQGHRLSSLLCCFYYGHLERTLIYPFLEEASKDVSSKEC  841
YEAST MEIFKTALWVEDKCYIREDGLFQGSSLSAPIVDLVYDDLLEFYSEFKASPSQ--------  661
SCHPO EHLSGHIVKIGNSQYLQKVGIPQGSILSSFLCHFYMEDLIDEYLSFTKKKGS--------  735
TETTH HISQYNVISFNKVKFRQKRGIPQGLNISGVLCSFYFGKLEEEYTQFLKNAEQVNG----- 805
EUPAE NICQYNYINFNGKFYKQTKGIPQGLCVSSILSSFYYATLEESSLGFLRDESMNPEN----  770
                        MOTIF B'

β10   β11                 α16
       ──▶   ──▶         ○──────○
TRICA ------FIHRTVDDYFFCSPHPHKVYDFELLIKG-----VYQVNPTKTRTNLP-  378
MOUSE ------LLLRFVDDFLLVTPHLDQAKTFLSTLHGVPEYGCMINLQKTVVNFP-  901
HUMAN ------LLLRLVDDFLLVTPHLTHAKTFLRTLVRGVPEYGCVVNLRKTVVNFP-  908
ARATH SREEELIIPTSYKLLRFIDDYLFVSTSRDQASSFYHRLKHGFKDYNCFMNETKFCINFED  901
YEAST ---------DTLILKLADDFLIISTDQQQVINIKKLAMGGFQKYNAKANRDKILAVSS-  710
SCHPO -----------VLLRVVDDFLFITVNKKDAKKFLNLSLRGFEKHNFSTSLEKTVINFE-  782
TETTH -----------SINLLMRLTDDYLFISDSQQNALNLIVQLQNCANNNGFMFNDQKITTNFQ-  855
EUPAE --------PNVNLLMRLTDDYLLITTQENNAVLFIEKLINVSRENGFKFNMKKLQTSFPL  822
              MOTIF C                              MOTIF D

β12 β13 β14          α17
              ─▶  ─▶  ─▶        ○────○
TRICA -----------------THRHPQDEIFYCGKIFNLTTRQVRTLYKLPPNYEIRKFKLWNFNN  424
MOUSE ---VEPGTLGGAAPYQLPAHCLFPWCGLLLDTQTLEVFCDYSGYAQTSIKTSLTFQSVFK   954
HUMAN ---VEDEALGGTAFVQMPAHGLFPWCGLLLDTRTLEVQSDYSSYARTSIRASLTFNRGFK   961
ARATH K--EEHRCSSNRMFVGDNGVPFVRWTGLLINSRTFEVQVDYTRYLSGHISSTFSVAWQNK  955
YEAST -----------------QSDDDTVIQFCAMHIFVKELEVWKHSSTMNNFHIRSKSSKG-IFR   746
SCHPO -----NSNGIINNTFFNESKKRMPFFGFSVNMRSLDTLLACPKIDEALFNSTSVELTKH   832
TETTH ----FPQEDYNLEHFKISVQNECQWIGKSIDMNTLEIKS-IQKQTQQEINQTINVAISIK  906
EUPAE SPSKFAKYGMDSVEEQNIVQDYCWIGISIDMKTLALMPNINLRIEGIL-CTLNLMQTK   877
                      MOTIF E         K406    K416 K418 K423
```

*FIG. 3B*

```
              α18      α19       α20               α21
TRICA  QISDDNPARFLQKAMDFPFICNSFTKFEFNTVFNDQRTVFANFYDAMICVAYKFDAAMMA   484
MOUSE  AGKT-----MRNKLLSVLRLK--CHGLFLDLQVNSLQTVCINIYKIFLLQAYRFHACVIQ  1011
HUMAN  AGRN-----MRRKLFGVLRLK--CHSLFLDLQVNSLQTVCTNIYKILLLQAYRFHACVLQ  1018
ARATH  PVRN-----LRQKLCYFLVPK--CHPILFDSNINSGEIVRLNIYQIFLLAAMKFHCYVYE  1012
YEAST  ----------SLIALFNTR--ISYKTIDTNLSTNTVLMQIDHVVKNISECYKSAFKD      800
SCHPO  MGKS-----FFYKILRSSLAS--FAQVFIDITHNSKFNSCCNIYRLGYSMCMRAQAYLKR   889
TETTH  NLKS-----QLKNKLRSLFLN--QLIDYFNPNINSFEGLCRQLYHHSKATVMKFYPFMTK   963
EUPAE  KASM-----WLKKKLKSFLMN--NITHYFRKTITTEDFANKTLNKLFISGGYKYMQCAKE   934

α22
TRICA  LRTSFLVN-----------DFGFIWLVLSSTVRAYASRAFKKIVTYKGGK-YRKVTFQ     530
MOUSE  LPFDQRVR---------KNLTFFLGIISSQASCCYAILKVKNPGMTLKAS---GSFPPE   1058
HUMAN  LPFHQQVW---------KNPTFFLRVISDTASLCYSILKAKNAGMSLGAKGAAGPLPSE   1068
ARATH  VSRFWKLH---------PQTLFKFITISVRYMFRLINRRVRRINTGSSFR-PVLKLYKE   1061
YEAST  LSINVTQN---------MQFHSFLQRIIEMTVSGCPITKCD-------------PLIEY    837
SCHPO  MKDIFIPQ---------RMFITDLLNVIGRKIWKKLAEILGYTSRR--------FLSSA    931
TETTH  LFQIDLKKSKQYSVQYGKENTNENFLKDILYYTVEDVCKILCYLQFEDEINSNIKEIFKN  1023
EUPAE  YKDHFKKN---------LAMSSMIDLEVSKIIYSVTRAFFKYLVCN---------IKDT    975

α23                         α24                 α25
TRICA  CLKSIAWRAFLAVLKRR-----------TEIYKGLIDRIKSREKLTMKFHDGEVDASYFC   579
MOUSE  AAHWLCYQAFLLKLAAH-----------SVIYKCLLGPLRTAQKLLCRKLPEATMTILKA  1107
HUMAN  AVQWLCHQAFLLKLTRH-----------RVTYVPLLGSLRTAQTQLSRKLPGTTLTALEA  1117
ARATH  EVIWLGLDAYIQVLKKK-----------NSRYRMLLIYLKSALSKHS--LSQQLSSELRY  1108
YEAST  EVRFTILNGFLESLSSN-----------TSKFKDNIILLRKEIQHLQAYIYIYIHIVN--   884
SCHPO  EVKWLFCLGMRDGLKP-----------SFKYHPCFEQLIYQFQSLTDLIKPLRPVLRQV    979
TETTH  LYSWIMWDIIVSYLKKKKQFKGYLNKLLQKIRKSRFFYLKEGCKSLQLILSQQKYQLNKK  1083
EUPAE  IFGEEHYPDFFLSTLKH-----------FIEIFSTKKYIFNRVCMILKAKEAKLKSD    1021

TRICA  KLPEKFRFVKINRKASI-----------------   596
MOUSE  AADPALSTDFQTILD-------------------  1122
HUMAN  AANPALPSDFKTILD-------------------  1132
ARATH  ATDRSNSSSLWKLNY-------------------  1123
YEAST  ----------------------------------
SCHPO  LFLHRRIAD-------------------------   988
TETTH  ELEAIEFIDLNNLIQDIKTLIPKISAKSNQQNTN  1117
EUPAE  QCQSLIQYDA------------------------  1031
```

*FIG. 3C*

SEQUENCE LISTING

```
<160> NUMBER OF SEQ ID NOS: 21

<210> SEQ ID NO 1
<211> LENGTH: 282
<212> TYPE: PRT
<213> ORGANISM: Tetrahymena thermophila

<400> SEQUENCE: 1

Ser Ser Phe Phe Asn Tyr Ser Glu Ile Lys Lys Gly Phe Gln Phe Lys
1               5                   10                  15

Val Ile Gln Glu Lys Leu Gln Gly Arg Gln Phe Ile Asn Ser Asp Lys
            20                  25                  30

Ile Lys Pro Asp His Pro Gln Thr Ile Ile Lys Lys Thr Leu Leu Lys
        35                  40                  45

Glu Tyr Gln Ser Lys Asn Phe Ser Cys Gln Glu Glu Arg Asp Leu Phe
    50                  55                  60

Leu Glu Phe Thr Glu Lys Ile Val Gln Asn Phe His Asn Ile Asn Phe
65                  70                  75                  80

Asn Tyr Leu Leu Lys Lys Phe Cys Lys Leu Pro Glu Asn Tyr Gln Ser
                85                  90                  95

Leu Lys Ser Gln Val Lys Gln Ile Val Gln Ser Glu Asn Lys Ala Asn
```

```
                 100                 105                 110
Gln Gln Ser Cys Glu Asn Leu Phe Asn Ser Leu Tyr Asp Thr Glu Ile
            115                 120                 125
Ser Tyr Lys Gln Ile Thr Asn Phe Leu Arg Gln Ile Ile Gln Asn Cys
        130                 135                 140
Val Pro Asn Gln Leu Leu Gly Lys Lys Asn Phe Lys Val Phe Leu Glu
145                 150                 155                 160
Lys Leu Tyr Glu Phe Val Gln Met Lys Arg Phe Glu Asn Gln Lys Val
                165                 170                 175
Leu Asp Tyr Ile Cys Phe Met Asp Val Phe Asp Val Glu Trp Phe Val
            180                 185                 190
Asp Leu Lys Asn Gln Lys Phe Thr Gln Lys Arg Lys Tyr Ile Ser Asp
        195                 200                 205
Lys Arg Lys Ile Leu Gly Asp Leu Ile Val Phe Ile Ile Asn Lys Ile
    210                 215                 220
Val Ile Pro Val Leu Arg Tyr Asn Phe Tyr Ile Thr Glu Lys His Lys
225                 230                 235                 240
Glu Gly Ser Gln Ile Phe Tyr Tyr Arg Lys Pro Ile Trp Lys Leu Val
                245                 250                 255
Ser Lys Leu Thr Ile Val Lys Leu Glu Glu Asn Leu Glu Lys Val
            260                 265                 270
Glu Glu Lys Leu Ile Pro Glu Asp Ser Phe
        275                 280

<210> SEQ ID NO 2
<211> LENGTH: 255
<212> TYPE: PRT
<213> ORGANISM: Euplotes aediculatus

<400> SEQUENCE: 2

Asn Gln Phe Phe Lys Lys His Glu Phe Val Ser Asn Lys Asn Ile
1               5                   10                  15
Ser Ala Met Asp Arg Ala Gln Thr Ile Phe Thr Asn Ile Phe Arg Phe
            20                  25                  30
Asn Arg Ile Arg Lys Lys Leu Lys Asp Lys Val Ile Glu Lys Ile Ala
        35                  40                  45
Tyr Met Leu Glu Lys Val Lys Asp Phe Asn Phe Asn Tyr Tyr Leu Thr
    50                  55                  60
Lys Ser Cys Pro Leu Pro Glu Asn Trp Arg Glu Arg Lys Gln Lys Ile
65                  70                  75                  80
Glu Asn Leu Ile Asn Lys Thr Arg Glu Glu Lys Ser Lys Tyr Tyr Glu
                85                  90                  95
Glu Leu Phe Ser Tyr Thr Thr Asp Asn Lys Cys Val Thr Gln Phe Ile
            100                 105                 110
Asn Glu Phe Phe Tyr Asn Ile Leu Pro Lys Asp Phe Leu Thr Gly Arg
        115                 120                 125
Asn Arg Lys Asn Phe Gln Lys Lys Val Lys Lys Tyr Val Glu Leu Asn
    130                 135                 140
Lys His Glu Leu Ile His Lys Asn Leu Leu Leu Glu Lys Ile Asn Thr
145                 150                 155                 160
Arg Glu Ile Ser Trp Met Gln Val Glu Thr Ser Ala Lys His Phe Tyr
                165                 170                 175
Tyr Phe Asp His Glu Asn Ile Tyr Val Leu Trp Lys Leu Leu Arg Trp
            180                 185                 190
Ile Phe Glu Asp Leu Val Val Ser Leu Ile Arg Cys Phe Phe Tyr Val
```

```
            195                 200                 205
Thr Glu Gln Gln Lys Ser Tyr Ser Lys Thr Tyr Tyr Tyr Arg Lys Asn
    210                 215                 220

Ile Trp Asp Val Ile Met Lys Met Ser Ile Ala Asp Leu Lys Lys Glu
225                 230                 235                 240

Thr Leu Ala Glu Val Gln Lys Glu Val Glu Trp Lys Lys
                245                 250                 255

<210> SEQ ID NO 3
<211> LENGTH: 251
<212> TYPE: PRT
<213> ORGANISM: Oxytricha trifallax

<400> SEQUENCE: 3

Phe Phe Gln Lys His Ile Leu Asn Ser Lys Thr Leu Ser Gln Gln Gln
1               5                   10                  15

Ile Arg Asp Asn Ile Tyr Lys Glu Val Phe Gly Phe Asn Arg Val Arg
            20                  25                  30

Ala Glu Leu Lys Gly Lys Val Met Ser Ile Ile Glu Gln Val Ile Val
        35                  40                  45

Asn Gln Lys Lys Phe Asp Phe Lys Tyr Tyr Leu Ser Lys Asn Cys Pro
50                  55                  60

Leu Pro Glu Asn Trp Lys Asn Leu Lys Lys Ser Phe Leu Glu Asp Ala
65                  70                  75                  80

Ala Val Ser Gly Glu Leu Arg Gly Gln Val Phe Arg Gln Leu Phe Glu
                85                  90                  95

Tyr Gln Gln Asp Gln Arg Gln Ile Ser Asn Phe Leu Thr Glu Phe Val
            100                 105                 110

Ala Asn Val Phe Pro Lys Asn Phe Leu Glu Gly Lys Asn Lys Lys Ile
        115                 120                 125

Phe Asn Lys Lys Met Leu Gln Phe Val Lys Phe Asn Arg Phe Glu Ser
130                 135                 140

Phe Thr Lys Ile Ser Leu Leu Asn Lys Phe Arg Val Asn Glu Val Ser
145                 150                 155                 160

Trp Leu Ser Phe Lys Cys Lys Asp Glu Asn Lys Lys Phe Phe Met Asn
                165                 170                 175

Glu Asn Glu His Val Phe Phe Lys Val Leu Lys Trp Val Phe Glu Asp
            180                 185                 190

Leu Ala Ile Thr Leu Met Arg Cys Tyr Phe Tyr Ser Thr Glu Lys Ala
        195                 200                 205

Lys Glu Tyr Gln Arg Ile Phe Tyr Tyr Arg Lys Asn Ile Trp Asn Met
210                 215                 220

Ile Met Arg Leu Ser Ile Asp Asp Leu Leu Lys Gln Asn Leu Lys Gln
225                 230                 235                 240

Val Gln Glu Lys Glu Val Glu Glu Trp Lys Lys
                245                 250

<210> SEQ ID NO 4
<211> LENGTH: 296
<212> TYPE: PRT
<213> ORGANISM: Homo sapiens

<400> SEQUENCE: 4

Pro Trp Asp Thr Pro Cys Pro Pro Val Tyr Ala Glu Thr Lys His Phe
1               5                   10                  15

Leu Tyr Ser Ser Gly Asp Lys Glu Gln Leu Arg Pro Ser Phe Leu Leu
            20                  25                  30
```

Ser Ser Leu Arg Pro Ser Leu Thr Gly Ala Arg Arg Leu Val Glu Thr
            35                  40                  45

Ile Phe Leu Gly Ser Arg Pro Trp Met Pro Gly Thr Pro Arg Arg Leu
 50                  55                  60

Pro Arg Leu Pro Gln Arg Tyr Trp Gln Met Arg Pro Leu Phe Leu Glu
 65                  70                  75                  80

Leu Leu Gly Asn His Ala Gln Cys Pro Tyr Gly Val Leu Leu Lys Thr
                    85                  90                  95

His Cys Pro Leu Arg Ala Ala Val Thr Pro Ala Ala Gly Val Cys Ala
                100                 105                 110

Arg Glu Lys Pro Gln Gly Ser Val Ala Ala Pro Glu Glu Asp Thr
            115                 120                 125

Asp Pro Arg Arg Leu Val Gln Leu Leu Arg Gln His Ser Ser Pro Trp
    130                 135                 140

Gln Val Tyr Gly Phe Val Arg Ala Cys Leu Arg Arg Leu Val Pro Pro
145                 150                 155                 160

Gly Leu Trp Gly Ser Arg His Asn Glu Arg Arg Phe Leu Arg Asn Thr
                165                 170                 175

Lys Lys Phe Ile Ser Leu Gly Lys His Ala Lys Leu Ser Leu Gln Glu
                180                 185                 190

Leu Thr Trp Lys Met Ser Val Arg Asp Cys Ala Trp Leu Arg Arg Ser
            195                 200                 205

Pro Gly Val Gly Cys Val Pro Ala Ala Glu His Arg Leu Arg Glu Glu
    210                 215                 220

Ile Leu Ala Lys Phe Leu His Trp Leu Met Ser Val Tyr Val Val Glu
225                 230                 235                 240

Leu Leu Arg Ser Phe Phe Tyr Val Thr Glu Thr Thr Phe Gln Lys Asn
                245                 250                 255

Arg Leu Phe Phe Tyr Arg Lys Ser Val Trp Ser Lys Leu Gln Ser Ile
                260                 265                 270

Gly Ile Arg Gln His Leu Lys Arg Val Gln Leu Arg Glu Leu Ser Glu
            275                 280                 285

Ala Glu Val Arg Gln His Arg Glu
    290                 295

<210> SEQ ID NO 5
<211> LENGTH: 281
<212> TYPE: PRT
<213> ORGANISM: Mus musculus

<400> SEQUENCE: 5

Gln Asn Ala Phe Gln Leu Arg Pro Phe Ile Glu Thr Arg His Phe Leu
1               5                   10                  15

Tyr Ser Arg Gly Asp Gly Gln Glu Arg Leu Asn Pro Ser Phe Leu Leu
            20                  25                  30

Ser Asn Leu Gln Pro Asn Leu Thr Gly Ala Arg Arg Leu Val Glu Ile
        35                  40                  45

Ile Phe Leu Gly Ser Arg Pro Arg Thr Ser Gly Pro Leu Cys Arg Thr
 50                  55                  60

His Arg Leu Ser Arg Arg Tyr Trp Gln Met Arg Pro Leu Phe Gln Gln
 65                  70                  75                  80

Leu Leu Val Asn His Ala Glu Cys Gln Tyr Val Arg Leu Leu Arg Ser
                85                  90                  95

His Cys Arg Phe Arg Thr Ala Asn Gln Gln Val Thr Asp Ala Leu Asn
                100                 105                 110

```
Thr Ser Pro Pro His Leu Met Asp Leu Leu Arg Leu His Ser Ser Pro
        115                 120                 125

Trp Gln Val Tyr Gly Phe Leu Arg Ala Cys Leu Cys Lys Val Val Ser
130                 135                 140

Ala Ser Leu Trp Gly Thr Arg His Asn Glu Arg Arg Phe Phe Lys Asn
145                 150                 155                 160

Leu Lys Lys Phe Ile Ser Leu Gly Lys Tyr Gly Lys Leu Ser Leu Gln
                165                 170                 175

Glu Leu Met Trp Lys Met Lys Val Glu Asp Cys His Trp Leu Arg Ser
            180                 185                 190

Ser Pro Gly Lys Asp Arg Val Pro Ala Ala Glu His Arg Leu Arg Glu
        195                 200                 205

Arg Ile Leu Ala Thr Phe Leu Phe Trp Leu Met Asp Thr Tyr Val Val
    210                 215                 220

Gln Leu Leu Arg Ser Phe Phe Tyr Ile Thr Glu Ser Thr Phe Gln Lys
225                 230                 235                 240

Asn Arg Leu Phe Phe Tyr Arg Lys Ser Val Trp Ser Lys Leu Gln Ser
                245                 250                 255

Ile Gly Val Arg Gln His Leu Glu Arg Val Arg Leu Arg Glu Leu Ser
            260                 265                 270

Gln Glu Glu Val Arg His His Gln Asp
        275                 280

<210> SEQ ID NO 6
<211> LENGTH: 234
<212> TYPE: PRT
<213> ORGANISM: Schizosaccharomyces pombe

<400> SEQUENCE: 6

Gln Trp Ile Phe Pro Arg Gln Phe Gly Leu Ile Asn Ala Phe Gln Val
1               5                   10                  15

Lys Gln Leu His Lys Val Ile Pro Leu Val Ser Gln Ser Thr Val Val
            20                  25                  30

Pro Lys Arg Leu Leu Lys Val Tyr Pro Leu Ile Glu Gln Thr Ala Lys
        35                  40                  45

Arg Leu His Arg Ile Ser Leu Ser Lys Val Tyr Asn His Tyr Cys Pro
    50                  55                  60

Tyr Ile Asp Thr His Asp Asp Glu Lys Ile Leu Ser Tyr Ser Leu Lys
65                  70                  75                  80

Pro Asn Gln Val Phe Ala Phe Leu Arg Ser Ile Leu Val Arg Val Phe
                85                  90                  95

Pro Lys Leu Ile Trp Gly Asn Gln Arg Ile Phe Glu Ile Ile Leu Lys
            100                 105                 110

Asp Leu Glu Thr Phe Leu Lys Leu Ser Arg Tyr Glu Ser Phe Ser Leu
        115                 120                 125

His Tyr Leu Met Ser Asn Ile Lys Ile Ser Glu Ile Glu Trp Leu Val
    130                 135                 140

Leu Gly Lys Arg Ser Asn Ala Lys Met Cys Leu Ser Asp Phe Glu Lys
145                 150                 155                 160

Arg Lys Gln Ile Phe Ala Glu Phe Ile Tyr Trp Leu Tyr Asn Ser Phe
                165                 170                 175

Ile Ile Pro Ile Leu Gln Ser Phe Phe Tyr Ile Thr Glu Ser Ser Asp
            180                 185                 190

Leu Arg Asn Arg Thr Val Tyr Phe Arg Lys Asp Ile Trp Lys Leu Leu
        195                 200                 205
```

```
Cys Arg Pro Phe Ile Thr Ser Met Lys Met Glu Ala Phe Glu Lys Ile
        210                 215                 220

Asn Glu Asn Asn Val Arg Met Asp Thr Gln
225                 230

<210> SEQ ID NO 7
<211> LENGTH: 232
<212> TYPE: PRT
<213> ORGANISM: Saccharomyces cerevisiae

<400> SEQUENCE: 7

Ser Ser Phe Phe Pro Tyr Ser Lys Ile Leu Pro Ser Ser Ser Ile
1               5                   10                  15

Lys Lys Leu Thr Asp Leu Arg Glu Ala Ile Phe Pro Thr Asn Leu Val
            20                  25                  30

Lys Ile Pro Gln Arg Leu Lys Val Arg Ile Asn Leu Thr Leu Gln Lys
        35                  40                  45

Leu Leu Lys Arg His Lys Arg Leu Asn Tyr Val Ser Ile Leu Asn Ser
    50                  55                  60

Ile Cys Pro Pro Leu Glu Gly Thr Val Leu Asp Leu Ser His Leu Ser
65                  70                  75                  80

Arg Gln Ser Pro Lys Glu Arg Val Leu Lys Phe Ile Ile Val Ile Leu
                85                  90                  95

Gln Lys Leu Leu Pro Gln Glu Met Phe Gly Ser Lys Lys Asn Lys Gly
            100                 105                 110

Lys Ile Ile Lys Asn Leu Asn Leu Leu Ser Leu Pro Leu Asn Gly
        115                 120                 125

Tyr Leu Pro Phe Asp Ser Leu Leu Lys Lys Leu Arg Leu Lys Asp Phe
    130                 135                 140

Arg Trp Leu Phe Ile Ser Asp Ile Trp Phe Thr Lys His Asn Phe Glu
145                 150                 155                 160

Asn Leu Asn Gln Leu Ala Ile Cys Phe Ile Ser Trp Leu Phe Arg Gln
                165                 170                 175

Leu Ile Pro Lys Ile Ile Gln Thr Phe Phe Tyr Cys Thr Glu Ile Ser
            180                 185                 190

Ser Thr Val Thr Ile Val Tyr Phe Arg His Asp Thr Trp Asn Lys Leu
        195                 200                 205

Ile Thr Pro Phe Ile Val Glu Tyr Phe Lys Thr Tyr Leu Val Glu Asn
    210                 215                 220

Asn Val Cys Arg Asn His Asn Ser
225                 230

<210> SEQ ID NO 8
<211> LENGTH: 313
<212> TYPE: PRT
<213> ORGANISM: Arabidopsis thaliana

<400> SEQUENCE: 8

Thr Asp Phe Val Lys Gln Ala Lys Gln Val Lys Arg Asn Lys Asn Phe
1               5                   10                  15

Lys Phe Gly Leu Ser Glu Thr Tyr Ser Val Ile Pro Pro Asn His Ile
            20                  25                  30

Leu Lys Thr Leu Arg Pro Asn Cys Ser Asp Ser Lys Leu Leu Met Asn
        35                  40                  45

His Ile Phe Gly Glu Val Asn Val Trp Ser Thr Thr Pro Ser His Gly
    50                  55                  60
```

```
Lys Gly Asn Cys Pro Ser Gly Ser Ile Cys Leu Tyr His Ser Leu Leu
 65                  70                  75                  80

Lys Ser Leu Lys Asn Leu Ile Gly Lys Thr Lys Ser Ser His Leu Lys
                 85                  90                  95

Met Leu Leu Asp Lys His Cys Pro Val Leu Leu Gln Glu Asp Ala
            100                 105                 110

Leu Lys Ser Gly Thr Thr Ser Gln Ser Ser Arg Arg Gln Lys Ala Asp
        115                 120                 125

Lys Leu Pro His Gly Ser Ser Ser Gln Thr Gly Lys Pro Lys Cys
    130                 135                 140

Pro Ser Val Glu Glu Arg Lys Leu Tyr Cys Thr Asn Asp Gln Val Val
145                 150                 155                 160

Ser Phe Ile Trp Ala Ile Cys Arg Tyr Ile Val Pro Glu Ser Leu Leu
                165                 170                 175

Gly Thr Thr His Gln Met Arg Val Leu Arg Lys Asn Ile Ala Trp Phe
                180                 185                 190

Val Ser Arg Arg Arg Asn Glu Lys Cys Thr Val Asn Gln Phe Leu His
                195                 200                 205

Lys Val Lys Pro Ser Asp Phe Pro Phe Ala Arg Lys Glu Leu Cys
    210                 215                 220

Cys Met Val Asn Gly His Glu Leu Gln Ser Glu Ser Ile Arg Ser Thr
225                 230                 235                 240

Gln Gln Met Leu Cys Thr Lys Trp Ile Ser Trp Leu Phe Leu Glu Ile
                245                 250                 255

Val Lys Lys Leu Val His Phe Asn Phe Tyr Ala Thr Glu Ser Gln Gly
                260                 265                 270

Gly Arg Leu Asn Ile Tyr Tyr Tyr Arg Lys Arg Ser Trp Glu Arg Leu
                275                 280                 285

Ile Ser Lys Glu Ile Ser Lys Ala Leu Asp Gly Tyr Val Leu Val Asp
                290                 295                 300

Asp Ala Glu Ala Glu Ser Ser Arg Lys
305                 310

<210> SEQ ID NO 9
<211> LENGTH: 596
<212> TYPE: PRT
<213> ORGANISM: Tribolium castaneum

<400> SEQUENCE: 9

Met Val His Tyr Tyr Arg Leu Ser Leu Lys Ser Arg Gln Lys Ala Pro
1               5                   10                  15

Lys Ile Val Asn Ser Lys Tyr Asn Ser Ile Leu Asn Ile Ala Leu Lys
            20                  25                  30

Asn Phe Arg Leu Cys Lys Lys His Lys Thr Lys Lys Pro Val Gln Ile
        35                  40                  45

Leu Ala Leu Leu Gln Glu Ile Ile Pro Lys Ser Tyr Phe Gly Thr Thr
    50                  55                  60

Thr Asn Leu Lys Arg Phe Tyr Lys Val Val Glu Lys Ile Leu Thr Gln
65                  70                  75                  80

Ser Ser Phe Glu Cys Ile His Leu Ser Val Leu His Lys Cys Tyr Asp
                85                  90                  95

Tyr Asp Ala Ile Pro Trp Leu Gln Asn Val Glu Pro Asn Leu Arg Pro
            100                 105                 110

Lys Leu Leu Leu Lys His Asn Leu Phe Leu Leu Asp Asn Ile Val Lys
        115                 120                 125
```

-continued

```
Pro Ile Ile Ala Phe Tyr Tyr Lys Pro Ile Lys Thr Leu Asn Gly His
130                 135                 140

Glu Ile Lys Phe Ile Arg Lys Glu Glu Tyr Ile Ser Phe Glu Ser Lys
145                 150                 155                 160

Val Phe His Lys Leu Lys Lys Met Lys Tyr Leu Val Glu Val Gln Asp
                165                 170                 175

Glu Val Lys Pro Arg Gly Val Leu Asn Ile Ile Pro Lys Gln Asp Asn
            180                 185                 190

Phe Arg Ala Ile Val Ser Ile Phe Pro Asp Ser Ala Arg Lys Pro Phe
        195                 200                 205

Phe Lys Leu Leu Thr Ser Lys Ile Tyr Lys Val Leu Glu Glu Lys Tyr
    210                 215                 220

Lys Thr Ser Gly Ser Leu Tyr Thr Cys Trp Ser Glu Phe Thr Gln Lys
225                 230                 235                 240

Thr Gln Gly Gln Ile Tyr Gly Ile Lys Val Asp Ile Arg Asp Ala Tyr
                245                 250                 255

Gly Asn Val Lys Ile Pro Val Leu Cys Lys Leu Ile Gln Ser Ile Pro
            260                 265                 270

Thr His Leu Leu Asp Ser Glu Lys Lys Asn Phe Ile Val Asp His Ile
        275                 280                 285

Ser Asn Gln Phe Val Ala Phe Arg Arg Lys Ile Tyr Lys Trp Asn His
    290                 295                 300

Gly Leu Leu Gln Gly Asp Pro Leu Ser Gly Cys Leu Cys Glu Leu Tyr
305                 310                 315                 320

Met Ala Phe Met Asp Arg Leu Tyr Phe Ser Asn Leu Asp Lys Asp Ala
                325                 330                 335

Phe Ile His Arg Thr Val Asp Asp Tyr Phe Phe Cys Ser Pro His Pro
            340                 345                 350

His Lys Val Tyr Asp Phe Glu Leu Leu Ile Lys Gly Val Tyr Gln Val
        355                 360                 365

Asn Pro Thr Lys Thr Arg Thr Asn Leu Pro Thr His Arg His Pro Gln
    370                 375                 380

Asp Glu Ile Pro Tyr Cys Gly Lys Ile Phe Asn Leu Thr Thr Arg Gln
385                 390                 395                 400

Val Arg Thr Leu Tyr Lys Leu Pro Pro Asn Tyr Glu Ile Arg His Lys
                405                 410                 415

Phe Lys Leu Trp Asn Phe Asn Asn Gln Ile Ser Asp Asp Asn Pro Ala
            420                 425                 430

Arg Phe Leu Gln Lys Ala Met Asp Phe Pro Phe Ile Cys Asn Ser Phe
        435                 440                 445

Thr Lys Phe Glu Phe Asn Thr Val Phe Asn Asp Gln Arg Thr Val Phe
    450                 455                 460

Ala Asn Phe Tyr Asp Ala Met Ile Cys Val Ala Tyr Lys Phe Asp Ala
465                 470                 475                 480

Ala Met Met Ala Leu Arg Thr Ser Phe Leu Val Asn Asp Phe Gly Phe
                485                 490                 495

Ile Trp Leu Val Leu Ser Ser Thr Val Arg Ala Tyr Ala Ser Arg Ala
            500                 505                 510

Phe Lys Lys Ile Val Thr Tyr Lys Gly Gly Lys Tyr Arg Lys Val Thr
        515                 520                 525

Phe Gln Cys Leu Lys Ser Ile Ala Trp Arg Ala Phe Leu Ala Val Leu
    530                 535                 540

Lys Arg Arg Thr Glu Ile Tyr Lys Gly Leu Ile Asp Arg Ile Lys Ser
545                 550                 555                 560
```

Arg Glu Lys Leu Thr Met Lys Phe His Asp Gly Glu Val Asp Ala Ser
            565                 570                 575

Tyr Phe Cys Lys Leu Pro Glu Lys Phe Arg Phe Val Lys Ile Asn Arg
            580                 585                 590

Lys Ala Ser Ile
            595

<210> SEQ ID NO 10
<211> LENGTH: 788
<212> TYPE: PRT
<213> ORGANISM: Mus musculus

<400> SEQUENCE: 10

Phe Leu Tyr Ser Arg Gly Asp Gly Gln Glu Arg Leu Asn Pro Ser Phe
1               5                   10                  15

Leu Leu Ser Asn Leu Gln Pro Asn Leu Thr Gly Ala Arg Arg Leu Val
            20                  25                  30

Glu Ile Ile Phe Leu Gly Ser Arg Pro Arg Thr Ser Gly Pro Leu Cys
        35                  40                  45

Arg Thr His Arg Leu Ser Arg Arg Tyr Trp Gln Met Arg Pro Leu Phe
    50                  55                  60

Gln Gln Leu Leu Val Asn His Ala Glu Cys Gln Tyr Val Arg Leu Leu
65                  70                  75                  80

Arg Ser His Cys Arg Phe Arg Thr Ala Asn Gln Gln Val Thr Asp Ala
                85                  90                  95

Leu Asn Thr Ser Pro Pro His Leu Met Asp Leu Leu Arg Leu His Ser
            100                 105                 110

Ser Pro Trp Gln Val Tyr Gly Phe Leu Arg Ala Cys Leu Cys Lys Val
        115                 120                 125

Val Ser Ala Ser Leu Trp Gly Thr Arg His Asn Glu Arg Arg Phe Phe
    130                 135                 140

Lys Asn Leu Lys Lys Phe Ile Ser Leu Gly Lys Tyr Gly Lys Leu Ser
145                 150                 155                 160

Leu Gln Glu Leu Met Trp Lys Met Lys Val Glu Asp Cys His Trp Leu
                165                 170                 175

Arg Ser Ser Pro Gly Lys Asp Arg Val Pro Ala Ala Glu His Arg Leu
            180                 185                 190

Arg Glu Arg Ile Leu Ala Thr Phe Leu Phe Trp Leu Met Asp Thr Tyr
        195                 200                 205

Val Val Gln Leu Leu Arg Ser Phe Phe Tyr Ile Thr Glu Ser Thr Phe
    210                 215                 220

Gln Lys Asn Arg Leu Phe Phe Tyr Arg Lys Ser Val Trp Ser Lys Leu
225                 230                 235                 240

Gln Ser Ile Gly Val Arg Gln His Leu Glu Arg Val Arg Leu Arg Glu
                245                 250                 255

Leu Ser Gln Glu Glu Val Arg His His Gln Asp Thr Trp Leu Ala Met
            260                 265                 270

Pro Ile Cys Arg Leu Arg Phe Ile Pro Lys Pro Asn Gly Leu Arg Pro
        275                 280                 285

Ile Val Asn Met Ser Tyr Ser Met Gly Thr Arg Ala Leu Gly Arg Arg
    290                 295                 300

Lys Gln Ala Gln His Phe Thr Gln Arg Leu Lys Thr Leu Phe Ser Met
305                 310                 315                 320

Leu Asn Tyr Glu Arg Thr Lys His Pro His Leu Met Gly Ser Ser Val
                325                 330                 335

```
Leu Gly Met Asn Asp Ile Tyr Arg Thr Trp Arg Ala Phe Val Leu Arg
            340                 345                 350

Val Arg Ala Leu Asp Gln Thr Pro Arg Met Tyr Phe Val Lys Ala Asp
            355                 360                 365

Val Thr Gly Ala Tyr Asp Ala Ile Pro Gln Gly Lys Leu Val Glu Val
            370                 375                 380

Val Ala Asn Met Ile Arg His Ser Glu Ser Thr Tyr Cys Ile Arg Gln
385                 390                 395                 400

Tyr Ala Val Val Arg Arg Asp Ser Gln Gly Gln Val His Lys Ser Phe
            405                 410                 415

Arg Arg Gln Val Thr Thr Leu Ser Asp Leu Gln Pro Tyr Met Gly Gln
            420                 425                 430

Phe Leu Lys His Leu Gln Asp Ser Asp Ala Ser Ala Leu Arg Asn Ser
            435                 440                 445

Val Val Ile Glu Gln Ser Ile Ser Met Asn Glu Ser Ser Ser Ser Leu
            450                 455                 460

Phe Asp Phe Phe Leu His Phe Leu Arg His Ser Val Val Lys Ile Gly
465                 470                 475                 480

Asp Arg Cys Tyr Thr Gln Cys Gln Gly Ile Pro Gln Gly Ser Ser Leu
            485                 490                 495

Ser Thr Leu Leu Cys Ser Leu Cys Phe Gly Asp Met Glu Asn Lys Leu
            500                 505                 510

Phe Ala Glu Val Gln Arg Asp Gly Leu Leu Leu Arg Phe Val Asp Asp
            515                 520                 525

Phe Leu Leu Val Thr Pro His Leu Asp Gln Ala Lys Thr Phe Leu Ser
530                 535                 540

Thr Leu Val His Gly Val Pro Glu Tyr Gly Cys Met Ile Asn Leu Gln
545                 550                 555                 560

Lys Thr Val Val Asn Phe Pro Val Glu Pro Gly Thr Leu Gly Gly Ala
            565                 570                 575

Ala Pro Tyr Gln Leu Pro Ala His Cys Leu Phe Pro Trp Cys Gly Leu
            580                 585                 590

Leu Leu Asp Thr Gln Thr Leu Glu Val Phe Cys Asp Tyr Ser Gly Tyr
            595                 600                 605

Ala Gln Thr Ser Ile Lys Thr Ser Leu Thr Phe Gln Ser Val Phe Lys
            610                 615                 620

Ala Gly Lys Thr Met Arg Asn Lys Leu Leu Ser Val Leu Arg Leu Lys
625                 630                 635                 640

Cys His Gly Leu Phe Leu Asp Leu Gln Val Asn Ser Leu Gln Thr Val
            645                 650                 655

Cys Ile Asn Ile Tyr Lys Ile Phe Leu Leu Gln Ala Tyr Arg Phe His
            660                 665                 670

Ala Cys Val Ile Gln Leu Pro Phe Asp Gln Arg Val Arg Lys Asn Leu
            675                 680                 685

Thr Phe Phe Leu Gly Ile Ile Ser Ser Gln Ala Ser Cys Cys Tyr Ala
            690                 695                 700

Ile Leu Lys Val Lys Asn Pro Gly Met Thr Leu Lys Ala Ser Gly Ser
705                 710                 715                 720

Phe Pro Pro Glu Ala Ala His Trp Leu Cys Tyr Gln Ala Phe Leu Leu
            725                 730                 735

Lys Leu Ala Ala His Ser Val Ile Tyr Lys Cys Leu Leu Gly Pro Leu
            740                 745                 750

Arg Thr Ala Gln Lys Leu Leu Cys Arg Lys Leu Pro Glu Ala Thr Met
```

```
                    755                 760                 765
Thr Ile Leu Lys Ala Ala Asp Pro Ala Leu Ser Thr Asp Phe Gln
            770                 775                 780

Thr Ile Leu Asp
785

<210> SEQ ID NO 11
<211> LENGTH: 802
<212> TYPE: PRT
<213> ORGANISM: Homo sapiens

<400> SEQUENCE: 11

Phe Leu Tyr Ser Ser Gly Asp Lys Glu Gln Leu Arg Pro Ser Phe Leu
1               5                   10                  15

Leu Ser Ser Leu Arg Pro Ser Leu Thr Gly Ala Arg Arg Leu Val Glu
            20                  25                  30

Thr Ile Phe Leu Gly Ser Arg Pro Trp Met Pro Gly Thr Pro Arg Arg
        35                  40                  45

Leu Pro Arg Leu Pro Gln Arg Tyr Trp Gln Met Arg Pro Leu Phe Leu
    50                  55                  60

Glu Leu Leu Gly Asn His Ala Gln Cys Pro Tyr Gly Val Leu Leu Lys
65                  70                  75                  80

Thr His Cys Pro Leu Arg Ala Ala Val Thr Pro Ala Ala Gly Val Cys
                85                  90                  95

Ala Arg Glu Lys Pro Gln Gly Ser Val Ala Ala Pro Glu Glu Glu Asp
            100                 105                 110

Thr Asp Pro Arg Arg Leu Val Gln Leu Leu Arg Gln His Ser Ser Pro
        115                 120                 125

Trp Gln Val Tyr Gly Phe Val Arg Ala Cys Leu Arg Arg Leu Val Pro
    130                 135                 140

Pro Gly Leu Trp Gly Ser Arg His Asn Glu Arg Arg Phe Leu Arg Asn
145                 150                 155                 160

Thr Lys Lys Phe Ile Ser Leu Gly Lys His Ala Lys Leu Ser Leu Gln
                165                 170                 175

Glu Leu Thr Trp Lys Met Ser Val Arg Asp Cys Ala Trp Leu Arg Arg
            180                 185                 190

Ser Pro Gly Val Gly Cys Val Pro Ala Ala Glu His Arg Leu Arg Glu
        195                 200                 205

Glu Ile Leu Ala Lys Phe Leu His Trp Leu Met Ser Val Tyr Val Val
    210                 215                 220

Glu Leu Leu Arg Ser Phe Phe Tyr Val Thr Glu Thr Thr Phe Gln Lys
225                 230                 235                 240

Asn Arg Leu Phe Phe Tyr Arg Lys Ser Val Trp Ser Lys Leu Gln Ser
                245                 250                 255

Ile Gly Ile Arg Gln His Leu Lys Arg Val Gln Leu Arg Glu Leu Ser
            260                 265                 270

Glu Ala Glu Val Arg Gln His Arg Glu Ala Arg Pro Ala Leu Leu Thr
        275                 280                 285

Ser Arg Leu Arg Phe Ile Pro Lys Pro Asp Gly Leu Arg Pro Ile Val
    290                 295                 300

Asn Met Asp Tyr Val Val Gly Ala Arg Thr Phe Arg Arg Glu Lys Arg
305                 310                 315                 320

Ala Glu Arg Leu Thr Ser Arg Val Lys Ala Leu Phe Ser Val Leu Asn
                325                 330                 335

Tyr Glu Arg Ala Arg Arg Pro Gly Leu Leu Gly Ala Ser Val Leu Gly
```

-continued

```
                340                 345                 350
Leu Asp Asp Ile His Arg Ala Trp Arg Thr Phe Val Leu Arg Val Arg
            355                 360                 365
Ala Gln Asp Pro Pro Glu Leu Tyr Phe Val Lys Val Asp Val Thr
        370                 375                 380
Gly Ala Tyr Asp Thr Ile Pro Gln Asp Arg Leu Thr Glu Val Ile Ala
385                 390                 395                 400
Ser Ile Ile Lys Pro Gln Asn Thr Tyr Cys Val Arg Arg Tyr Ala Val
                405                 410                 415
Val Gln Lys Ala Ala His Gly His Val Arg Lys Ala Phe Lys Ser His
            420                 425                 430
Val Ser Thr Leu Thr Asp Leu Gln Pro Tyr Met Arg Gln Phe Val Ala
        435                 440                 445
His Leu Gln Glu Thr Ser Pro Leu Arg Asp Ala Val Val Ile Glu Gln
    450                 455                 460
Ser Ser Ser Leu Asn Glu Ala Ser Ser Gly Leu Phe Asp Val Phe Leu
465                 470                 475                 480
Arg Phe Met Cys His His Ala Val Arg Ile Arg Gly Lys Ser Tyr Val
                485                 490                 495
Gln Cys Gln Gly Ile Pro Gln Gly Ser Ile Leu Ser Thr Leu Leu Cys
            500                 505                 510
Ser Leu Cys Tyr Gly Asp Met Glu Asn Lys Leu Phe Ala Gly Ile Arg
        515                 520                 525
Arg Asp Gly Leu Leu Leu Arg Leu Val Asp Asp Phe Leu Leu Val Thr
    530                 535                 540
Pro His Leu Thr His Ala Lys Thr Phe Leu Arg Thr Leu Val Arg Gly
545                 550                 555                 560
Val Pro Glu Tyr Gly Cys Val Val Asn Leu Arg Lys Thr Val Val Asn
                565                 570                 575
Phe Pro Val Glu Asp Glu Ala Leu Gly Gly Thr Ala Phe Val Gln Met
            580                 585                 590
Pro Ala His Gly Leu Phe Pro Trp Cys Gly Leu Leu Leu Asp Thr Arg
        595                 600                 605
Thr Leu Glu Val Gln Ser Asp Tyr Ser Ser Tyr Ala Arg Thr Ser Ile
    610                 615                 620
Arg Ala Ser Leu Thr Phe Asn Arg Gly Phe Lys Ala Gly Arg Asn Met
625                 630                 635                 640
Arg Arg Lys Leu Phe Gly Val Leu Arg Leu Lys Cys His Ser Leu Phe
                645                 650                 655
Leu Asp Leu Gln Val Asn Ser Leu Gln Thr Val Cys Thr Asn Ile Tyr
            660                 665                 670
Lys Ile Leu Leu Leu Gln Ala Tyr Arg Phe His Ala Cys Val Leu Gln
        675                 680                 685
Leu Pro Phe His Gln Gln Val Trp Lys Asn Pro Thr Phe Phe Leu Arg
    690                 695                 700
Val Ile Ser Asp Thr Ala Ser Leu Cys Tyr Ser Ile Leu Lys Ala Lys
705                 710                 715                 720
Asn Ala Gly Met Ser Leu Gly Ala Lys Gly Ala Ala Gly Pro Leu Pro
                725                 730                 735
Ser Glu Ala Val Gln Trp Leu Cys His Gln Ala Phe Leu Leu Lys Leu
            740                 745                 750
Thr Arg His Arg Val Thr Tyr Val Pro Leu Leu Gly Ser Leu Arg Thr
        755                 760                 765
```

```
Ala Gln Thr Gln Leu Ser Arg Lys Leu Pro Gly Thr Thr Leu Thr Ala
        770                 775                 780

Leu Glu Ala Ala Ala Asn Pro Ala Leu Pro Ser Asp Phe Lys Thr Ile
785                 790                 795                 800

Leu Asp

<210> SEQ ID NO 12
<211> LENGTH: 814
<212> TYPE: PRT
<213> ORGANISM: Arabidopsis thaliana

<400> SEQUENCE: 12

Phe Lys Phe Gly Leu Ser Glu Thr Tyr Ser Val Ile Pro Pro Asn His
1               5                   10                  15

Ile Leu Lys Thr Leu Arg Pro Asn Cys Ser Asp Ser Lys Leu Leu Met
            20                  25                  30

Asn His Ile Phe Gly Glu Val Asn Val Trp Ser Thr Thr Pro Ser His
        35                  40                  45

Gly Lys Gly Asn Cys Pro Ser Gly Ser Ile Cys Leu Tyr His Ser Leu
    50                  55                  60

Leu Lys Ser Leu Lys Asn Leu Ile Gly Lys Thr Lys Ser Ser His Leu
65                  70                  75                  80

Lys Met Leu Leu Asp Lys His Cys Pro Val Leu Leu Gln Glu Asp
                85                  90                  95

Ala Leu Lys Ser Gly Thr Thr Ser Gln Ser Ser Arg Arg Gln Lys Ala
                100                 105                 110

Asp Lys Leu Pro His Gly Ser Ser Ser Gln Thr Gly Lys Pro Lys
            115                 120                 125

Cys Pro Ser Val Glu Glu Arg Lys Leu Tyr Cys Thr Asn Asp Gln Val
130                 135                 140

Val Ser Phe Ile Trp Ala Ile Cys Arg Tyr Ile Val Pro Glu Ser Leu
145                 150                 155                 160

Leu Gly Thr Thr His Gln Met Arg Val Leu Arg Lys Asn Ile Ala Trp
                165                 170                 175

Phe Val Ser Arg Arg Asn Glu Lys Cys Thr Val Asn Gln Phe Leu
            180                 185                 190

His Lys Val Lys Pro Ser Asp Phe Pro Phe Ala Arg Lys Glu Leu
        195                 200                 205

Cys Cys Met Val Asn Gly His Glu Leu Gln Ser Glu Ser Ile Arg Ser
210                 215                 220

Thr Gln Gln Met Leu Cys Thr Lys Trp Ile Ser Trp Leu Phe Leu Glu
225                 230                 235                 240

Ile Val Lys Lys Leu Val His Phe Asn Phe Tyr Ala Thr Glu Ser Gln
                245                 250                 255

Gly Gly Arg Leu Asn Ile Tyr Tyr Tyr Arg Lys Arg Ser Trp Glu Arg
            260                 265                 270

Leu Ile Ser Lys Glu Ile Ser Lys Ala Leu Asp Gly Tyr Val Leu Val
        275                 280                 285

Asp Asp Ala Glu Ala Glu Ser Ser Arg Lys Lys Leu Ser Lys Phe Arg
    290                 295                 300

Phe Leu Pro Lys Ala Asn Gly Val Arg Met Val Leu Asp Phe Ser Ser
305                 310                 315                 320

Ser Ser Arg Ser Gln Ser Leu Arg Asp Thr His Ala Val Leu Lys Asp
                325                 330                 335

Ile Gln Leu Lys Glu Pro Asp Val Leu Gly Ser Ser Val Phe Asp His
```

```
                    340             345             350
Asp Asp Phe Tyr Arg Asn Leu Cys Pro Tyr Leu Ile His Leu Arg Ser
            355                 360                 365
Gln Ser Gly Glu Leu Pro Pro Leu Tyr Phe Val Val Ala Asp Val Phe
            370                 375                 380
Lys Ala Phe Asp Ser Val Asp Gln Gly Lys Leu Leu His Val Ile Gln
385                 390                 395                 400
Ser Phe Leu Lys Asp Glu Tyr Ile Leu Asn Arg Cys Arg Leu Val Cys
                405                 410                 415
Cys Gly Lys Arg Ser Asn Trp Val Asn Lys Ile Leu Val Ser Ser Asp
            420                 425                 430
Lys Asn Ser Asn Phe Ser Arg Phe Thr Ser Thr Val Pro Tyr Asn Ala
            435                 440                 445
Leu Gln Ser Ile Val Val Asp Lys Gly Glu Asn His Arg Val Arg Lys
            450                 455                 460
Lys Asp Leu Met Val Trp Ile Gly Asn Met Leu Lys Asn Asn Met Leu
465                 470                 475                 480
Gln Leu Asp Lys Ser Phe Tyr Val Gln Ile Ala Gly Ile Pro Gln Gly
                485                 490                 495
His Arg Leu Ser Ser Leu Leu Cys Cys Phe Tyr Tyr Gly His Leu Glu
            500                 505                 510
Arg Thr Leu Ile Tyr Pro Phe Leu Glu Glu Ala Ser Lys Asp Val Ser
            515                 520                 525
Ser Lys Glu Cys Ser Arg Glu Glu Leu Ile Ile Pro Thr Ser Tyr
            530                 535                 540
Lys Leu Leu Arg Phe Ile Asp Asp Tyr Leu Phe Val Ser Thr Ser Arg
545                 550                 555                 560
Asp Gln Ala Ser Ser Phe Tyr His Arg Leu Lys His Gly Phe Lys Asp
                565                 570                 575
Tyr Asn Cys Phe Met Asn Glu Thr Lys Phe Cys Ile Asn Phe Glu Asp
            580                 585                 590
Lys Glu Glu His Arg Cys Ser Ser Asn Arg Met Phe Val Gly Asp Asn
            595                 600                 605
Gly Val Pro Phe Val Arg Trp Thr Gly Leu Leu Ile Asn Ser Arg Thr
            610                 615                 620
Phe Glu Val Gln Val Asp Tyr Thr Arg Tyr Leu Ser Gly His Ile Ser
625                 630                 635                 640
Ser Thr Phe Ser Val Ala Trp Gln Asn Lys Pro Val Arg Asn Leu Arg
                645                 650                 655
Gln Lys Leu Cys Tyr Phe Leu Val Pro Lys Cys His Pro Ile Leu Phe
            660                 665                 670
Asp Ser Asn Ile Asn Ser Gly Glu Ile Val Arg Leu Asn Ile Tyr Gln
            675                 680                 685
Ile Phe Leu Leu Ala Ala Met Lys Phe His Cys Tyr Val Tyr Glu Val
            690                 695                 700
Ser Arg Phe Trp Lys Leu His Pro Gln Thr Leu Phe Lys Phe Ile Thr
705                 710                 715                 720
Ile Ser Val Arg Tyr Met Phe Arg Leu Ile Asn Arg Arg Val Arg Arg
                725                 730                 735
Ile Asn Thr Gly Ser Ser Phe Arg Pro Val Leu Lys Leu Tyr Lys Glu
            740                 745                 750
Glu Val Ile Trp Leu Gly Leu Asp Ala Tyr Ile Gln Val Leu Lys Lys
            755                 760                 765
```

```
Lys Asn Ser Arg Tyr Arg Met Leu Leu Ile Tyr Leu Lys Ser Ala Leu
            770                 775                 780

Ser Lys His Ser Leu Ser Gln Gln Leu Ser Ser Glu Leu Arg Tyr Ala
785                 790                 795                 800

Thr Asp Arg Ser Asn Ser Ser Ser Leu Trp Lys Leu Asn Tyr
                805                 810

<210> SEQ ID NO 13
<211> LENGTH: 698
<212> TYPE: PRT
<213> ORGANISM: Saccharomyces cerevisiae

<400> SEQUENCE: 13

Phe Leu His Lys Leu Asn Ile Asn Ser Ser Phe Pro Tyr Ser
1               5                   10                  15

Lys Ile Leu Pro Ser Ser Ser Ile Lys Lys Leu Thr Asp Leu Arg
                20                  25                  30

Glu Ala Ile Phe Pro Thr Asn Leu Val Lys Ile Pro Gln Arg Leu Lys
                35                  40                  45

Val Arg Ile Asn Leu Thr Leu Gln Lys Leu Leu Lys Arg His Lys Arg
50                  55                  60

Leu Asn Tyr Val Ser Ile Leu Asn Ser Ile Cys Pro Pro Leu Glu Gly
65                  70                  75                  80

Thr Val Leu Asp Leu Ser His Leu Ser Arg Gln Ser Pro Lys Glu Arg
                85                  90                  95

Val Leu Lys Phe Ile Ile Val Ile Leu Gln Lys Leu Leu Pro Gln Glu
                100                 105                 110

Met Phe Gly Ser Lys Lys Asn Lys Gly Lys Ile Ile Lys Asn Leu Asn
                115                 120                 125

Leu Leu Leu Ser Leu Pro Leu Asn Gly Tyr Leu Pro Phe Asp Ser Leu
130                 135                 140

Leu Lys Lys Leu Arg Leu Lys Asp Phe Arg Trp Leu Phe Ile Ser Asp
145                 150                 155                 160

Ile Trp Phe Thr Lys His Asn Phe Glu Asn Leu Asn Gln Leu Ala Ile
                165                 170                 175

Cys Phe Ile Ser Trp Leu Phe Arg Gln Leu Ile Pro Lys Ile Ile Gln
                180                 185                 190

Thr Phe Phe Tyr Cys Thr Glu Ile Ser Ser Thr Val Thr Ile Val Tyr
                195                 200                 205

Phe Arg His Asp Thr Trp Asn Lys Leu Ile Thr Pro Phe Ile Val Glu
210                 215                 220

Tyr Phe Lys Thr Tyr Leu Val Glu Asn Asn Val Cys Arg Asn His Asn
225                 230                 235                 240

Ser Tyr Thr Leu Ser Asn Phe Asn His Ser Lys Met Arg Ile Ile Pro
                245                 250                 255

Lys Lys Ser Asn Asn Glu Phe Arg Ile Ile Ala Ile Pro Cys Arg Gly
                260                 265                 270

Ala Asp Glu Glu Glu Phe Thr Ile Tyr Lys Glu Asn His Lys Asn Ala
                275                 280                 285

Ile Gln Pro Thr Gln Lys Ile Leu Glu Tyr Leu Arg Asn Lys Arg Pro
                290                 295                 300

Thr Ser Phe Thr Lys Ile Tyr Ser Pro Thr Gln Ile Ala Asp Arg Ile
305                 310                 315                 320

Lys Glu Phe Lys Gln Arg Leu Leu Lys Lys Phe Asn Asn Val Leu Pro
                325                 330                 335
```

-continued

```
Glu Leu Tyr Phe Met Lys Phe Asp Val Lys Ser Cys Tyr Asp Ser Ile
                340                 345                 350

Pro Arg Met Glu Cys Met Arg Ile Leu Lys Asp Ala Leu Lys Asn Glu
        355                 360                 365

Asn Gly Phe Phe Val Arg Ser Gln Tyr Phe Asn Thr Asn Thr Gly
    370                 375                 380

Val Leu Lys Leu Phe Asn Val Val Asn Ala Ser Arg Val Pro Lys Pro
385                 390                 395                 400

Tyr Glu Leu Tyr Ile Asp Asn Val Arg Thr Val His Leu Ser Asn Gln
                405                 410                 415

Asp Val Ile Asn Val Val Glu Met Glu Ile Phe Lys Thr Ala Leu Trp
            420                 425                 430

Val Glu Asp Lys Cys Tyr Ile Arg Glu Asp Gly Leu Phe Gln Gly Ser
        435                 440                 445

Ser Leu Ser Ala Pro Ile Val Asp Leu Val Tyr Asp Asp Leu Leu Glu
    450                 455                 460

Phe Tyr Ser Glu Phe Lys Ala Ser Pro Ser Gln Asp Thr Leu Ile Leu
465                 470                 475                 480

Lys Leu Ala Asp Asp Phe Leu Ile Ile Ser Thr Asp Gln Gln Val
                485                 490                 495

Ile Asn Ile Lys Lys Leu Ala Met Gly Gly Phe Gln Lys Tyr Asn Ala
            500                 505                 510

Lys Ala Asn Arg Asp Lys Ile Leu Ala Val Ser Ser Gln Ser Asp Asp
        515                 520                 525

Asp Thr Val Ile Gln Phe Cys Ala Met His Ile Phe Val Lys Glu Leu
    530                 535                 540

Glu Val Trp Lys His Ser Ser Thr Met Asn Asn Phe His Ile Arg Ser
545                 550                 555                 560

Lys Ser Ser Lys Gly Ile Phe Arg Ser Leu Ile Ala Leu Phe Asn Thr
                565                 570                 575

Arg Ile Ser Tyr Lys Thr Ile Asp Thr Asn Leu Asn Ser Thr Asn Thr
            580                 585                 590

Val Leu Met Gln Ile Asp His Val Val Lys Asn Ile Ser Glu Cys Tyr
        595                 600                 605

Lys Ser Ala Phe Lys Asp Leu Ser Ile Asn Val Thr Gln Asn Met Gln
    610                 615                 620

Phe His Ser Phe Leu Gln Arg Ile Ile Glu Met Thr Val Ser Gly Cys
625                 630                 635                 640

Pro Ile Thr Lys Cys Asp Pro Leu Ile Glu Tyr Glu Val Arg Phe Thr
                645                 650                 655

Ile Leu Asn Gly Phe Leu Glu Ser Leu Ser Ser Asn Thr Ser Lys Phe
            660                 665                 670

Lys Asp Asn Ile Ile Leu Leu Arg Lys Glu Ile Gln His Leu Gln Ala
        675                 680                 685

Tyr Ile Tyr Ile Tyr Ile His Ile Val Asn
    690                 695

<210> SEQ ID NO 14
<211> LENGTH: 751
<212> TYPE: PRT
<213> ORGANISM: Schizosaccharomyces pombe

<400> SEQUENCE: 14

Phe Lys Gln Asp Leu Tyr Phe Asn Leu His Ser Ile Cys Asp Arg Asn
1               5                   10                  15
```

-continued

```
Thr Val His Met Trp Leu Gln Trp Ile Phe Pro Arg Gln Phe Gly Leu
             20                  25                  30
Ile Asn Ala Phe Gln Val Lys Gln Leu His Lys Val Ile Pro Leu Val
             35                  40                  45
Ser Gln Ser Thr Val Val Pro Lys Arg Leu Leu Lys Val Tyr Pro Leu
 50                  55                  60
Ile Glu Gln Thr Ala Lys Arg Leu His Arg Ile Ser Leu Ser Lys Val
 65                  70                  75                  80
Tyr Asn His Tyr Cys Pro Tyr Ile Asp Thr His Asp Asp Glu Lys Ile
                 85                  90                  95
Leu Ser Tyr Ser Leu Lys Pro Asn Gln Val Phe Ala Phe Leu Arg Ser
            100                 105                 110
Ile Leu Val Arg Val Phe Pro Lys Leu Ile Trp Gly Asn Gln Arg Ile
            115                 120                 125
Phe Glu Ile Ile Leu Lys Asp Leu Glu Thr Phe Leu Lys Leu Ser Arg
130                 135                 140
Tyr Glu Ser Phe Ser Leu His Tyr Leu Met Ser Asn Ile Lys Ile Ser
145                 150                 155                 160
Glu Ile Glu Trp Leu Val Leu Gly Lys Arg Ser Asn Ala Lys Met Cys
                165                 170                 175
Leu Ser Asp Phe Glu Lys Arg Lys Gln Ile Phe Ala Glu Phe Ile Tyr
            180                 185                 190
Trp Leu Tyr Asn Ser Phe Ile Ile Pro Ile Leu Gln Ser Phe Phe Tyr
            195                 200                 205
Ile Thr Glu Ser Ser Asp Leu Arg Asn Arg Thr Val Tyr Phe Arg Lys
            210                 215                 220
Asp Ile Trp Lys Leu Leu Cys Arg Pro Phe Ile Thr Ser Met Lys Met
225                 230                 235                 240
Glu Ala Phe Glu Lys Ile Asn Glu Asn Val Arg Met Asp Thr Gln
                245                 250                 255
Lys Thr Thr Leu Pro Pro Ala Val Ile Arg Leu Leu Pro Lys Lys Asn
            260                 265                 270
Thr Phe Arg Leu Ile Thr Asn Leu Arg Lys Arg Phe Leu Ile Lys Met
            275                 280                 285
Gly Ser Asn Lys Lys Met Leu Val Ser Thr Asn Gln Thr Leu Arg Pro
290                 295                 300
Val Ala Ser Ile Leu Lys His Leu Ile Asn Glu Glu Ser Ser Gly Ile
305                 310                 315                 320
Pro Phe Asn Leu Glu Val Tyr Met Lys Leu Leu Thr Phe Lys Lys Asp
                325                 330                 335
Leu Leu Lys His Arg Met Phe Gly Arg Lys Lys Tyr Phe Val Arg Ile
            340                 345                 350
Asp Ile Lys Ser Cys Tyr Asp Arg Ile Lys Gln Asp Leu Met Phe Arg
            355                 360                 365
Ile Val Lys Lys Lys Leu Lys Asp Pro Glu Phe Val Ile Arg Lys Tyr
            370                 375                 380
Ala Thr Ile His Ala Thr Ser Asp Arg Ala Thr Lys Asn Phe Val Ser
385                 390                 395                 400
Glu Ala Phe Ser Tyr Phe Asp Met Val Pro Phe Glu Lys Val Val Gln
                405                 410                 415
Leu Leu Ser Met Lys Thr Ser Asp Thr Leu Phe Val Asp Phe Val Asp
            420                 425                 430
Tyr Trp Thr Lys Ser Ser Ser Glu Ile Phe Lys Met Leu Lys Glu His
            435                 440                 445
```

-continued

```
Leu Ser Gly His Ile Val Lys Ile Gly Asn Ser Gln Tyr Leu Gln Lys
    450                 455                 460

Val Gly Ile Pro Gln Gly Ser Ile Leu Ser Ser Phe Leu Cys His Phe
465                 470                 475                 480

Tyr Met Glu Asp Leu Ile Asp Glu Tyr Leu Ser Phe Thr Lys Lys Lys
                485                 490                 495

Gly Ser Val Leu Leu Arg Val Val Asp Asp Phe Leu Phe Ile Thr Val
            500                 505                 510

Asn Lys Lys Asp Ala Lys Lys Phe Leu Asn Leu Ser Leu Arg Gly Phe
        515                 520                 525

Glu Lys His Asn Phe Ser Thr Ser Leu Glu Lys Thr Val Ile Asn Phe
530                 535                 540

Glu Asn Ser Asn Gly Ile Ile Asn Asn Thr Phe Phe Asn Glu Ser Lys
545                 550                 555                 560

Lys Arg Met Pro Phe Phe Gly Phe Ser Val Asn Met Arg Ser Leu Asp
                565                 570                 575

Thr Leu Leu Ala Cys Pro Lys Ile Asp Glu Ala Leu Phe Asn Ser Thr
            580                 585                 590

Ser Val Glu Leu Thr Lys His Met Gly Lys Ser Phe Phe Tyr Lys Ile
        595                 600                 605

Leu Arg Ser Ser Leu Ala Ser Phe Ala Gln Val Phe Ile Asp Ile Thr
610                 615                 620

His Asn Ser Lys Phe Asn Ser Cys Cys Asn Ile Tyr Arg Leu Gly Tyr
625                 630                 635                 640

Ser Met Cys Met Arg Ala Gln Ala Tyr Leu Lys Arg Met Lys Asp Ile
                645                 650                 655

Phe Ile Pro Gln Arg Met Phe Ile Thr Asp Leu Leu Asn Val Ile Gly
            660                 665                 670

Arg Lys Ile Trp Lys Lys Leu Ala Glu Ile Leu Gly Tyr Thr Ser Arg
        675                 680                 685

Arg Phe Leu Ser Ser Ala Glu Val Lys Trp Leu Phe Cys Leu Gly Met
690                 695                 700

Arg Asp Gly Leu Lys Pro Ser Phe Lys Tyr His Pro Cys Phe Glu Gln
705                 710                 715                 720

Leu Ile Tyr Gln Phe Gln Ser Leu Thr Asp Leu Ile Lys Pro Leu Arg
                725                 730                 735

Pro Val Leu Arg Gln Val Leu Phe Leu His Arg Arg Ile Ala Asp
            740                 745                 750

<210> SEQ ID NO 15
<211> LENGTH: 877
<212> TYPE: PRT
<213> ORGANISM: Tetrahymena thermophila

<400> SEQUENCE: 15

Val Phe Lys Ser Ser Phe Phe Asn Tyr Ser Glu Ile Lys Lys Gly Phe
1               5                   10                  15

Gln Phe Lys Val Ile Gln Glu Lys Leu Gln Gly Arg Gln Phe Ile Asn
                20                  25                  30

Ser Asp Lys Ile Lys Pro Asp His Pro Gln Thr Ile Ile Lys Lys Thr
            35                  40                  45

Leu Leu Lys Glu Tyr Gln Ser Lys Asn Phe Ser Cys Gln Glu Glu Arg
        50                  55                  60

Asp Leu Phe Leu Glu Phe Thr Glu Lys Ile Val Gln Asn Phe His Asn
65                  70                  75                  80
```

-continued

```
Ile Asn Phe Asn Tyr Leu Leu Lys Lys Phe Cys Lys Leu Pro Glu Asn
                 85                  90                  95
Tyr Gln Ser Leu Lys Ser Gln Val Lys Gln Ile Val Gln Ser Glu Asn
            100                 105                 110
Lys Ala Asn Gln Gln Ser Cys Glu Asn Leu Phe Asn Ser Leu Tyr Asp
        115                 120                 125
Thr Glu Ile Ser Tyr Lys Gln Ile Thr Asn Phe Leu Arg Gln Ile Ile
    130                 135                 140
Gln Asn Cys Val Pro Asn Gln Leu Leu Gly Lys Lys Asn Phe Lys Val
145                 150                 155                 160
Phe Leu Glu Lys Leu Tyr Glu Phe Val Gln Met Lys Arg Phe Glu Asn
                165                 170                 175
Gln Lys Val Leu Asp Tyr Ile Cys Phe Met Asp Val Phe Asp Val Glu
            180                 185                 190
Trp Phe Val Asp Leu Lys Asn Gln Lys Phe Thr Gln Lys Arg Lys Tyr
        195                 200                 205
Ile Ser Asp Lys Arg Lys Ile Leu Gly Asp Leu Ile Val Phe Ile Ile
    210                 215                 220
Asn Lys Ile Val Ile Pro Val Leu Arg Tyr Asn Phe Tyr Ile Thr Glu
225                 230                 235                 240
Lys His Lys Glu Gly Ser Gln Ile Phe Tyr Tyr Arg Lys Pro Ile Trp
                245                 250                 255
Lys Leu Val Ser Lys Leu Thr Ile Val Lys Leu Glu Glu Asn Leu
            260                 265                 270
Glu Lys Val Glu Glu Lys Leu Ile Pro Glu Asp Ser Phe Gln Lys Tyr
        275                 280                 285
Pro Gln Gly Lys Leu Arg Ile Ile Pro Lys Lys Gly Ser Phe Arg Pro
    290                 295                 300
Ile Met Thr Phe Leu Arg Lys Asp Lys Gln Lys Asn Ile Lys Leu Asn
305                 310                 315                 320
Leu Asn Gln Ile Leu Met Asp Ser Gln Leu Val Phe Arg Asn Leu Lys
                325                 330                 335
Asp Met Leu Gly Gln Lys Ile Gly Tyr Ser Val Phe Asp Asn Lys Gln
            340                 345                 350
Ile Ser Glu Lys Phe Ala Gln Phe Ile Glu Lys Trp Lys Asn Lys Gly
        355                 360                 365
Arg Pro Gln Leu Tyr Tyr Val Thr Leu Asp Ile Lys Lys Cys Tyr Asp
    370                 375                 380
Ser Ile Asp Gln Met Lys Leu Leu Asn Phe Phe Asn Gln Ser Asp Leu
385                 390                 395                 400
Ile Gln Asp Thr Tyr Phe Ile Asn Lys Tyr Leu Leu Phe Gln Arg Asn
                405                 410                 415
Lys Arg Pro Leu Leu Gln Ile Gln Gln Thr Asn Asn Leu Asn Ser Ala
            420                 425                 430
Met Glu Ile Glu Glu Glu Lys Ile Asn Lys Pro Phe Lys Met Asp
        435                 440                 445
Asn Ile Asn Phe Pro Tyr Tyr Phe Asn Leu Lys Glu Arg Gln Ile Ala
    450                 455                 460
Tyr Ser Leu Tyr Asp Asp Asp Gln Ile Leu Gln Lys Gly Phe Lys
465                 470                 475                 480
Glu Ile Gln Ser Asp Asp Arg Pro Phe Ile Val Ile Asn Gln Asp Lys
                485                 490                 495
Pro Arg Cys Ile Thr Lys Asp Ile Ile His Asn His Leu Lys His Ile
```

```
                   500                 505                 510
Ser Gln Tyr Asn Val Ile Ser Phe Asn Lys Val Lys Phe Arg Gln Lys
            515                 520                 525

Arg Gly Ile Pro Gln Gly Leu Asn Ile Ser Gly Val Leu Cys Ser Phe
        530                 535                 540

Tyr Phe Gly Lys Leu Glu Glu Glu Tyr Thr Gln Phe Leu Lys Asn Ala
545                 550                 555                 560

Glu Gln Val Asn Gly Ser Ile Asn Leu Leu Met Arg Leu Thr Asp Asp
                565                 570                 575

Tyr Leu Phe Ile Ser Asp Ser Gln Gln Asn Ala Leu Asn Leu Ile Val
            580                 585                 590

Gln Leu Gln Asn Cys Ala Asn Asn Gly Phe Met Phe Asn Asp Gln
        595                 600                 605

Lys Ile Thr Thr Asn Phe Gln Phe Pro Gln Glu Asp Tyr Asn Leu Glu
        610                 615                 620

His Phe Lys Ile Ser Val Gln Asn Glu Cys Gln Trp Ile Gly Lys Ser
625                 630                 635                 640

Ile Asp Met Asn Thr Leu Glu Ile Lys Ser Ile Gln Lys Gln Thr Gln
                645                 650                 655

Gln Glu Ile Asn Gln Thr Ile Asn Val Ala Ile Ser Ile Lys Asn Leu
            660                 665                 670

Lys Ser Gln Leu Lys Asn Lys Leu Arg Ser Leu Phe Leu Asn Gln Leu
        675                 680                 685

Ile Asp Tyr Phe Asn Pro Asn Ile Asn Ser Phe Glu Gly Leu Cys Arg
        690                 695                 700

Gln Leu Tyr His His Ser Lys Ala Thr Val Met Lys Phe Tyr Pro Phe
705                 710                 715                 720

Met Thr Lys Leu Phe Gln Ile Asp Leu Lys Lys Ser Lys Gln Tyr Ser
                725                 730                 735

Val Gln Tyr Gly Lys Glu Asn Thr Asn Glu Asn Phe Leu Lys Asp Ile
            740                 745                 750

Leu Tyr Tyr Thr Val Glu Asp Val Cys Lys Ile Leu Cys Tyr Leu Gln
        755                 760                 765

Phe Glu Asp Glu Ile Asn Ser Asn Ile Lys Glu Ile Phe Lys Asn Leu
        770                 775                 780

Tyr Ser Trp Ile Met Trp Asp Ile Ile Val Ser Tyr Leu Lys Lys Lys
785                 790                 795                 800

Lys Gln Phe Lys Gly Tyr Leu Asn Lys Leu Leu Gln Lys Ile Arg Lys
                805                 810                 815

Ser Arg Phe Phe Tyr Leu Lys Glu Gly Cys Lys Ser Leu Gln Leu Ile
            820                 825                 830

Leu Ser Gln Gln Lys Tyr Gln Leu Asn Lys Lys Glu Leu Glu Ala Ile
        835                 840                 845

Glu Phe Ile Asp Leu Asn Asn Leu Ile Gln Asp Ile Lys Thr Leu Ile
        850                 855                 860

Pro Lys Ile Ser Ala Lys Ser Asn Gln Gln Asn Thr Asn
865                 870                 875

<210> SEQ ID NO 16
<211> LENGTH: 790
<212> TYPE: PRT
<213> ORGANISM: Euplotes aediculatus

<400> SEQUENCE: 16

Phe Tyr Cys Thr His Phe Asn Arg Asn Asn Gln Phe Phe Lys Lys His
```

-continued

```
1               5                   10                  15
Glu Phe Val Ser Asn Lys Asn Asn Ile Ser Ala Met Asp Arg Ala Gln
                20                  25                  30

Thr Ile Phe Thr Asn Ile Phe Arg Phe Asn Arg Ile Arg Lys Lys Leu
                35                  40                  45

Lys Asp Lys Val Ile Glu Lys Ile Ala Tyr Met Leu Glu Lys Val Lys
 50                  55                  60

Asp Phe Asn Phe Asn Tyr Tyr Leu Thr Lys Ser Cys Pro Leu Pro Glu
 65                  70                  75                  80

Asn Trp Arg Glu Arg Lys Gln Lys Ile Glu Asn Leu Ile Asn Lys Thr
                85                  90                  95

Arg Glu Glu Lys Ser Lys Tyr Tyr Glu Glu Leu Phe Ser Tyr Thr Thr
                100                 105                 110

Asp Asn Lys Cys Val Thr Gln Phe Ile Asn Glu Phe Phe Tyr Asn Ile
                115                 120                 125

Leu Pro Lys Asp Phe Leu Thr Gly Arg Asn Arg Lys Asn Phe Gln Lys
                130                 135                 140

Lys Val Lys Lys Tyr Val Glu Leu Asn Lys His Glu Leu Ile His Lys
145                 150                 155                 160

Asn Leu Leu Glu Lys Ile Asn Thr Arg Glu Ile Ser Trp Met Gln
                165                 170                 175

Val Glu Thr Ser Ala Lys His Phe Tyr Tyr Phe Asp His Glu Asn Ile
                180                 185                 190

Tyr Val Leu Trp Lys Leu Leu Arg Trp Ile Phe Glu Asp Leu Val Val
                195                 200                 205

Ser Leu Ile Arg Cys Phe Phe Tyr Val Thr Glu Gln Gln Lys Ser Tyr
                210                 215                 220

Ser Lys Thr Tyr Tyr Tyr Arg Lys Asn Ile Trp Asp Val Ile Met Lys
225                 230                 235                 240

Met Ser Ile Ala Asp Leu Lys Lys Glu Thr Leu Ala Glu Val Gln Glu
                245                 250                 255

Lys Glu Val Glu Glu Trp Lys Lys Ser Leu Gly Phe Ala Pro Gly Lys
                260                 265                 270

Leu Arg Leu Ile Pro Lys Lys Thr Thr Phe Arg Pro Ile Met Thr Phe
                275                 280                 285

Asn Lys Lys Ile Val Asn Ser Asp Arg Lys Thr Thr Lys Leu Thr Thr
                290                 295                 300

Asn Thr Lys Leu Leu Asn Ser His Leu Met Leu Lys Thr Leu Lys Asn
305                 310                 315                 320

Arg Met Phe Lys Asp Pro Phe Gly Phe Ala Val Phe Asn Tyr Asp Asp
                325                 330                 335

Val Met Lys Lys Tyr Glu Glu Phe Val Cys Lys Trp Lys Gln Val Gly
                340                 345                 350

Gln Pro Lys Leu Phe Phe Ala Thr Met Asp Ile Glu Lys Cys Tyr Asp
                355                 360                 365

Ser Val Asn Arg Glu Lys Leu Ser Thr Phe Leu Lys Thr Thr Lys Leu
                370                 375                 380

Leu Ser Ser Asp Phe Trp Ile Met Thr Ala Gln Ile Leu Lys Arg Lys
385                 390                 395                 400

Asn Asn Ile Val Ile Asp Ser Lys Asn Phe Arg Lys Lys Glu Met Lys
                405                 410                 415

Asp Tyr Phe Arg Gln Lys Phe Gln Lys Ile Ala Leu Glu Gly Gly Gln
                420                 425                 430
```

-continued

```
Tyr Pro Thr Leu Phe Ser Val Leu Glu Asn Glu Gln Asn Asp Leu Asn
        435                 440                 445

Ala Lys Lys Thr Leu Ile Val Glu Ala Lys Gln Arg Asn Tyr Phe Lys
450                 455                 460

Lys Asp Asn Leu Leu Gln Pro Val Ile Asn Ile Cys Gln Tyr Asn Tyr
465                 470                 475                 480

Ile Asn Phe Asn Gly Lys Phe Tyr Lys Gln Thr Lys Gly Ile Pro Gln
                485                 490                 495

Gly Leu Cys Val Ser Ser Ile Leu Ser Ser Phe Tyr Tyr Ala Thr Leu
            500                 505                 510

Glu Glu Ser Ser Leu Gly Phe Leu Arg Asp Ser Met Asn Pro Glu
515                 520                 525

Asn Pro Asn Val Asn Leu Leu Met Arg Leu Thr Asp Asp Tyr Leu Leu
530                 535                 540

Ile Thr Thr Gln Glu Asn Asn Ala Val Leu Phe Ile Glu Lys Leu Ile
545                 550                 555                 560

Asn Val Ser Arg Glu Asn Gly Phe Lys Phe Asn Met Lys Lys Leu Gln
                565                 570                 575

Thr Ser Phe Pro Leu Ser Pro Ser Lys Phe Ala Lys Tyr Gly Met Asp
            580                 585                 590

Ser Val Glu Glu Gln Asn Ile Val Gln Asp Tyr Cys Asp Trp Ile Gly
            595                 600                 605

Ile Ser Ile Asp Met Lys Thr Leu Ala Leu Met Pro Asn Ile Asn Leu
610                 615                 620

Arg Ile Glu Gly Ile Leu Cys Thr Leu Asn Leu Asn Met Gln Thr Lys
625                 630                 635                 640

Lys Ala Ser Met Trp Leu Lys Lys Leu Lys Ser Phe Leu Met Asn
                645                 650                 655

Asn Ile Thr His Tyr Phe Arg Lys Thr Ile Thr Thr Glu Asp Phe Ala
            660                 665                 670

Asn Lys Thr Leu Asn Lys Leu Phe Ile Ser Gly Gly Tyr Lys Tyr Met
            675                 680                 685

Gln Cys Ala Lys Glu Tyr Lys Asp His Phe Lys Lys Asn Leu Ala Met
690                 695                 700

Ser Ser Met Ile Asp Leu Glu Val Ser Lys Ile Ile Tyr Ser Val Thr
705                 710                 715                 720

Arg Ala Phe Phe Lys Tyr Leu Val Cys Asn Ile Lys Asp Thr Ile Phe
                725                 730                 735

Gly Glu Glu His Tyr Pro Asp Phe Phe Leu Ser Thr Leu His Phe
            740                 745                 750

Ile Glu Ile Phe Ser Thr Lys Lys Tyr Ile Phe Asn Arg Val Cys Met
            755                 760                 765

Ile Leu Lys Ala Lys Glu Ala Lys Leu Lys Ser Asp Gln Cys Gln Ser
770                 775                 780

Leu Ile Gln Tyr Asp Ala
785                 790
```

<210> SEQ ID NO 17
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 17
aagccgtcga gcagagtc          18

```
<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
gtgtgacctg acctgacc                                                       18

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
cugaccugac ttcggtcagg t                                                   21

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 20
cugaccugtt cgcaggt                                                        17

<210> SEQ ID NO 21
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 21
cugaccuttc gaggt                                                          15
```

METHOD FOR IDENTIFYING A COMPOUND THAT MODULATES TELOMERASE ACTIVITY

INTRODUCTION

This application is a continuation-in-part of PCT/US2008/080604, filed Oct. 21, 2008, which claims benefit of priority to U.S. Provisional Patent Application Ser. No. 61/090,726, filed Aug. 21, 2008, and Ser. No. 60/981,548, filed Oct. 22, 2007, the contents of which are incorporated herein by reference in their entireties.

BACKGROUND OF THE INVENTION

Any organism with linear chromosomes faces a substantial obstacle in maintaining the terminal sequence of its DNA often referred to as the "end replication problem" (Blackburn (1984) *Annu. Rev. Biochem.* 53:163-194; Cavalier-Smith (1974) *Nature* 250:467-470; Cech & Lingner (1997) *Ciba Found. Symp.* 211:20-34; Lingner, et al. (1995) *Science* 269:1533-1534; Lundblad (1997) *Nat. Med.* 3:1198-1199; Ohki, et al. (2001) *Mol. Cell. Biol.* 21:5753-5766). Eukaryotic cells overcome this problem through the use of a specialized DNA polymerase, called telomerase. Telomerase adds tandem, G-rich, DNA repeats (telomeres) to the 3'-end of linear chromosomes that serve to protect chromosomes from loss of genetic information, chromosome end-to-end fusion, genomic instability and senescence (Autexier & Lue (2006) *Annu. Rev. Biochem.* 75:493-517; Blackburn & Gall (1978) *J. Mol. Biol.* 120:33-53; Chatziantoniou (2001) *Pathol. Oncol. Res.* 7:161-170; Collins (1996) *Curr. Opin. Cell Biol.* 8:374-380; Dong, et al. (2005) *Crit. Rev. Oncol. Hematol.* 54:85-93).

The core telomerase holoenzyme is an RNA-dependent DNA polymerase (TERT) paired with an RNA molecule (TER) that serves as a template for the addition of telomeric sequences (Blackburn (2000) *Nat. Struct. Biol.* 7:847-850; Lamond (1989) *Trends Biochem. Sci.* 14:202-204; Miller & Collins (2002) *Proc. Natl. Acad. Sci. USA* 99:6585-6590; Miller, et al. (2000) *EMBO J.* 19:4412-4422; Shippen-Lentz & Blackburn (1990) *Science* 247:546-552). TERT is composed of four functional domains one of which shares similarities with the HIV reverse transcriptase (RT) in that it contains key signature motifs that are hallmarks of this family of proteins (Autexier & Lue (2006) supra; Bryan, et al. (1998) *Proc. Natl. Acad. Sci. USA* 95:8479-8484; Lee, et al. (2003) *J. Biol. Chem.* 278:52531-52536; Peng, et al. (2001) *Mol. Cell.* 7:1201-1211). The RT domain, which contains the active site of telomerase is thought to be involved in loose associations with the RNA template (Collins & Gandhi (1998) *Proc. Natl. Acad. Sci. USA* 95:8485-8490; Jacobs, et al. (2005) *Protein Sci.* 14:2051-2058). TERT however is unique, when compared to other reverse transcriptases in that it contains two domains N-terminal to the RT domain that are essential for function. These include the far N-terminal domain (TEN), which is the least conserved among phylogenetic groups, but is required for appropriate human, yeast and ciliated protozoa telomerase activity in vitro and telomere maintenance in vivo (Friedman & Cech (1999) *Genes Dev.* 13:2863-2874; Friedman, et al. (2003) *Mol. Biol. Cell* 14:1-13). The TEN domain has both DNA- and RNA-binding properties. DNA-binding facilitates loading of telomerase to the chromosomes while RNA-binding is non-specific and the role of this interaction is unclear (Hammond, et al. (1997) *Mol. Cell. Biol.* 17:296-308; Jacobs, et al. (2006) *Nat. Struct. Mol. Biol.* 13:218-225; Wyatt, et al. (2007) *Mol. Cell. Biol.* 27:3226-3240). A third domain, the telomerase RNA binding domain (TRBD), is located between the TEN and RT domains, and unlike the TEN-domain is highly conserved among phylogenetic groups and is essential for telomerase function both in vitro and in vivo (Lai, et al. (2001) *Mol. Cell. Biol.* 21:990-1000). The TRBD contains key signature motifs (CP- and T-motifs) implicated in RNA recognition and binding and makes extensive contacts with stem I and the TBE of TER, both of which are located upstream of the template (Bryan, et al. (2000) *Mol. Cell.* 6:493-499; Cunningham & Collins (2005) *Mol. Cell. Biol.* 25:4442-4454; Lai, et al. (2002) *Genes Dev.* 16:415-420; Lai, et al. (2001) supra; Miller, et al. (2000) supra; O'Connor, et al. (2005) *J. Biol. Chem.* 280:17533-17539). The TRBD-TER interaction is required for the proper assembly and enzymatic activity of the holoenzyme both in vitro and in vivo, and is thought to play an important role (although indirect) in the faithful addition of multiple, identical telomeric repeats at the ends of chromosomes (Lai, et al. (2002) supra; Lai, et al. (2003) *Mol. Cell.* 11:1673-1683; Lai, et al. (2001) supra).

Unlike TERT, TER varies considerably in size between species. For example, in *Tetrahymena thermophila* TER is only 159 nucleotides long (Greider & Blackburn (1989) *Nature* 337:331-337), while yeast harbors an unusually long TER of 1167 nucleotides (Zappulla & Cech (2004) *Proc. Natl. Acad. Sci. USA* 101:0024-10029). Despite the large differences in size and structure, the core structural elements of TER are conserved among phylogenetic groups, suggesting a common mechanism of telomere replication among organisms (Chen, et al. (2000) *Cell* 100:503-514; Chen & Greider (2003) *Genes Dev.* 17:2747-2752; Chen & Greider (2004) *Trends Biochem. Sci.* 29:183-192; Ly, et al. (2003) *Mol. Cell. Biol.* 23:6849-6856; Theimer & Feigon (2006) *Curr. Opin. Struct. Biol.* 16:307-318). These include the template, which associates loosely with the RT domain, and provides the code for telomere synthesis, and the TBE, which partly regulates telomerase's repeat addition processivity. In *Tetrahymena thermophila*, the TBE is formed by stem II and the flanking single stranded regions, and is located upstream and in close proximity to the template (Lai, et al. (2002) supra; Lai, et al. (2003) supra; Licht & Collins (1999) *Genes Dev.* 13:1116-1125). Low-affinity TERT-binding sites are also found in helix IV and the template recognition element (TRE) of *Tetrahymena thermophila* TER.

TERT function is regulated by a number of proteins, some of which act by direct association with the TERT/TER complex, while others act by regulating access of telomerase to the chromosome end through their association with the telomeric DNA (Aigner, et al. (2002) *Curr. Opin. Genet. Dev.* 12:80-85; Cong, et al. (2002) *Microbiol. Mol. Biol. Rev.* 66:407-425; Dong, et al. (2005) supra; Loayza & de Lange (2004) *Cell* 117:279-280; Smogorzewska & de Lange (2004) *Annu. Rev. Biochem.* 73:177-208; Smogorzewska, et al. (2000) *Mol. Cell. Biol.* 20:1659-1668; Witkin & Collins (2004) *Genes Dev.* 18:1107-1118; Witkin, et al. (2007) *Mol. Cell. Biol.* 27:2074-2083). For example, p65 in the ciliated protozoan *Tetrahymena thermophila* or its homologue p43 in *Euplotes aediculatus*, are integral components of the telomerase holoenzyme (Aigner & Cech (2004) *RNA* 10:1108-1118; Aigner, et al. (2003) *Biochemistry* 42:5736-5747; O'Connor & Collins (2006) *Mol. Cell. Biol.* 26:2029-2036; Prathapam, et al. (2005) *Nat. Struct. Mol. Biol.* 12:252-257; Witkin & Collins (2004) supra; Witkin, et al. (2007) supra). Both p65 and p43 are thought to bind and fold TER, a process required for the proper assembly and full activity of the holoenzyme. In yeast, recruitment and subsequent up regulation of telomerase activity requires the telomerase-associated protein Est1 (Evans & Lundblad (2002) *Genetics* 162:1101-1115; Hughes, et al. (1997) *Ciba Found. Symp.* 211:41-52; Lundblad (2003) *Curr. Biol.* 13:R439-441; Lundblad & Blackburn (1990) *Cell* 60:529-530; Reichenbach, et al. (2003) *Curr. Biol.* 13:568-574; Snow, et al. (2003) *Curr. Biol.* 13:698-704). Est1 binds the RNA component of telomerase, an interaction that facilitates recruitment of the holoenzyme to the eukaryotic chromosome ends via its interaction with the telomere binding protein Cdc13 (Chandra, et al. (2001) *Genes Dev.* 15:404-414; Evans & Lundblad (1999) *Science* 286:117-120; Lustig (2001) *Nat. Struct. Biol.* 8:297-299; Pennock, et al. (2001) *Cell* 104:387-396).

How telomerase and associated regulatory factors physically interact and function with each other to maintain appropriate telomere length is under investigation. Structural and biochemical characterization of these factors, both in isolation and complexed with one another, can be used to determine how the interaction of the TRBD domain with stem I and the TBE of TER facilitate the proper assembly and promote the repeat addition processivity of the holenzyme.

While in vitro and in vivo screening assays have been developed to identify agents which modulate telomerase activity or telomere binding, focus has not been placed on identifying agents with a degree of specificity for particular domains or substrate pockets. See, U.S. Pat. Nos. 7,067,283; 6,906,237; 6,787,133; 6,623,930; 6,517,834; 6,368,789; 6,358,687; 6,342,358; 5,856,096; 5,804,380; and 5,645,986 and US 2006/0040307.

SUMMARY OF THE INVENTION

The present invention features methods for identifying a compound which modulates the activity of telomerase. The methods of this invention involve, (a) designing or screening for a compound which binds to at least one amino acid residue of the TRBD domain, "thumb" domain, "palm" domain, "finger" domain, Motif 2, Motif B', Thumb loop or Thumb helix domains; and (b) testing the compound designed or screened for in (a) for its ability to modulate the activity of telomerase, thereby identifying a compound that modulates the activity of telomerase. In one embodiment, the TRBD domain of telomerase contains the amino acid residues set forth in Table 1. In another embodiment, the "thumb," "palm" and/or "finger" domain contains the amino acid residues set forth in Table 2. In other embodiments, step (a) is carried out in silico. Compounds identified by this method are also embraced by the present invention.

BRIEF DESCRIPTION OF THE DRAWINGS

FIG. 1 shows the structure of telomerase (TERT).

FIGS. 3A-3C show the sequence alignment and surface conservation of *Tribolium castaneum* TERT (TRICA; SEQ ID NO:9) compared with TERTs from various phylogenetic groups including mammals such as mouse (SEQ ID NO:10) and human (SEQ ID NO:11); plants such as *Arabidopsis thaliana* (ARATH; SEQ ID NO:12); fungi such as *Saccharomyces cerevisiae* (YEAST; SEQ ID NO:13) and *Schizosaccharomyces pombe* (SCHPO; SEQ ID NO:14); and protozoa such as *Tetrahymena thermophila* (TETTH; SEQ ID NO:15) and *Euplotes aediculatus* (EUPAE; SEQ ID NO:16) produced by ClustalW2 (Larkin et al. (2007) *Bioinformatics* 23:2947-2948). Conserved residues in key signature motifs are indicated. K210 of helix α10 and polar residues (K406, K416, K418, N423) of the "thumb" domain implicated in direct contacts with the backbone of the DNA substrate are also shown.

DETAILED DESCRIPTION OF THE INVENTION

Figure 1A:
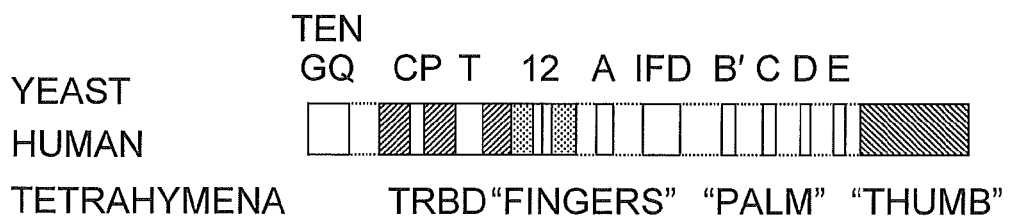
FIG. 1A shows the primary of human, yeast and *Tetrahymena thermophila* TERT showing the functional domains and conserved motifs.

Telomerase, a ribonucleoprotein complex, replicates the linear ends of eukaryotic chromosomes, thus taking care of the "end of replication problem". TERT contains an essential and universally conserved domain (TRBD; FIG. 1) that makes extensive contacts with the RNA (TER) component of the holoenzyme and this interaction facilitates TERT/TER assembly and repeat addition processivity. The TRBD domain is highly conserved among phylogenetic groups and is essential for the function of telomerase. Extensive biochemical and mutagenesis studies have localized TRBD binding to stem I and the TEB, interactions that are thought to be important for the proper assembly and stabilization of the TERT/TER complex as well as the repeat addition processivity of the holoenzyme. The atomic structure of the TRBD domain has now been identified, thereby providing information about TERT/TER binding. The RNA-binding site of TRBD is an extended groove on the surface of the protein that is partly hydrophilic and partly hydrophobic in nature and is formed by the previously identified T- and CP-motifs shown to be important for telomerase function. The size, organization and chemical nature of this groove indicates that the TRBD domain interacts with both double- and single-stranded nucleic acid, possibly stem I or II and the ssRNA that connects them.

In addition to the structure of the TRBD domain, it has now been shown that three highly conserved domains, TRBD, the reverse transcriptase (RT) domain, and the C-terminal extension thought to represent the putative "thumb" domain of TERT, are organized into a ring-like structure (FIG. 1C) that shares common features with retroviral reverse transcriptases, viral RNA polymerases and B-family DNA polymerases. Domain organization places motifs implicated in substrate binding and catalysis in the interior of the ring, which can accommodate seven-to-eight bases of double stranded nucleic acid. Modeling of an RNA/DNA heteroduplex in the interior of this ring reveals a perfect fit between the protein and the nucleic acid substrate and positions the 3'-end of the DNA primer at the active site of the enzyme providing evidence for the formation of an active telomerase elongation complex.

Indeed, as the high-resolution structure of the telomerase catalytic subunit, TERT, in complex with its RNA-templating region, part of the complementary DNA sequence, nucleotides and magnesium ions shows, the RNA-DNA hybrid adopts an A-form helical structure and is docked in the interior cavity of the TERT ring. Protein-nucleic acid associations induce global TERT conformational changes that lead to a decrease in the diameter of the interior cavity of the ring facilitating the formation of a tight telomerase elongation complex. The enzyme, which uses a two-metal binding mechanism for nucleotide association and catalysis, contains two nucleotides at its active site. One of the nucleotides is in position for attack by the 3'-hydroxyl of the incoming DNA primer while the second site appears to hold the nucleotide transiently, allowing for RNA template-dependent selectivity and telomerase processivity.

The TRBD domain, as well as RT and "thumb" domains, are highly conserved domains among phylogenetic groups. As such, these domains serve as ideal candidates for telomerase inhibitors. In this regard, telomerase is an ideal target for treating human diseases or conditions relating to cellular proliferation and senescence.

Accordingly, the present invention relates to the use of the high-resolution structure of *Tetrahymena thermophila* and *Tribolium castaneum* telomerases for the identification of effector molecules that modulate the activity of telomerase. The term "effector" refers to any agonist, antagonist, ligand or other agent that affects the activity of telomerase. Effectors include, but are not limited to, peptides, carbohydrates, nucleic acids, lipids, fatty acids, hormones, organic compounds, and inorganic compounds. The information obtained from the crystal structures herein reveal detailed information which is useful in the design, isolation, screening and determination of potential compounds which modulate the activity of telomerase. Compounds that bind the TRBD domain and, e.g., sterically block TER binding or block RNP assembly act as effective telomerase-specific inhibitors, whereas compounds that mimic or facilitate TER binding or RNP assembly act as effective telomerase-specific activators. Compounds that bind and block the active site or nucleotide binding site can also modulate telomerase activity. Similarly, compounds that interact with one or more amino acid residues of telomerase in direct contact with DNA can block DNA binding and act as effective telomerase-specific inhibitors, whereas compounds that mimic DNA act as effective telomerase-specific activators.

The effector molecules of the invention have a wide variety of uses. For example, it is contemplated that telomerase modulators will be effective therapeutic agents for treatment of human diseases or conditions. Screening for agonists provides for compositions that increase telomerase activity in a cell (including a telomere-dependent replicative capacity, or a partial telomerase activity). Such agonistic compositions provide for methods of immortalizing otherwise normal untransformed cells, including cells which can express useful proteins. Such agonists can also provide for methods of controlling cellular senescence. Conversely, screening for antagonist activity provides for compositions that decrease telomere-dependent replicative capacity, thereby mortalizing otherwise immortal cells, such as cancer cells. Screening for antagonistic activity provides for compositions that decrease telomerase activity, thereby preventing unlimited cell division of cells exhibiting unregulated cell growth, such as cancer cells. In general, the effector molecules of the invention can be used whenever it is desired to increase or decrease telomerase activity in a cell or organism.

Broadly, the methods of the invention involve designing or screening for a test compound which binds to at least one amino acid residue of an essential telomerase domain or pocket disclosed herein; and testing the compound designed or screened for its ability to modulate the activity of telomerase. In certain embodiments, the method of the present invention is carried out using various in silico, in vitro and/or in vivo assays based on detecting interactions between one or more domains or domain residues; or pockets or pocket residues of telomerase and a test compound.

In the context of the present invention, telomerase refers to a family of enzymes which maintain telomere ends by addition of the telomere repeat TTAGGG. Telomerases are described, e.g., by Nakamura, et al. (1997) *Science* 277(5328):955-9 and O'Reilly, et al. (1999)*Curr. Opin. Struct. Biol.* 9(1):56-65. Exemplary telomerase enzymes of use in accordance with the present invention are set forth herein in SEQ ID NOs:1-16 (FIGS. 2A-2B and FIGS. 3A-3C) and full-length sequences for telomerase enzymes are known in the art under GENBANK Accession Nos. AAC39140 (*Tetrahymena thermophila*), NP_197187 (*Arabidopsis thaliana*), NP_937983 (*Homo sapiens*), CAA18391 (*Schizosaccharomyces pombe*), NP_033380 (*Mus musculus*), NP_013422 (*Saccharomyces cerevisiae*), AAC39163 (*Oxytricha trifallax*), CAE75641 (*Euplotes aediculatus*) and NP_001035796 (*Tribolium castaneum*). For the purposes of the present invention, reference to telomerase refers to allelic and synthetic variants of telomerase, as well as fragments of telomerase. Synthetic variants include those which have at least 80%, preferably at least 90%, homology to a telomerase disclosed herein. More preferably, such variants correspond to the sequence of a telomerase provided herein, but have one or more, e.g., from 1 to 10, or from 1 to 5 substitutions, deletions or insertions of amino acids. Fragments of telomerase and variants thereof are preferably between 20 and 500 amino acid residues in length or between 50 and 300 amino acids in length. An exemplary fragment includes the approximately 250 amino acid residues encompassing the TRBD domain of telomerase. Other fragments include the "thumb" domain and the reverse transcriptase domain and its subdomains, i.e., the "finger" and "palm" subdomains. As depicted in FIG. 1A and FIGS. 2A and 2B, the TRBD domain encompasses amino acid residues at or about 254-519 of *T. thermophila* telomerase. As depicted in FIG. 1B and FIGS. 3A-3C, the reverse transcriptase domain encompasses amino acid residues at or about 160-403 of *T. castaneum* telomerase, and the "thumb" domain encompasses amino acid residues at or about 404-596 of *T. castaneum* telomerase. Based upon the amino acid sequence comparisons depicted in FIGS. 2A, 2B, and 3A-3C, suitable domains and fragments of telomerases from other species can be readily obtained based upon the location of equivalent amino acid residues in a telomerase from other species.

The nearly all-helical structure of TRBD provides a nucleic acid binding fold suitable for TER binding. An extended pocket on the surface of the protein, formed by two conserved motifs (CP- and T-motifs) provides TRBD's RNA-binding pocket. The width and the chemical nature of this pocket indicate that it binds both single- and double-stranded RNA, likely stem I and the template boundary element (TBE). As disclosed herein, the structure of *T. thermophila* telomerase identified key amino acid residues involved in RNP assembly of telomerase and the interaction between telomerase TRBD and TER. Accordingly, the present invention embraces a compound, which binds to at least one amino acid residue of the TRBD domain. Essential amino acid residues of this domain are provided in Table 1. The location of these residues in telomerases from other organisms is also listed in Table 1. In particular embodiments, a compound of the invention binds to one or more of the amino acid residues listed in Table 1, thereby modulating the activity of telomerase.

TABLE 1

| Essential TRBD Residues* | Location in telomerases of other organisms | | | | | | | | |
|---|---|---|---|---|---|---|---|---|---|
| | Tt# | Tc† | At# | Sp# | Hs# | Mm# | Sc# | Ot# | Ea# |
| T-motif* | | | | | | | | | |
| F476 | F233 | Y134 | F265 | F185 | F246 | F231 | F186 | F202 | F206 |
| Y477 | Y234 | Y135 | Y266 | Y186 | Y247 | Y232 | Y187 | Y203 | Y207 |
| T479 | T236 | P137 | T268 | T188 | T249 | T234 | T189 | T205 | T209 |
| E480 | E237 | I138 | E269 | E189 | E250 | E235 | E190 | E206 | E210 |
| Y491 | Y248 | I149 | Y280 | F200 | Y261 | Y246 | F200 | Y217 | Y221 |
| R492 | R249 | R150 | R281 | R201 | R262 | R247 | R201 | R218 | R222 |
| K493 | K250 | K151 | K282 | K202 | K263 | K248 | H202 | K219 | L223 |
| W496 | W253 | Y154 | W285 | W205 | W266 | W251 | W205 | W222 | W226 |
| CP-motif* | | | | | | | | | |
| F323 | F80 | L36 | L95 | L55 | Y90 | Y90 | Y58 | F55 | F59 |
| L327 | L84 | K39 | L99 | Y59 | L94 | L94 | L62 | L59 | L63 |
| K328 | K85 | H40 | D100 | N60 | K95 | R95 | N63 | S60 | T64 |
| K329 | K86 | K41 | K101 | H61 | T96 | S96 | S64 | K61 | K65 |
| C331 | C88 | K43 | C103 | C63 | C98 | C98 | C66 | C63 | C67 |
| L333 | L90 | P45 | L108 | — | L100 | — | — | L65 | L69 |
| P334 | P91 | V46 | Q109 | — | R101 | — | — | P66 | P70 |
| QFP-motif* | | | | | | | | | |
| Q375 | Q132 | Q47 | Q158 | Q83 | Q145 | Q130 | R87 | Q103 | C107 |
| I376 | I133 | I48 | V159 | V84 | V146 | V131 | V88 | I104 | V108 |
| L380 | L137 | L52 | I163 | L88 | V150 | L135 | I92 | L108 | I112 |
| I383 | I140 | I55 | I166 | I91 | C153 | C138 | I95 | F111 | F115 |
| I384 | I141 | I56 | C167 | L92 | L154 | L139 | L96 | V112 | F116 |
| C387 | C144 | — | I170 | V95 | L157 | V142 | L99 | V115 | I119 |
| V388 | V145 | — | V171 | F96 | V158 | V143 | L100 | F116 | L120 |
| P389 | P146 | P57 | P172 | P97 | P159 | S144 | P101 | P117 | P121 |
| L392 | L149 | Y60 | L175 | I100 | L162 | L147 | M104 | F120 | F124 |
| L393 | L150 | F61 | L176 | W101 | W163 | W148 | F105 | L121 | L125 |
| N397 | N154 | N66 | Q181 | I106 | N168 | N153 | N110 | N125 | N129 |
| L405 | L162 | V74 | I189 | L114 | T176 | L161 | L118 | M133 | V137 |
| F408 | F165 | I77 | F192 | F117 | F179 | F164 | L121 | F136 | Y140 |
| Y422 | Y179 | L91 | F206 | L131 | L193 | L178 | L135 | L150 | L154 |
| I423 | I180 | H92 | L207 | M132 | T194 | M179 | L136 | L151 | L155 |
| M426 | M183 | Y95 | V210 | I135 | M197 | M182 | L139 | F154 | I158 |
| W433 | W190 | W102 | F217 | W142 | W204 | W189 | W146 | W161 | W165 |
| F434 | F191 | L103 | F218 | L143 | L205 | L190 | L147 | L162 | M166 |

Tt, *Tetrahymena thermophila*;
At, *Arabidopsis thaliana*;
Hs, *Homo sapiens*;
Sp, *Schizosaccharomyces pombe*;
Mm, *Mus musculus*;
Sc, *Saccharomyces cerevisiae*;
Tc, *Tribolium castaneum*;
Ot, *Oxytricha trifallax* and
Ea, *Euplotes aediculatus*.
*Location is with reference to the full-length *T. thermophila* telomerase.
Location is with reference to the telomerase sequences depicted in FIGS. 2A and 2B, i.e., SEQ ID NOs: 1-8.
†location is with reference to the telomerase sequence depicted in FIGS. 3A-3C.

As further disclosed herein, the structure of *T. castaneum* telomerase identified key amino acid residues of the reverse transcriptase and "thumb" domains. In particular, key amino acid residues of the nucleotide binding pocket were identified as well as amino acid residues which appear to make direct contacts with the backbone of the DNA substrate. Accordingly, the present invention also embraces a compound, which binds to at least one amino acid residue of the nucleotide binding pocket of telomerase or residues which make direct contact with DNA. These residues are found in the "palm" and "finger" subdomains of the reverse transcriptase domain and the "thumb" domain of *T. castaneum* telomerase. Essential amino acid residues of these domains are provided in Table 2. The location of these amino acid residues in various species is also listed in Table 2.

TABLE 2

| Domain | Location in telomerases of other organisms* | | | | | | |
|---|---|---|---|---|---|---|---|
| Residues* Tt | At | Sp | Hs | Mm | Sc | Ea | |
| "Palm" | | | | | | | |
| K210 | R573 | K644 | K547 | N666 | N656 | E483 | T558 |
| V250 | L617 | A690 | I589 | V711 | A704 | F529 | M602 |
| D251 | D618 | V691 | D590 | D712 | D705 | D530 | D603 |
| I252 | I619 | D692 | I591 | V713 | V706 | V531 | I604 |
| A255 | C622 | A695 | C594 | A716 | A706 | C534 | C607 |
| Y256 | Y623 | F696 | Y595 | Y717 | Y707 | Y535 | Y608 |
| G257 | D624 | D697 | D596 | D718 | D708 | D536 | D609 |
| G305 | G770 | G801 | G703 | G830 | G823 | G629 | G734 |
| L306 | I771 | I802 | I704 | I831 | I824 | L630 | I735 |
| L307 | P772 | P803 | P705 | P832 | P825 | F631 | P736 |
| Q308 | Q773 | Q804 | Q706 | Q833 | Q826 | Q632 | Q737 |
| G309 | G774 | H805 | G707 | G834 | G827 | G633 | G738 |
| V342 | T814 | I859 | V741 | V867 | V860 | A669 | T780 |
| D343 | D815 | D860 | D742 | D868 | D861 | D670 | D781 |
| D344 | D816 | D861 | D743 | D869 | D862 | D671 | D782 |
| Y345 | Y817 | Y862 | F744 | F870 | F863 | L672 | Y783 |
| F346 | L818 | L863 | L745 | L871 | L864 | F673 | L784 |
| F347 | F819 | F864 | L872 | L865 | I674 | L785 | |
| C348 | I820 | V865 | I747 | V873 | V866 | I675 | I786 |
| S349 | S821 | S866 | T748 | T874 | T867 | S676 | T787 |
| N369 | N846 | N891 | S773 | N899 | N892 | N701 | N812 |
| K372 | K849 | K894 | K776 | K902 | K895 | K704 | K815 |
| T373 | I850 | F895 | T777 | T903 | T896 | I705 | L816 |
| "Finger" | | | | | | | |
| L184 | L533 | F612 | I502 | L621 | L611 | M438 | L514 |
| N185 | R534 | R613 | R503 | R622 | R612 | P439 | R515 |
| I186 | I535 | F614 | L504 | F623 | F613 | I440 | L516 |
| I187 | I536 | L615 | L505 | I624 | I614 | I441 | I517 |
| P188 | P537 | P616 | P506 | P625 | P615 | P442 | P518 |
| K189 | K538 | K617 | K507 | K626 | K616 | K443 | K519 |
| F193 | F542 | V621 | F511 | L630 | L620 | N447 | F523 |
| R194 | R543 | R622 | R512 | R631 | R621 | E448 | R524 |
| A195 | P544 | M623 | L513 | P632 | P622 | F449 | P525 |
| I196 | I545 | V624 | I514 | I633 | I623 | R450 | I526 |
| V197 | M546 | L625 | T515 | V634 | V624 | I451 | M527 |
| "Thumb" | | | | | | | |
| K406 | Q888 | T937 | P815 | S943 | S936 | S729 | N860 |
| K416 | T898 | T947 | T825 | S953 | S946 | K739 | T869 |
| K418 | N900 | S949 | S826 | T955 | T948 | S741 | N871 |
| N423 | K906 | K955 | H832 | K961 | K954 | R746 | K877 |

Tt, *Tetrahymena thermophila*;
At, *Arabidopsis thaliana*;
Hs, *Homo sapiens*;
Sp, *Schizosaccharomyces pombe*;
Mm, *Mus musculus*;
Sc, *Saccharomyces cerevisiae*;; and
Ea, *Euplotes aediculatus*.
*Location is with reference to the *Tribolium castaneum* telomerase sequence depicted in FIGS. 3A-3C.

Compounds designed or screened for in accordance with the present invention can interact or bind with at least one of the amino acid residues of one or more domains disclosed herein via various heterogeneous interactions including, but not limited to van der Waals contacts, hydrogen bonding, ionic interactions, polar contacts, or combinations thereof. In this regard, the terms "bind," "binding," "interact," or "interacting" are used interchangeably herein to describe the interactions between telomerase and modulators thereof. In general, it is desirable that the compound interacts with 2, 3, 4, 5, 6 or more of the amino acid residues of a domain disclosed herein to enhance the specificity of the compound for one or more telomerase proteins. Accordingly, it is desirable that the compound interacts with between 2 and 20, 2 and 10, or 2 and 5 of one or more of the domains or pockets disclosed herein.

In one embodiment, the compound interacts with one or more essential amino acids of the QFP-motif, T-motif or CP-motif. In another embodiment, the compound interacts with one or more essential amino acids of the T-motif and CP-motif. In a further embodiment, the compound interacts with one or more essential amino acids as set forth in Table 1. In particular embodiments, the compound interacts with between 2 and 33 amino acid residues of the TRBD domain. In a particular embodiment, the compound interacts with one or more essential amino acid residues set forth in Table 1, which have not been previously identified by mutation to affect RNA-binding and telomerase activity.

In another embodiment of the invention, the compound interacts with one or more essential amino acids of the nucleotide binding pocket. In a further embodiment, the compound interacts with one or more essential amino acids of telomerase in direct contact with DNA. In yet a further embodiment, the compound interacts with one or more essential amino acids as set forth in Table 2. In a particular embodiment, the compound interacts with one or more essential amino acid residues set forth in Table 2, which have not been previously identified by mutation to affect nucleotide binding, DNA binding or telomerase activity. In particular embodiments, the compound interacts with between 2 and 34 amino acid residues of the finger and palm domains. In specific embodiments, the compound binds to one or more of the amino acid residues selected from the group of K189, R194, Y256, Q308, V342, and K372 of *T. castaneum* telomerase or their equivalents in other species. In other embodiments, the compound interacts with between 2 and 15 amino acid residues of the palm and thumb domains. In specific embodiments, the compound binds to one or more of the amino acid residues selected from the group of K210, K406, K416, K418, or N423 of *T. castaneum* telomerase or their equivalents in other species.

As further disclosed herein, the structure of *T. castaneum* TERT in complex with its RNA-templating region, part of the complementary DNA, nucleotides and magnesium ions identified key amino acid residues of various domains which coordinate to place substrates in proximity with the active site (D251, D343 and D344) of telomerase. These key amino acid residues are located in Motif 2, Motif B', Thumb Loop, and Thumb Helix regions of telomerase (FIG. 3). Accordingly, the present invention further embraces a compound, which binds to at least one amino acid residue of the Motif 2, Motif B', Thumb Loop, or Thumb Helix of telomerase. Amino acid residues of Motif 2 and Motif B' are selected from the group of Ile196, Val197, Gly309 and Pro311 of *T. castaneum* telomerase or their equivalents in other species. Amino acid residues of the Thumb Loop and Thumb Helix are selected from the group of Tyr256, Gln308, Val342, Cys390, Gly391, Lys416, and Asn423 of *T. castaneum* telomerase or equivalent amino acid residues thereof in a telomerase from another species.

In accordance with the present invention, molecular design techniques can be employed to design, identify and synthesize chemical entities and compounds, including inhibitory and stimulatory compounds, capable of binding to one or more amino acids of telomerase. The structure of the domains of telomerase can be used in conjunction with computer modeling using a docking program such as GRAM, DOCK, HOOK or AUTODOCK (Dunbrack, et al. (1997) Folding& Design 2:27-42) to identify potential modulators of telomerase proteins. This procedure can include computer fitting of compounds to domains or pockets disclosed herein to, e.g., ascertain how well the shape and the chemical structure of the compound will complement the TRBD domain; or to compare the compound with the binding of TER in the TRBD; or compare the compound with the binding of a DNA molecule to the "thumb" domain; compare the compound with binding of a nucleotide substrate to the nucleotide binding pocket; or compare the compound to binding of TERT substrates in the Motif 2, Motif B', Thumb Loop, and Thumb Helix. Computer programs can also be employed to estimate the attraction, repulsion and stearic hindrance of the telomerase protein and effector compound. Generally, the tighter the fit, the lower the stearic hindrances, the greater the attractive forces, and the greater the specificity, which are important features for a specific effector compound which is more likely to interact with the telomerase protein rather than other classes of proteins. In so far as the present invention has identified the amino acid residues specifically involved in substrate binding, the present invention offers specificity not heretofore possible with conventional screening assays.

Alternatively, a chemical-probe approach can be employed in the design of telomerase modulators or effectors. For example, Goodford ((1985) *J. Med. Chem.* 28:849) describes several commercial software packages, such as GRID (Molecular Discovery Ltd., Oxford, UK), which can be used to probe the telomerase domains with different chemical probes, e.g., water, a methyl group, an amine nitrogen, a carboxyl oxygen, and a hydroxyl. Favored sites for interaction between these regions or sites of the telomerase domains and each probe are thus determined, and from the resulting three-dimensional pattern of such regions or sites a putative complementary molecule can be generated.

The compounds of the present invention can also be designed by visually inspecting the three-dimensional structure of the telomerase domains to determine more effective inhibitors or activators. This type of modeling is generally referred to as "manual" drug design. Manual drug design can employ visual inspection and analysis using a graphics visualization program such as "O" (Jones, et al. (1991) *Acta Crystallographica Section A* A47:110-119).

Initially effector compounds are selected by manual drug design. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules. Such analysis has been shown effective in the development of HIV protease inhibitors (Lam, et al. (1994) *Science* 263:380-384; Wlodawer, et al. (1993) *Ann. Rev. Biochem.* 62:543-585; Appelt (1993) *Perspectives in Drug Discovery and Design* 1:23-48; Erickson (1993) *Perspectives in Drug Discovery and Design* 1:109-128). Alternatively, random screening of a small molecule library could lead to modulators whose activity may then be analyzed by computer modeling as described above to better determine their effectiveness as inhibitors or activators.

Programs suitable for searching three-dimensional databases include MACCS-3D and ISIS/3D (Molecular Design Ltd, San Leandro, Calif.), ChemDBS-3D (Chemical Design Ltd., Oxford, UK), and Sybyl/3 DB Unity (Tripos Associates, St Louis, Mo.). Programs suitable for compound selection and design include, e.g., DISCO (Abbott Laboratories, Abbott Park, Ill.), Catalyst (Bio-CAD Corp., Mountain View, Calif.), and ChemDBS-3D (Chemical Design Ltd., Oxford, UK).

The compounds designed using the information of the present invention can bind to all or a portion of the TRBD domain, nucleotide binding domain, "thumb" domain, Motif 2, Motif B', Thumb Loop, and/or Thumb Helix of telomerase and may be more potent, more specific, less toxic and more effective than known inhibitors of telomerase. The designed compounds can also be less potent but have a longer half-life in vivo and/or in vitro and therefore be more effective at modulating telomerase activity in vivo and/or in vitro for prolonged periods of time. Such designed modulators are useful to inhibit or activate telomerase activity to, e.g., alter lifespan or proliferative capacity of a cell.

The present invention also provides the use of molecular design techniques to computationally screen small molecule databases for chemical entities or compounds that can bind to telomerase in a manner analogous to its natural substrates. Such computational screening can identify various groups which interact with one or more amino acid residues of a domain disclosed herein and can be employed to synthesize modulators of the present invention.

In vitro (i.e., in solution) screening assays are also embraced by the present invention. For example, such assays include combining telomerase, the telomerase TRBD domain (e.g., as disclosed herein), or other fragments of telomerase (e.g., motifs or pockets disclosed herein) with or without substrates or cofactors (e.g., TER, complementary DNA, nucleotides, or Mg) in solution and determining whether a test compound can block or enhance telomerase activity. In this respect, in vitro screening assays can be carried out to monitor nucleotide or DNA binding in the presence or absence of a test compound.

Compounds screened in accordance with the methods of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. Databases of chemical structures are also available from a number of sources including Cambridge Crystallographic Data Centre (Cambridge, UK) and Chemical Abstracts Service (Columbus, Ohio). De novo design programs include Ludi (Biosym Technologies Inc., San Diego, Calif.), Sybyl (Tripos Associates) and Aladdin (Daylight Chemical Information Systems, Irvine, Calif.).

Library screening can be performed using any conventional method and can be performed in any format that allows rapid preparation and processing of multiple reactions. For in vitro screening assays, stock solutions of the test compounds as well as assay components can be prepared manually and all subsequent pipeting, diluting, mixing, washing, incubating, sample readout and data collecting carried out using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

After designing or screening for a compound which binds to at least one amino acid residue of a domain or pocket disclosed herein, the compound is subsequently tested for its ability to modulate the activity of telomerase. Such activities of telomerase include telomerase catalytic activity (which may be either processive or non-processive activity); telomerase processivity; conventional reverse transcriptase activity; nucleolytic activity; primer or substrate (telomere or synthetic telomerase substrate or primer) binding activity; dNTP binding activity; RNA (i.e., TER) binding activity; and protein binding activity (e.g., binding to telomerase-associated proteins, telomere-binding proteins, or to a protein-telomeric DNA complex). See, e.g., assays disclosed in U.S. Pat. No. 7,262,288.

Telomerase catalytic activity is intended to encompass the ability of telomerase to extend a DNA primer that functions as a telomerase substrate by adding a partial, one, or more than one repeat of a sequence (e.g., TTAGGG) encoded by a template nucleic acid (e.g., TER). This activity may be processive or non-processive. Processive activity occurs when a telomerase RNP adds multiple repeats to a primer or telomerase before the DNA is released by the enzyme complex. Non-processive activity occurs when telomerase adds a partial, or only one, repeat to a primer and is then released. In vivo, however, a non-processive reaction could add multiple repeats by successive rounds of association, extension, and dissociation. This can occur in vitro as well, but it is not typically observed in standard assays due to the vastly large molar excess of primer over telomerase in standard assay conditions. Conventional assays for determining telomerase catalytic activity are disclosed, for example, in Morin (1989) *Cell* 59:521; Morin (1997) *Eur. J. Cancer* 33:750; U.S. Pat. No. 5,629,154; WO 97/15687; WO 95/13381; Krupp, et al. (1997) *Nucleic Acids Res.* 25:919; Wright, et al. (1995) *Nuc. Acids Res.* 23:3794; Tatematsu, et al. (1996) *Oncogene* 13:2265.

Telomerase conventional reverse transcriptase activity is described in, e.g., Morin (1997) supra, and Spence, et al. (1995) *Science* 267:988. Because telomerase contains conserved amino acid motifs that are required for reverse transcriptase catalytic activity, telomerase has the ability to transcribe certain exogenous (e.g., non-TER) RNAs. A conventional RT assay measures the ability of the enzyme to transcribe an RNA template by extending an annealed DNA primer. Reverse transcriptase activity can be measured in numerous ways known in the art, for example, by monitoring the size increase of a labeled nucleic acid primer (e.g., RNA or DNA), or incorporation of a labeled dNTP. See, e.g., Ausubel, et al. (1989) *Current Protocols in Molecular Biology*, John Wiley & Sons, New York, N.Y.

Because telomerase specifically associates with TER, the DNA primer/RNA template for a conventional RT assay can be modified to have characteristics related to TER and/or a telomeric DNA primer. For example, the RNA can have the sequence $(CCCTAA)_n$, where n is at least 1, or at least 3, or at least 10 or more. In one embodiment, the $(CCCTAA)_n$ region is at or near the 5' terminus of the RNA (similar to the 5' locations of template regions in telomerase RNAs). Similarly, the DNA primer may have a 3' terminus that contains portions of the TTAGGG telomere sequence, for example $X_n$TTAG, $X_n$AGGG, etc., where X is a non-telomeric sequence and n is 6-30. In another embodiment, the DNA primer has a 5' terminus that is non-complementary to the RNA template, such that when the primer is annealed to the RNA, the 5' terminus of the primer remains unbound. Additional modifications of standard reverse transcription assays that may be applied to the methods of the invention are known in the art.

Telomerase nucleolytic activity is described in, e.g., Morin (1997) supra and Collins & Grieder (1993) *Genes Dev.* 7:1364. Telomerase preferentially removes nucleotides, usually only one, from the 3' end of an oligonucleotide when the 3' end of the DNA is positioned at the 5' boundary of the DNA template sequence, in humans and *Tetrahymena*, this nucleotide is the first G of the telomeric repeat (TTAGG in humans). Telomerase preferentially removes G residues but has nucleolytic activity against other nucleotides. This activity can be monitored using conventional methods known in the art.

Telomerase primer (telomere) binding activity is described in, e.g., Morin (1997) supra; Collins, et al. (1995) *Cell* 81:677; Harrington, et al. (1995) *J. Biol. Chem.* 270:8893. There are several ways of assaying primer binding activity; however, a step common to most methods is incubation of a labeled DNA primer with telomerase or telomerase/TER under appropriate binding conditions. Also, most methods employ a means of separating unbound DNA from protein-bound DNA. Such methods can include, e.g., gel-shift assays or matrix binding assays. The DNA primer can be any DNA with an affinity for telomerase, such as, for example, a telomeric DNA primer like $(TTAGGG)_n$, where n could be 1-10 and is typically 3-5. The 3' and 5' termini can end in any location of the repeat sequence. The primer can also have 5' or 3' extensions of non-telomeric DNA that could facilitate labeling or detection. The primer can also be derivatized, e.g., to facilitate detection or isolation.

Telomerase dNTP binding activity is described in, e.g., Morin (1997) supra and Spence, et al. (1995) supra. Telomerase requires dNTPs to synthesize DNA. The telomerase protein has a nucleotide binding activity and can be assayed for dNTP binding in a manner similar to other nucleotide binding proteins (Kantrowitz, et al. (1980) *Trends Biochem. Sci.* 5:124). Typically, binding of a labeled dNTP or dNTP analog can be monitored as is known in the art for non-telomerase RT proteins.

Telomerase RNA (i.e., TER) binding activity is described in, e.g., Morin (1997) supra; Harrington, et al. (1997) *Science* 275:973; Collins, et al. (1995) *Cell* 81:677. The RNA binding activity of a telomerase protein of the invention may be assayed in a manner similar to the DNA primer binding assay described supra, using a labeled RNA probe. Methods for separating bound and unbound RNA and for detecting RNA are well known in the art and can be applied to the activity assays of the invention in a manner similar to that described for the DNA primer binding assay. The RNA can be full length TER, fragments of TER or other RNAs demonstrated to have an affinity for telomerase or TRBD. See U.S. Pat. No. 5,583,016 and WO 96/40868.

In addition to determining either RNA or DNA binding, assays monitoring binding of the RNA-templating region and the complementary telomeric DNA sequence can also be carried out. By way of illustration, Example 5 describes the use of fluorescence polarization to determine binding of compounds to TERT protein.

To further evaluate the efficacy of a compound identified using the method of the invention, one of skill will appreciate that a model system of any particular disease or disorder involving telomerase can be utilized to evaluate the adsorption, distribution, metabolism and excretion of a compound as well as its potential toxicity in acute, sub-chronic and chronic studies. For example, the effector or modulatory compound can be tested in an assay for replicative lifespan in *Saccharo-*

*myces cerevisiae* (Jarolim, et al. (2004) *FEMS Yeast Res.* 5(2):169-77). See also, McChesney, et al. (2005) *Zebrafish* 1(4):349-355 and Nasir, et al. (2001) *Neoplasia* 3(4):351-359, which describe marine mammal and dog tissue model systems for analyzing telomerase activity.

Compounds which bind to at least one amino acid residue of one or more of the telomerase domains or pockets disclosed herein can be used in a method for modulating (i.e., blocking or inhibiting, or enhancing or activating) a telomerase. Such a method involves contacting a telomerase either in vitro or in vivo with an effective amount of a compound that interacts with at least one amino acid residue of a domain or pocket of the invention so that the activity of telomerase is modulated. An effective amount of an effector or modulatory compound is an amount which reduces or increases the activity of the telomerase by at least 30%, 40%, 50%, 60%, 70%, 80%, 90% or 100% when compared to telomerase not contacted with the compound. Such activity can be monitored by enzymatic assays detecting activity of the telomerase or by monitoring the expression or activity of proteins which are known to be associated with or regulated by telomerase.

One of skill in the art can appreciate that modulating the activity of telomerase can be useful in selectively analyzing telomerase signaling events in model systems as well as in preventing or treating diseases, conditions, and disorders involving telomerase. The selection of the compound for use in preventing or treating a particular disease or disorder will be dependent upon the particular disease or disorder. For example, human telomerase is involved in cancer and therefore a compound which inhibits telomerase will be useful in the prevention or treatment of cancer including solid tumors (e.g., adenocarcinoma of the breast, prostate, and colon; melanoma; non-small cell lung; glioma; as well as bone, breast, digestive system, colorectal, liver, pancreatic, pituitary, testicular, orbital, head and neck, central nervous system, acoustic, pelvic, respiratory tract, and urogenital neoplasms) and leukemias (e.g., B-cell, mixed-cell, null-cell, T-cell, T-cell chronic, lymphocytic acute, lymphocytic chronic, mast-cell, and myeloid). Cancer cells (e.g., malignant tumor cells) that express telomerase activity (telomerase-positive cells) can be mortalized by decreasing or inhibiting the endogenous telomerase activity. Moreover, because telomerase levels correlate with disease characteristics such as metastatic potential (e.g., U.S. Pat. Nos. 5,639,613; 5,648,215; 5,489,508; Pandita, et al. (1996) *Proc. Am. Ass. Cancer Res.* 37:559), any reduction in telomerase activity could reduce the aggressive nature of a cancer to a more manageable disease state (increasing the efficacy of traditional interventions).

By way of illustration, Example 6 describes cell-based assays and animal model systems which are useful for assessing the inhibition of tumor cell growth by one or more compounds of the invention. Another useful method for assessing anticancer activities of compounds of the invention involves the multiple-human cancer cell line screening assays run by the National Cancer Institute (see, e.g., Boyd (1989) in *Cancer: Principles and Practice of Oncology Updates*, DeVita et al., eds, pp. 1-12). This screening panel, which contains approximately 60 different human cancer cell lines, is a useful indicator of in vivo antitumor activity for a broad variety of tumor types (Greyer, et al. (1992) *Seminars Oncol.* 19:622; Monks, et al. (1991) *Natl. Cancer Inst.* 83:757-766), such as leukemia, non-small cell lung, colon, melanoma, ovarian, renal, prostate, and breast cancers. Antitumor activities can be expressed in terms of $ED_{50}$ (or $GI_{50}$), where $ED_{50}$ is the molar concentration of compound effective to reduce cell growth by 50%. Compounds with lower $ED_{50}$ values tend to have greater anticancer activities than compounds with higher $ED_{50}$ values.

Upon the confirmation of a compound's potential activity in one or more in vitro assays, further evaluation is typically conducted in vivo in laboratory animals, for example, measuring reduction of lung nodule metastases in mice with B16 melanoma (e.g., Schuchter, et al. (1991) *Cancer Res.* 51:682-687). The efficacy of a compound of the invention either alone or as a drug combination chemotherapy can also be evaluated, for example, using the human B-CLL xenograft model in mice (e.g., Mohammad, et al. (1996) *Leukemia* 10:130-137). Such assays typically involve injecting primary tumor cells or a tumor cell line into immune compromised mice (e.g., a SCID mouse or other suitable animal) and allowing the tumor to grow. Mice carrying the tumors are then treated with the compound of interest and tumor size is measured to follow the effect of the treatment. Alternatively, the compound of interest is administered prior to injection of tumor cells to evaluate tumor prevention. Ultimately, the safety and efficacy of compounds of the invention are evaluated in human clinical trials.

Compounds that activate or stimulate telomerase activity can be used in methods for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. Certain diseases of aging are characterized by cell senescence-associated changes due to reduced telomere length (compared to younger cells), resulting from the absence (or much lower levels) of telomerase activity in the cell. Telomerase activity and telomere length can be increased by, for example, increasing the activity of telomerase in the cell. A partial listing of conditions associated with cellular senescence in which increased telomerase activity can be therapeutic includes Alzheimer's disease, Parkinson's disease, Huntington's disease, and stroke; age-related diseases of the integument such as dermal atrophy, elastolysis and skin wrinkling, graying of hair and hair loss, chronic skin ulcers, and age-related impairment of wound healing; degenerative joint disease; osteoporosis; age-related immune system impairment (e.g., involving cells such as B and T lymphocytes, monocytes, neutrophils, eosinophils, basophils, NK cells and their respective progenitors); age-related diseases of the vascular system; diabetes; and age-related macular degeneration. Moreover, telomerase activators can be used to increase the proliferative capacity of a cell or in cell immortalization, e.g., to produce new cell lines (e.g., most human somatic cells).

Prevention or treatment typically involves administering to a subject in need of treatment a pharmaceutical composition containing an effective of a compound identified via screening methods of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of preventing, reducing or reversing at least one sign or symptom of the disease or disorder being treated. Methods for treating cancer and other telomerase-related diseases in humans are described in U.S. Pat. Nos. 5,489,508, 5,639,613, and 5,645,986. By way of illustration, a subject with cancer (including, e.g., carcinomas, melanomas, sarcomas, lymphomas and leukaemias) can experience unexplained weight loss, fatigue, fever, pain, skin changes, sores that do not heal, thickening or lump in breast or other parts of the body, or a nagging cough or hoarseness, wherein treatment with a compound of the invention can prevent, reduce, or reverse one or more of these symptoms.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and anti-oxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

Example 1

Structure of *Tetrahymena thermophila* TERT

Protein Expression and Purification. The *T. thermophila* TERT residues 254-519 was identified by limited proteolysis and cloned into a modified version of the pET28b vector containing a cleavable hexa-histidine tag at its N-terminus. The protein was over-expressed in *E. coli* BL21 (pLysS) at 20° C. for 4 hours. The cells were lysed by sonication in 50 mM Tris-HCl, 10% glycerol, 0.5 M KCl, 5 mM β-mercaptoethanol, and 1 mM PMSF, pH 7.5 on ice. The protein was first purified over a Ni-NTA column followed by TEV cleavage of the hexa-histidine tag overnight at 4° C. The TRBD/TEV mix was diluted so that the concentration of imidazole was at 15 mM and the protein mix was passed over a Ni-NTA column to remove the TEV, the cleaved tag and any tagged protein. The Ni-NTA flow through was concentrated to 1 ml and diluted to a salt concentration of 0.15 M. The diluted TRBD sample was then passed over a POROS-HS column (PerSeptive Biosystems, Framingham, Mass.). At this stage, the protein was more than 99% pure. The protein was finally passed over a SEPHADEX-S200 sizing column pre-equilibrated with 50 mM Tris-HCl, 10% glycerol, 0.5 M KCl, and 2 mM DTT, pH 7.5 to remove any TRBD aggregates. The pure, monodisperse protein as indicated by SDS-page and dynamic light scattering, respectively, was concentrated to 8 mg/ml using an AMICON 10K cutoff (MILLIPORE, Billerica, Mass.) and the protein was stored at 4° C. for subsequent studies. Stock protein was dialyzed in 5 mM Tris-HCl, 500 mM KCl, 1 mM TCEP, pH 7.5 prior to crystallization trials.

Protein Crystallization and Data Collection. Initial plate-like clusters of TRBD that diffracted poorly (~4 Å resolution) were grown at 4° C. using the sitting drop method by mixing on volume of dialyzed protein with one volume of reservoir solution containing 20% PEG 3350, 0.2 M NaNO$_3$. Single, well diffracting crystals were grown in microbatch trays under paraffin oil by mixing one volume of dialyzed protein with an equivalent volume of 50 mM HEPES (pH 7.0), 44% PEG 400, 0.4 M NaNO$_3$, 0.4 M NaBr and 1 mM TCEP at 4° C. Crystals were harvested into cryoprotectant solution that contained 25 mM HEPES (pH 7.0), 25% PEG 400, 0.2 M NaNO$_3$, 0.2 M NaBr and 1 mM TCEP and were flash frozen in liquid nitrogen. Data were collected at the NSLS, beam line X6A and processed with HKL-2000 (Minor (1997) *Meth. Enzymol. Macromole. Crystallogr. Part A* 276:307-326) (Table 3). The crystals belong to the monoclinic space group P2$_1$ with one monomer in the asymmetric unit.

TABLE 3

| | Native | Holmium-Derivative | |
|---|---|---|---|
| TRBD$_{(254-519)}$ | λ | Ho-λ1 | Ho-λ2 |
| Wavelength (Å) | 0.9795 | 1.5347 | 1.5595 |
| Space group | P2$_1$ | P2$_1$ | P2$_1$ |
| Cell dimensions (Å) | 39.4 67.2 51.5 90.7 | 39.2 68.2 50.1 91.6 | 39.2 68.2 50.1 91.6 |
| Resolution (Å) | 20-1.71 (1.77-1.71)* | 50-2.59 (2.69-2.59) | 50-2.63 (3.02-2.63) |

TABLE 3-continued

| TRBD$_{(254-519)}$ | Native | Holmium-Derivative | |
| --- | --- | --- | --- |
| | λ | Ho-λ1 | Ho-λ2 |
| Redundancy | 3.7 (3.0) | 1.7 (1.8) | 1.7 (1.8) |
| Completeness (%) | 99.3 (93.3) | 92.5 (88.1) | 92.9 (88.7) |
| R$_{sym}$ (%) | 4.7 (48.1) | 7.3 (23.8) | 7.0 (21.5) |
| I/σ (I) | 27.3 (2.6) | 9 (3.4) | 9.4 (3.7) |
| Phasing Analysis | | | |
| Resolution (Å) | 50-2.7 | | |
| Number of sites | 2 | | |
| Mean figure of merit (FOM) | 0.43 | | |

*Values in parentheses correspond to the highest resolution shell.

Structure Determination and Refinement. Initial phases were obtained from a two-wavelength MAD holmium (Ho) derivative that was prepared by co-crystallizing the protein with 5 mM HoCl$_3$. Heavy atom sites were located using SOLVE (Terwilliger (2003) *Methods Enzymol.* 374:22-37) and the sites were refined and new phases calculated with MLPHARE (CCP4 (1994) *Acta Crystallogr. D* 50:760-763) as implemented in ELVES (Holton & Alber (2004) *Proc. Natl. Acad. Sci. USA* 101:1537-1542) (Table 3). Initial maps showed well-defined density only for the larger half of the molecule. The density for the smaller half of the molecule was weak mostly due to its intrinsic mobility with respect to larger half of the molecule. The problem associated with building the model into the density was exacerbated by the lack of information regarding the location of specific side chains such as selenomethionines. Key factors in building a complete model were successive rounds of PRIME and SWITCH in RESOLVE (Terwilliger (2002) *Acta Crystallogr. D Biol. Crystallogr.* 58:1937-1940) followed by manual building in COOT (Emsley & Cowtan (2004) *Acta Crystallogr. D Biol. Crystallogr.* 60:2126-2132). The model was refined using both CNS-SOLVE (Brunger, et al. (1998) *Acta Crystallogr. D Biol. Crystallogr.* 54:905-921) and REFMAC5 (Murshudov, et al. (1997) *Acta Crystallogr. D Biol. Crystallogr.* 53:240-255). The last cycles of refinement were carried out with TLS restraints as implemented in REFMAC5 (Table 4). Figures were prepared in PYMOL (DeLano (2002)) and electrostatic surfaces in APBS (Baker, et al. (2001) *Proc. Natl. Acad. Sci. USA* 98:10037-10041).

TABLE 4

| TRBD$_{(254-519)}$ | |
| --- | --- |
| Refinement Statistics | |
| Resolution (Å) | 20-1.71 |
| R$_{work}$/R$_{free}$ (%) | 20.0/23.9 |
| RMSD bonds (Å) | 0.008 |
| RMSD angles (°) | 0.831 |
| Number of atoms | |
| Protein | 2145 |
| Bromine | 7 |
| Water | 213 |
| Average B (Å$^2$) | |
| Protein | 27.41 |
| Bromine | 42.63 |
| Water | 31.22 |
| Ramachandran % (no res.) | |
| Most favored | 91.6 |
| Allowed | 8.4 |

TRBD Structure. To explore the role of the essential RNA-binding domain of telomerase (TRBD), a construct identified by limited proteolysis, containing residues 254-519 from *T. thermophila* (FIG. 1A) was purified to homogeneity. This protein construct was monomeric in solution as indicated by both gel filtration and dynamic light scattering. Crystals of this construct grew readily and diffracted to 1.71 Å resolution (Table 4). The protein was phased to 2.7 Å resolution by the multiwavelength anomalous dispersion method (MAD) using a holmium derivative and the phases were extended with the native dataset to 1.71 Å resolution (Table 4). In the refined structure there was clear density for residues 257-266 and 277-519.

The structure contains twelve α-helices linked together by several long loops and two short β-strands. The helices are organized so that the molecule is divided into two asymmetric halves linked together by three extended loops. The larger half is composed of nine α-helices, one of which (α11) runs along the middle of the domain and spans its entire length making contacts with all other eight helices. The smaller half of the molecule is composed of three helices (α4, α5 and α12), all of which are arranged at a ~120° angle to the plane of the larger half of the protein. The smaller half of the protein is somewhat more flexible than the larger half as suggested by its high B factors reflecting the intrinsic mobility of this region and may result from the absence of observable contacts with the RNA substrate. An interesting feature of the structure is a β-hairpin formed by the 15-residues that connect helices α11 and α12 of the larger and the smaller halves, respectively. The β-hairpin protrudes from the base of the crevice formed by the two halves of the protein and stands at a 45° angle to the plane of the smaller half of the molecule. The positioning and the fact that this hairpin is well-defined in the density could be attributed to helix α7 and the loop that connects it to helix α8. Both of these elements are conveniently positioned at the back of this hairpin holding it in place. A search in the protein structure database using the Dali server (Holm & Sander (1996) *Science* 273:595-603) produced no structural homologues, indicating that the TRBD domain of telomerase is a novel nucleic acid binding fold. The overall organization of the two halves of the protein has significant implications for nucleic acid recognition and binding.

The TRBD RNA-Binding Motifs. The ability of the TRBD domain to interact with TER has been attributed to two conserved motifs known as the CP-, and T-motifs, while a third motif known as the QFP-motif is thought to be important for RNP assembly (FIGS. 2A and 2B) (Bosoy, et al. (2003) *J. Biol. Chem.* 278:3882-3890; Bryan, et al. (2000) supra; Jacobs, et al. (2005) supra; Xia, et al. (2000) *Mol. Cell. Biol.* 20:5196-5207). The TRBD structure shows that the QFP-motif is formed by several mostly hydrophobic residues, which are located on the larger half of the molecule and are buried within the core of the domain making extensive hydrophobic contacts with the surrounding residues aiding in the fold of the protein. These residues included Gln375, Ile376, Leu380, Ile383, Ile384, Cys387, Val388, Pro389, Leu392, Leu393, Asn397, Leu405, Phe408, Tyr422, Ile423, Met426, Trp433, and Phe434. The location and the contacts of the QFP-residues indicate that they are not directly involved in nucleic acid binding.

The T-motif is located at the center of the molecule where the two halves of the protein meet and it is composed of residues that form both part of the β-hairpin and helix α12. Together these structural elements form a narrow (~10 Å), well-defined pocket (T-pocket) that is lined by several solvent exposed and highly conserved residues (Phe476, Tyr477, Thr479, Glu480, Tyr491, Arg492, Lys493, and Trp496). Of particular note are the side chains of the invariant residues Tyr477 and Trp496, which are part of the β-hairpin and helix α12, respectively. Together these residues form a "hydrophobic pincer" that could sandwich the purine/pirimidine moiety of an interacting RNA nucleotide. In this structure, the side chains of Tyr477 and Trp496 are only 4 Å apart, which is not sufficient to accommodate a nucleotide base. Insertion of a base between the two side chains would require structural rearrangement of the T-pocket, possibly splaying of the two halves of the molecules apart. In addition to its hydrophobic part, the T-pocket also contains several hydrophilic residues such as Arg492 and Lys493 both of which are solvent exposed and are located at the interface of the T- and CP-pocket connecting the two together.

The CP-motif is formed by helix α3 and the following loop. In contrast to the T-motif, which is a narrow well-defined pocket, the CP-motif is composed a shallow, wide (~20 Å), highly positively charged cavity located adjacent and beneath the entry of the T-pocket. Several of the conserved residues that form the CP-motif include Phe323, Leu327, Lys328, Lys329, Cys331, Leu333, and Pro334. These residues are buried in the core of the larger half or the region that connects the two halves of the molecule and are contributing to the protein fold. Of particular interest are residues Leu327, Cys331, Leu333 and Pro334 all of which are buried and make direct contacts with structural elements of the T-motif thus aiding in the formation of both the CP- and the T-pockets. For example, Leu327 and Cys331 are within Van der Waal contacts of the large hydrophobic side chain of the invariant Phe476 and the aliphatic part of the side chain of the conserved Arg492 both of which form part of the β-hairpin. Interestingly, Arg492 is located at the base of helix α12 and its contact with Leu327, Cys331, and Leu333 partially helps position this helix at a 45° angle of the plane that runs parallel with the larger half of the molecule thus further facilitating the formation of the T-pocket. Moreover, the interaction of Arg492 with Leu327, Cys331, and Leu333 helps position the guanidine moiety, the only solvent-exposed part of this residue, at the interface formed by the CP- and T-pockets. The CP-pocket also contains several surface-exposed, conserved residues that are mainly hydrophilic in nature. These include Lys328 and Lys329 both of which are located beneath the T-pocket and in close proximity of Arg492 and Lys493 together forming a single large, positively charged surface area that almost spans the entire side of the molecule.

TRBD Structure and Existing Mutants. Several mutants of TERT that affect RNA-binding and telomerase activity have been isolated. Several of these mutants are found in the TRBD domain and specifically within the T- and CP-motifs. Single- and double- as well as stretches of 4-10 amino acid alanine substitutions within these two motifs showed moderate to severe loss (20-100%) of RNA-binding affinity and polymerase activity when compared to the wild type enzyme (Bryan, et al. (2000) supra; Lai, et al. (2002) supra; Miller, et al. (2000) supra).

One set of mutants, Phe476Ala, Tyr477Ala, Thr479Ala, Glu480Ala, Arg492Ala and Trp496Ala, showed severe loss (80-100%) of RNA-binding affinity and telomerase activity suggesting that these residues mediate direct contacts with the RNA substrate (Bryan, et al. (2000) supra; Lai, et al. (2002) supra). All five residues are part of the T-motif and, with the exception of Phe476, all of their side chains are solvent exposed. In the structure, both Tyr477 and Trp496 are located at the base of the T-pocket and their side chains form a "hydrophobic pincer". Assuming that the solvent-exposed side chains of these residues are involved in stacking interactions with the ssRNA, mutating them to small alanines would likely compromise substrate binding which explains the dramatic loss of RNA-binding affinity and telomerase function.

In contrast to Tyr477 and Trp496, Phe476 is buried and is not accessible for interactions with the nucleic acid substrate. Instead, Phe476 is located at the base of the β-hairpin and contributes significantly to the formation of the T-pocket. Mutating the large hydrophobic side chain of this residue to the small alanine would likely lead to conformational rearrangements of this pocket and loss of RNA-binding affinity and telomerase activity.

A second set of alanine mutants, Leu327Ala, Lys329Ala, Cys331Ala, and Pro334Ala, which showed moderate loss of RNA-binding affinity and telomerase activity has also been isolated (Bryan, et al. (2000) supra; Miller, et al. (2000) supra). Both Leu327 and Cys331 make direct contacts with Phe476 and the aliphatic part of the side chain of Arg492, both of which are located at the base of the T-motif. Mutation to the smaller alanine residue could result in the rearrangement of the T-pocket potentially leading to loss of interactions with the nucleic acid substrate and loss of function. Likewise, Pro334 is located at the back of helix α12 and makes direct contacts with residues of this structural element. Helix α12 contains the invariant Trp496 and the conserved Lys493, both of which form part of the T-pocket. Mutating Pro334 into an alanine could lead to the displacement of helix α10 and reorganization of the T-pocket leading to loss of function. Lys329 is also located on helix α3 and unlike Leu327Ala, Cys331Ala, and Pro334Ala, is solvent exposed possibly making direct contacts with the nucleic acid substrate. Mutating it to an alanine would lead to lose of RNA interactions and loss of RNA-binding affinity and telomerase activity.

Figure 4:
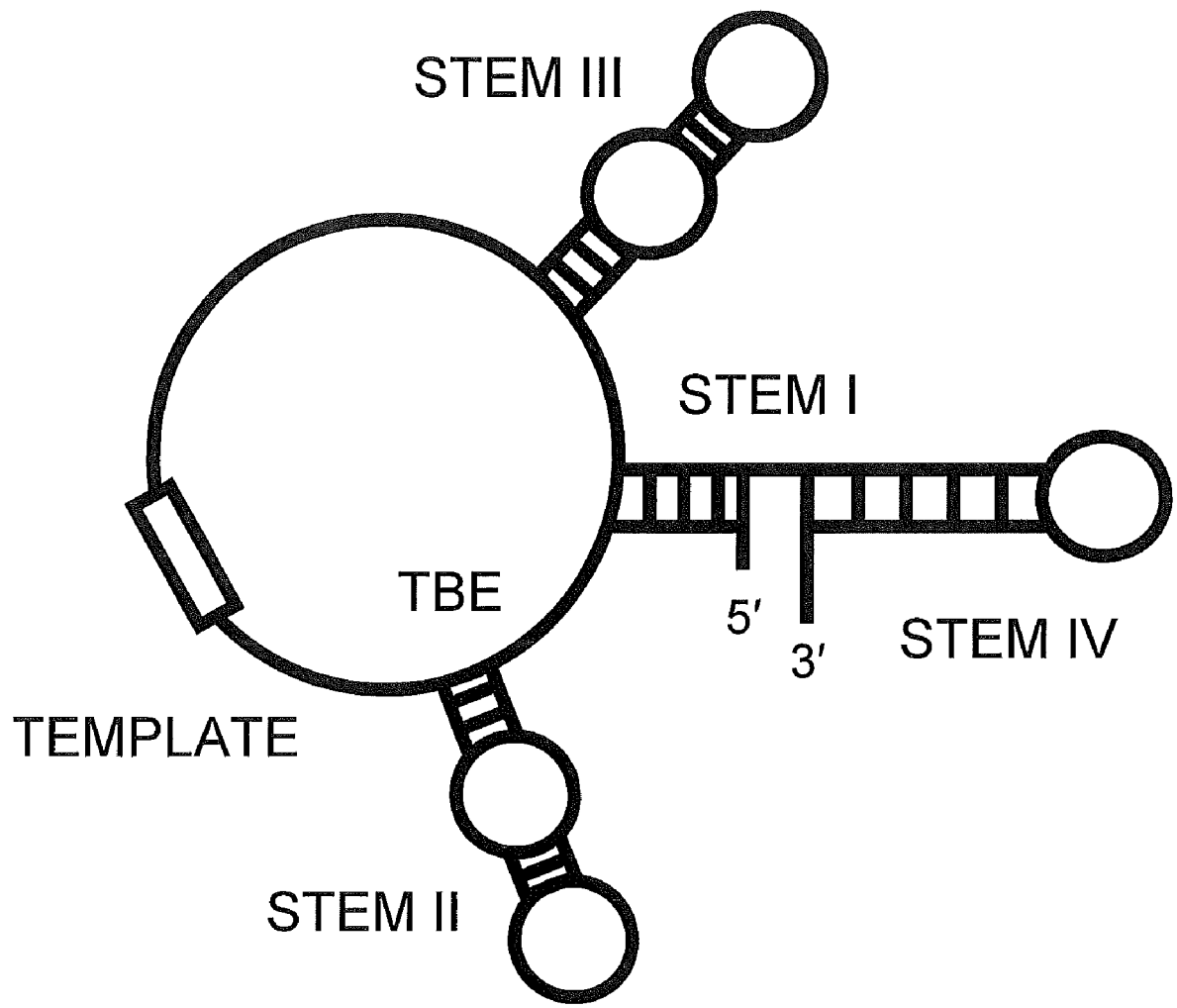
FIG. 4 is a schematic of the primary structure of the RNA component (TER) of telomerase from *Tetrahymena thermophila*. Stem I, TBE and the template are indicated.

TRBD Domain-Mediated Formation of Stable RNP Complex and Repeat Addition Processivity. In vivo, telomerase exists as a stable ribonucleoprotein complex and contacts between the protein (TERT) and the RNA components (TER) are mediated by the TEN, TRBD and the RT domains. Extensive biochemical and mutagenesis studies have shown that the TRBD is involved in extensive, specific interactions with stem I and the TBE of TER (Lai, et al. (2001) supra; O'Connor, et al. (2005) supra) (FIG. 4). Contacts between the TRBD and TER are thought to facilitate the proper assembly and stabilization of the RNP complex and promote repeat addition processivity (Lai, et al. (2003) supra). In ciliates, in addition to the TRBD, a conserved motif (CP2) located N-terminally to the TRBD domain is thought to be required for TERT-TER assembly and template boundary definition (Lai, et al. (2002) supra; Miller, et al. (2000) supra). However, until now it has been unclear as to how the telomerase TRBD carries out this process. The present analysis indicates that the TRBD domain is divided into two asymmetric halves connected by several long loops that are shaped like a boomerang, an arrangement that has significant implications for RNA recognition and binding. The overall organization of the two lobes of the molecule results in the formation of two well-defined cavities (CP- and T-pockets) on the surface of the protein that consist of several solvent-exposed, invariant/conserved residues. The T-pocket is a narrow, deep cavity located at the junction of the two halves of the molecule with part of it being hydrophobic in nature while the part that is located in proximity of the CP-pocket is positively charged. Interestingly, the hydrophobic side chains of Tyr477 and Trp496 are solvent-exposed and are stacked against each other forming a narrow "hydrophobic pincer" that in this structure could not accommodate a nucleotide base. It is, however, worth noting that helix α12, which contains Trp496, is somewhat flexible with respect to the β-hairpin that contains Tyr477. The ability of helix α12 and therefore Trp496 to move could splay the two side chains apart thus allowing for the space required for the accommodation of a nucleotide base between them. Another possibility is that the polar moiety of Tyr477 and Trp496 could act together as a nucleotide base that would allow for the formation of pseudo Watson Crick interactions with an incoming nucleotide base. Pseudo Watson Crick interactions have been previously observed for a number of protein nucleic acid complexes including the Rho transcription termination factor (Bogden, et al. (1999) *Mol. Cell.* 3:487-493) and the signal recognition particle (Wild, et al. (2001) *Science* 294:598-601). The width and the organization of the hydrophobic part of the T-pocket indicate that it binds ssRNA, most likely the TBE, possibly mediated by a network of stacking interactions.

In contrast to the T-pocket, the CP-pocket is a positively charged, shallow cavity located on the side of the molecule and forms an extension of the T-pocket. Together the hydrophilic part of the T-pocket and the CP-pocket are lined with several lysines and arginines the side chains of which are solvent exposed and could be involved in direct contacts with the backbone of double-stranded RNA. The width and the chemical nature of this pocket indicate that it binds double-stranded RNA, most likely stem I or stem II (FIG. 4). The nature and the extent of the protein/nucleic acid interactions mediated by the TRBD binding pockets provides the stability required for the proper assembly of a functional ribonucleoprotein enzyme and guide TERT to a TER binding site (between stem I and II) that has significant implications for telomerase function.

Telomerase is unique in its ability to add multiple short oligonucleotide repeats at the end of linear chromosomes. The enzyme's ability to do so has been partly attributed to the interactions of the TRBD domain with the TBE and in ciliates both the TRBD and the CP2 motif (Lai, et al. (2002) supra; Lai, et al. (2003) supra; Miller, et al. (2000) supra). The TBE is composed of stem II and the flanking ssRNA regions and is located downstream of stem I and only a few nucleotides upstream of the RNA template (FIG. 4). The TRBD structure indicates that the T-pocket, a narrow, hydrophobic cavity located on the surface of the protein that can only accommodate ssRNA, may play an important role in this process. Assuming that the T-pocket binds the ssRNA that connects stem I and stem II, this interaction likely forces stem II to act as a steric block, which in turn forces the TRBD domain to stay within the boundaries of stem I and stem II. The stem I- and II-locked TRBD domain then may act as an anchor that constrains the distance the RT domain can travel and prevents it from moving beyond the boundaries of the RNA template thus promoting telomerase addition processivity. In ciliates however, the TRBD domain alone is not sufficient for template boundary definition and it requires the action of the CP2 motif (Lai, et al. (2002) supra; Miller, et al. (2000) supra). It is contemplated that CP2 binding to TER promotes template boundary definition either via contributing to the stabilization of the RNP complex or, like the TRBD, it may act as an anchor that prevents slippage of the active site of the RT domain beyond the RNA template.

Example 2

Structure of *Tribolium castaneum* TERT in Complex with DNA Substrate

Protein Expression and Purification. The synthetic gene of *T. castaneum* full-length TERT was cloned into a modified version of the pET28b vector containing a cleavable hexahistidine tag at its N-terminus. The protein was over-expressed in *E. coli* BL21 (pLysS) at 30° C. for 4 hours. The cells were lysed by sonication in 50 mM Tris-HCl, 10% glycerol, 0.5 M KCl, 5 mM β-mercaproethanol, and 1 mM PMSF, pH 7.5 on ice. The protein was first purified over a Ni-NTA column followed by TEV cleavage of the hexahistidine tag overnight at 4° C. The TERT/TEV mixture was dialyzed to remove the excess imidazole and the protein was further purified over a second Ni-NTA column that was used to remove all his-tagged products. The Ni-NTA flow through was then passed over a POROS-HS column (Perseptive Biosystems) to remove any trace amounts of protein contaminants. At this stage the protein was more than 99% pure. The protein was finally purified over a SEPHEDEX-S200 sizing column pre-equilibrated with 50 mM Tris-HCl, 10% glycerol, 0.5 M KCl, and 1 mM Tris(2-Carboxyethyl) phosphine (TCEP), pH 7.5 to remove any TERT aggregates and the protein was concentrated to 10 mg/ml using an AMICON 30K cutoff (MILLIPORE) and stored at 4° C. for subsequent studies. Stock protein was dialyzed in 10 mM Tris-HCl, 200 mM KCl, 1 mM TCEP, pH 7.5 prior to crystallization trials.

Protein Crystallization and Data Collection. Initial crystal trials of the protein alone did not produce crystals. Co-crystallization of the protein with single stranded telomeric DNA ((TCAGG)$_3$) produced two rod-like crystal forms one of which belongs to the orthorhombic space group P2$_1$2$_1$2$_1$ and diffracted to 2.71 Å and the other to the hexagonal space group P6$_1$ and diffracted to 3.25 Å resolution. The protein nucleic acid mix was prepared prior to setting crystal trials by mixing one volume of dialyzed protein with 1.2-fold excess of the DNA substrate. Both crystal forms where grown by the vapor diffusion, sitting drop method by mixing on volume of the protein-DNA mix with one volume of reservoir solution. Orthorhombic crystals where grown in the presence of 50 mM HEPES, (pH 7.0) and 1.5 M NaNO$_3$ while hexagonal crystals grew in the presence of 100 mM Tris (pH 8.0) and 2 M (NH$_4$)$_2$SO$_4$ and both at room temperature. Orthorhombic crystals were harvested into cryoprotectant solution that contained 50 mM HEPES (pH 7.0), 25% glycerol, 1.7 M NaNO$_3$, 0.2 M KCl and 1 mM TCEP and were flash frozen in liquid nitrogen. Hexagonal crystals were harvested into cryoprotectant solution that contained 100 mM Tris (pH 8.0), 25% glycerol, 2 M (NH$_4$)$_2$SO$_4$, 0.2 M KCl and 1 mM TCEP and were also flash frozen in liquid nitrogen. Data were collected at the NSLS, beam line X6A and processed with HKL-2000 (Minor (1997) *Methods in Enzymology: Macromolecular Crystallography, part A* 276:307-326) (Table 5). Both crystal forms contain a dimer in the asymmetric unit.

TABLE 5

|  | Native 1 | Native 2 | Hg1 | Hg2 |
|---|---|---|---|---|
| Data collection |  |  |  |  |
| Space group | P2$_1$2$_1$2$_1$ | P6$_1$ | P2$_1$2$_1$2$_1$ | P2$_1$2$_1$2$_1$ |
| Cell dimensions |  |  |  |  |
| a, b, c (Å) | 85.0420, 122.6570, 212.4060 | 200.0670, 200.0670, 96.4100 | 86.7165, 123.3500, 211.4530 | 86.9260, 123.4100, 211.4160 |

TABLE 5-continued

|  | Native 1 | Native 2 | Hg1 | Hg2 |
|---|---|---|---|---|
| Resolution (Å) | 40-2.70 | 40-3.25 | 40-3.5 | 40-3.5 |
|  | (2.78-2.71)* | (3.32-3.25) | (3.69-3.5) | (3.69-3.5) |
| $R_{sym}$ or $R_{merge}$ | 10.7 (48.1) | 14.9 (42.6) | 14.5 (41.7) | 16.1 (43.7) |
| I/σI | 9.3 (1.7) | 6.4 (2.4) | 7.0 (3.5) | 7.3 (3.6) |
| Completeness (%) | 96.97 (95.84) | 98.85 (98.1) | 85.7 (83.1) | 93.8 (94.2) |
| Redundancy | 4.2 (4.2) | 2.8 (2.5) | 4.7 (4.8) | 5.3 (5.3) |
| Refinement |  |  |  |  |
| Resolution (Å) | 20-2.71 | 20-3.25 |  |  |
| No. reflections | 56173 | 32773 |  |  |
| $R_{work}/R_{free}$ | 23.8/27.7 | 24.3/29.6 |  |  |
| No. atoms |  |  |  |  |
| Protein | 4982 | 4982 |  |  |
| Water | 358 | 77 |  |  |
| B-factors |  |  |  |  |
| Protein | 52.5 | 37.8 |  |  |
| Water | 41.3 | 26.5 |  |  |
| R.m.s deviations |  |  |  |  |
| Bond lengths (Å) | 0.007 | 0.006 |  |  |
| Bond angles (°) | 0.848 | 0.735 |  |  |
| Ramachandran plot (%) |  |  |  |  |
| Most favored | 83.3 | 86.4 |  |  |
| Allowed | 15.2 | 11.5 |  |  |
| Generously allowed | 1.4 | 1.7 |  |  |
| Disallowed | 0.2 | 0.4 |  |  |

*Highest resolution shell is shown in parenthesis.

Structure Determination and Refinement. Initial phases for the orthorhombic crystals were obtained using the method of single isomorphous replacement with anomalous signal (SIRAS) using two datasets collected from two different mercury ($CH_3HgCl$) derivatized crystals at two different wavelengths (Hg1-1.00850 Å; Hg2-1.00800 Å) (Table 5). The derivatives were prepared by soaking the crystals with 5 mM methyl mercury chloride ($CH_3HgCl$) for 15 minutes. Initially, twelve heavy atom sites were located using SOLVE (Terwilliger (2003) *Methods Enzymol.* 374:22-37) and refined and new phases calculated with MLPHARE (Collaborative Computational Project 4 (1994) *Acta Crystallogr. D* 50:760-763). MLPHARE improved phases were used to identify the remaining heavy atom sites (twenty two in total) by calculating an anomalous difference map to 3.5 Å resolution. MLPHARE phases obtained using all the heavy atom sites where then used in DM with two-fold NCS and phase extension using the high-resolution (2.71 Å) dataset collected, at 1.00800 Å wavelength, to calculate starting experimental maps. These maps were sufficiently good for model building which was carried out in COOT (Emsley & Cowtan (2004) *Acta Crystallogr D Biol Crystallogr* 60:2126-32). The electron density map revealed clear density for all 596 residues of the protein. However, density for the nucleic acid substrate in the structure was not observed. The model was refined using both CNS-SOLVE (Brunger, et al. (1998) *Acta Crystallogr D Biol Crystallogr* 54:905-21) and REFMAC5 (Murshudov, et al. (1997) *Acta Crystallogr D Biol Crystallogr* 53:240-55). The last cycles of refinement were carried out with TLS restraints as implemented in REFMAC5 (Table 5). The $P2_12_12_1$ refined model was used to solve the structure of the TERT crystallized in the $P6_1$ crystal form (data collected at 0.97980 Å wavelength) by molecular replacement with PHASER (Potterton, et al. (2003) *Acta Crystallogr D Biol Crystallogr* 59:1131-7).

Architecture of the TERT Structure. The structure of the full-length catalytic subunit of the *T. castaneum* active telomerase, TERT, was determined to 2.71 Å resolution. As indicated, there was a dimer in the asymmetric unit (AU), however the protein alone was clearly monomeric in solution as indicated by gel filtration and dynamic light scattering, indicating that the dimer observed in the crystal was the result of crystal packing.

This was further supported by the fact that a different crystal form (Table 5) of the same protein also contained a dimer in the AU of different configuration. It is worth noting that the TERT from this organism does not contain a TEN domain, a low conservation region of telomerase (FIG. 1B).

Figure 1B:
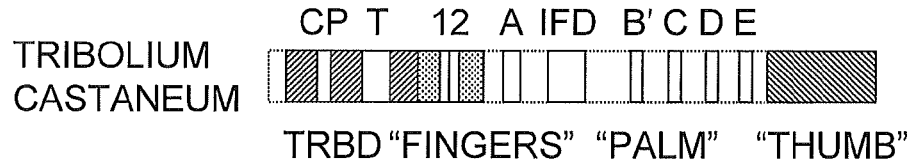
FIG. 1B is the primary structure and conserved motifs of the *Tribolium castaneum* TERT.
Figure 2A:
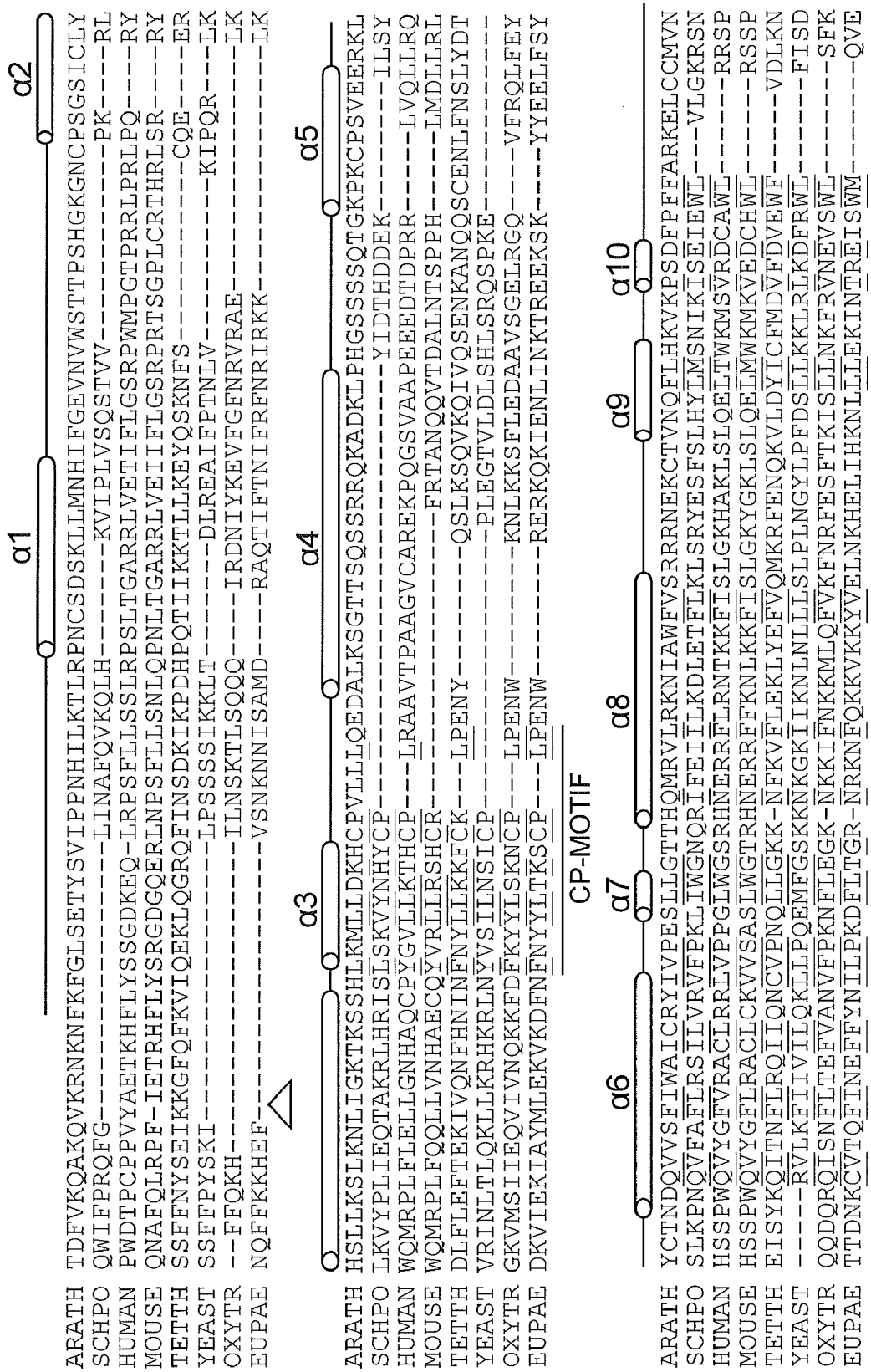
FIGS. 2A and 2B show a sequence alignment and schematic of secondary structure of *Tetrahymena thermophila* TRBDs (TETTH; SEQ ID NO:1) compared with the TRBDs from ciliated protozoa such as, *Euplotes aediculatus* (EUPAE; SEQ ID NO:2) and *Oxytricha trifallax* (OXYTR; SEQ ID NO:3); mammals such as human (SEQ ID NO:4) and mouse (SEQ ID NO:5); fungi such as *Schizosaccharomyces pombe* (SCHPO; SEQ ID NO:6) and *Saccharomyces cerevisiae* (YEAST; SEQ ID NO:7); and plants such as *Arabidopsis thaliana* (ARATH; SEQ ID NO:8) produced by ALSCRIPT Barton (1993) *Protein Eng.* 6:37-40). Conserved residues in key signature motifs are indicated and mutated residues that affect RNA-binding and telomerase function are also indicated. The solid triangles define the boundaries of the TRBD construct used in the studies herein.
Figure 2B:
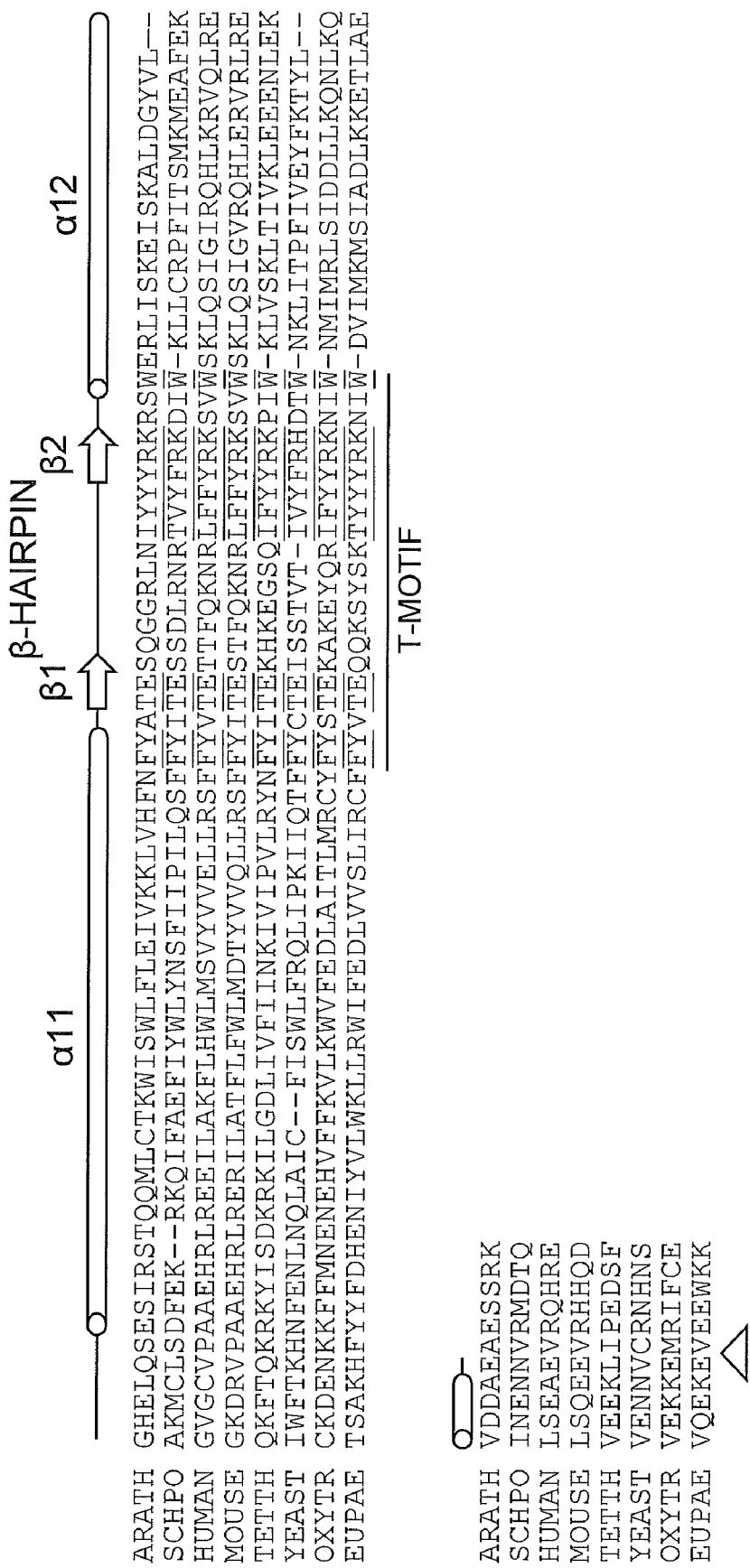

The TERT structure is composed of three distinct domains, a TER-binding domain (TRBD), the reverse transcriptase (RT) domain, and the C-terminal extension thought to represent the putative "thumb" domain of TERT (FIGS. 1A and 1B). As indicated herein, the TRBD is mostly helical and contains an indentation on its surface formed by two conserved motifs (CP and T) which bind double- and single-stranded RNA, respectively, and has been defined as the template boundary element of the RNA substrate of telomerase, TER. Structural comparison of the TRBD domain from *T. castaneum* with that of the structure from *T. thermophila* shows that the two structures are similar (RMSD 2.7 Å), indicating a high degree of structural conservation between these domains across organisms of diverse phylogenetic groups.

The RT domain is a mix of α-helices and β-strands organized into two subdomains that are most similar to the "fingers" and "palm" subdomains of retroviral reverse transcriptases such as HIV reverse transcriptase (PDB code ID 1N5Y; Sarafianos, et al. (2002) *EMBO J.* 21:6614-24), viral RNA polymerases such as hepatitis C viral polymerase (Code ID 2BRL Di Marco, et al. (2005) *J. Biol. Chem.* 280:29765-

70) and B-family DNA polymerases such as RB69 (PDB Code ID 1WAF; Wang, et al. (1997) *Cell* 89:1087-99), and contain key signature motifs that are hallmarks of these families of proteins (Lingner, et al. (1997) *Science* 276:561-7) (FIGS. 3A-3C). Structural comparison of TERT with the HIV RTs, shows that the "fingers" subdomain of TERT (i.e., motifs 1 and 2) are arranged in the open configuration with respect to the "palm" subdomain (i.e., motifs A, B', C, D, and E), which is in good agreement with the conformation adopted by HIV RTs in the absence of bound nucleotide and nucleic acid substrates (Ding, et al. (1998) *J. Mol. Biol.* 284: 1095-111). One striking difference between the putative "palm" domain of TERT and that HIV reverse transcriptases is a long insertion between motifs A and B' of TERT referred to as the IFD motif that is required for telomerase processivity (Lue, et al. (2003) *Mol. Cell. Biol.* 23:8440-9). In the TERT structure, the IFD insertion is composed of two anti-parallel α-helices (α13 and α14) located on the outside periphery of the ring and at the interface of the "fingers" and the "palm" subdomains. These two helices are almost in parallel position with the central axis of the plane of the ring and make extensive contacts with helices α10 and α15 and play an important role in the structural organization of this part of the RT domain. A similar structural arrangement is also present in viral polymerases, and the equivalent of helix α10 in these structures is involved in direct contacts with the nucleic acid substrate (Ferrer-Orta, et al. (2004) *J. Biol. Chem.* 279:47212-21).

In contrast to the RT domain, the C-terminal extension is an elongated helical bundle that contains several surface exposed, long loops. A search in the protein structure database using the software SSM (Krissinel & Henrick (2004) *Acta Cryst*. D60:2256-2268; Krissinel (2007) *Bioinformatics* 23:717-723) produced no structural homologues suggesting that the CTE domain of telomerase adopts a novel fold. Structural comparison of TERT with the HIV RT, the viral RNA polymerases and B-family DNA polymerases places the "thumb" domain of these enzymes and the CTE domain of TERT in the same spatial position with respect to the "fingers" and "palm" subdomains, indicating that the CTE domain of telomerase is the "thumb" domain of the enzyme, a finding that is in good agreement with previous biochemical studies (Hossain, et al. (2002) *J. Biol. Chem.* 277:36174-80).

TERT domain organization brings the TRBD and "thumb" domains, which constitute the terminal domains of the molecule, together, an arrangement that leads to the formation of a ring-like structure that is reminiscent of the shape of a donut (FIG. 10). Several lines of evidence indicate that the domain organization of the TERT structure presented herein is biologically relevant. First, the domains of four TERT monomers observed in two different crystal forms (two in each asymmetric unit) are organized the same (average RMSD=0.76 Å between all four monomers). Second, contacts between the N- and C-terminal domains of TERT are extensive (1677 Å$^2$) and largely hydrophobic in nature involving amino acid residues Tyr4, Lys76, Thr79, Glu84, Ser81, His87, Asn142, His144, Glu145, Tyr411, His415, Phe417, Trp420, Phe422, Ile426, Phe434, Thr487, Ser488, Phe489, and Arg592. This observation is in agreement with previous biochemical studies (Arai, et al. (2002) *J. Biol. Chem.* 277:8538-44). Third, TERT domain organization is similar to that of the polymerase domain (p66 minus the RNase H domain) of its closest homologue, HIV reverse transcriptase (Sarafianos, et al. (2002) supra), the viral RNA polymerases (Di Marco, et al. (2005) supra) and the B-family DNA polymerases and in particular RB69 (Wang, et al. (1997) supra). The arrangement of the TERT domains creates a hole in the interior of the particle that is ~26 Å wide and ~21 Å deep, sufficient to accommodate double-stranded nucleic acids approximately seven to eight bases long, which is in good agreement with existing biochemical data (Forstemann & Lingner (2005) *EMBO Rep.* 6:361-6; Hammond & Cech (1998) *Biochemistry* 37:5162-72).

The TERT Ring Binds Double-Stranded Nucleic Acid. To understand how the TERT ring associates with RNA/DNA to form a functional elongation complex, a double-stranded nucleic acid was modeled into the interior using the HIV reverse transcriptase—DNA complex (Sarafianos, et al. (2002) supra), TERT's closest structural homologue. The TERT-RNA/DNA model immediately showed some striking features that supported the model of TERT-nucleic acid associations. The hole of the TERT ring and where the nucleic acid heteroduplex was projected to bind was lined with several key signature motifs that are hallmarks of this family of polymerases and have been implicated in nucleic acid association, nucleotide binding and DNA synthesis. Moreover, the organization of these motifs resulted in the formation of a spiral in the interior of the ring that resembled the geometry of the backbone of double-stranded nucleic acid. Several of the motifs, identified as contact points with the DNA substrate, were formed partly by positively charged residues, the side chains of which extended toward the center of the ring and were poised for direct contact with the backbone of the DNA substrate. For example, the side chain, of the highly conserved K210 that forms part of helix α10, is within coordinating distance of the backbone of the modeled DNA thus providing the stability required for a functional telomerase enzyme. Helix α10 lies in the upper segment of the RT domain and faces the interior of the ring. The location and stabilization of this helix is heavily influenced by its extensive contacts with the IFD motif implicated in telomerase processivity (Lue, et al. (2003) *Mol. Cell. Biol.* 23:8440-9). Disruption of the IFD contacts with helix α10 through deletion or mutations of this motif would lead to displacement of helix α10 from its current location, which would in turn effect DNA-binding and telomerase function.

Structural elements of the "thumb" domain that localized to the interior of the ring also made several contacts with the modeled DNA substrate. In particular, the loop ("thumb" loop) that connects the "palm" to the "thumb" domain and constitutes an extension of the E motif also known as the "primer grip" region of telomerase, preserves to a remarkable degree, the geometry of the backbone of double stranded nucleic acid. The side chains of several lysines (e.g., Lys406, Lys416, Lys418) and asparagines (e.g., Asn423) that formed part of this loop extended toward the center of the TERT molecule and were within coordinating distance of the backbone of modeled double-stranded nucleic acid. Of particular interest was Lys406. This lysine was located in proximity of motif E and its side chain extended toward the nucleic acid heteroduplex and was poised for direct contacts with the backbone of the nucleotides located at the 3' end of the incoming DNA primer. It is therefore possible that the side chain of this lysine together with motif E help facilitate placement of the 3'-end of the incoming DNA substrate at the active site of the enzyme during telomere elongation. Sequence alignments of the "thumb" domain of TERTs from a wide spectrum of phylogenetic groups showed that the residues predicted to contact the DNA substrate are always polar (FIGS. 3A-3C). Another feature of the "thumb" domain that supported double-stranded nucleic acid binding was helix α19, a 3$^{10}$ helix ("thumb" 3$^{10}$ helix) that extended into the interior of the ring and appeared to dock itself into the minor groove of the modeled double-stranded nucleic acid thus facilitating RNA/DNA hybrid binding and stabilization. Deletion or mutation of the corresponding residues in both yeast and human TERT results in sever loss of TERT processivity clearly indicating the important role of this motif in TERT function (Hossain, et al. (2002) *J. Biol. Chem.* 277:36174-80; Huard, et al. (2003) *Nucleic Acids Res.* 31:4059-70; Banik, et al. *Mol. Cell. Biol.* 22:6234-46).

The Active Site of TERT and Nucleotide Binding. The *T. castaneum* TERT structure presented herein was crystallized in the absence of nucleotide substrates and magnesium, however, the location and organization of TERT's active site and nucleotide binding pocket was determined on the basis of existing biochemical data (Lingner, et al. (1997) supra) and structural comparison with the polymerase domain of its closest homologue, the HIV reverse transcriptase (Das, et al. (2007) *J. Mol. Biol.* 365:77-89). The TERT active site is composed of three invariant aspartic acids (Asp251, Asp343 and Asp344) that form part of motifs A and C, two short loops located on the "palm" subdomain, and adjacent to the "fingers" of TERT. Structural comparison of TERT with HIV reverse transcriptases, as well as RNA and DNA polymerases showed a high degree of similarity between the active sites of these families of proteins indicating that telomerase also employs a two-metal mechanism for catalysis. Alanine mutants of these TERT aspartic acids resulted in complete loss of TERT activity indicating the essential role of these residues in telomerase function (Lingner, et al. (1997) supra).

The telomerase nucleotide binding pocket is located at the interface of the "fingers" and "palm" subdomains of TERT and is composed of conserved residues that form motifs 1, 2, A, C, B' and D implicated in template and nucleotide binding (Bosoy & Lue (2001) *J. Biol. Chem.* 276:46305-12; Haering, et al. (2000) *Proc. Natl. Acad. Sci. USA* 97:6367-72). Structural comparisons of TERT with viral HIV reverse transcriptases bound to ATP (Das, et al. (2007) supra) supports nucleotide substrate in this location. Two highly conserved, surface-exposed residues Tyr256 and Val342 of motifs A and C, respectively, form a hydrophobic pocket adjacent to and above the three catalytic aspartates and could accommodate the base of the nucleotide substrate. Binding of the nucleotide in this oily pocket places the triphospate moiety in proximity of the active site of the enzyme for coordination with one of the $Mg^{2+}$ ions while it positions the ribose group within coordinating distance of an invariant glutamine (Gln308) that forms part of motif B' thought to be an important determinant of substrate specificity (Smith, et al. (2006) *J. Virol.* 80:7169-78). Protein contacts with the triphospate moiety of the nucleotide are mediated by motif D, a long loop, located beneath the active site of the enzyme. In particular, the side chain of the invariant Lys372 is within coordinating distance of the γ-phosphate of the nucleotide an interaction that most likely helps position and stabilize the triphosphate group during catalysis. The side chains of the highly conserved Lys189 and Arg194 of motifs 1 and 2, which together form a long β-hairpin that forms part of the "fingers" subdomain, are also within coordinating distance of the both the sugar and triphosphate moieties of the modeled nucleotide. Contacts with either or both the sugar moiety and the triphosphate of the nucleotide substrate would facilitate nucleotide binding and positioning for coordination to the 3'-end of the incoming DNA primer.

TRBD Facilitates Template Positioning at the Active Site of TERT. As with most DNA and RNA polymerases, nucleic acid synthesis by telomerase requires pairing of the templating region (usually seven to eight bases or more) of TER with the incoming DNA primer (Lee & Blackburn (1993) *Mol. Cell. Biol.* 13:6586-99). TRBD-RT domain organization forms a deep cavity on the surface of the protein that spans the entire width of the wall of the molecule, forming a gap that allows entry into the hole of the ring from its side. The arrangement of this cavity with respect to the central hole of the ring provides an elegant mechanism for placement of the RNA template, upon TERT-TER assembly, in the interior of the ring and where the enzyme's active site is located. Of particular significance is the arrangement of the β-hairpin that forms part of the T-motif. This hairpin extends from the RNA-binding pocket and makes extensive contacts with the "thumb" loop and motifs 1 and 2. Contacts between this hairpin and both the "fingers" and the "thumb" domains place the opening of the TRBD pocket that faces the interior of the ring in proximity to the active site of the enzyme. It is therefore likely that this β-hairpin acts as an allosteric effector switch that couples RNA-binding in the interior of the ring and placement of the RNA template at the active site of the enzyme. Placement of the template into the interior of the molecule would facilitate its pairing with the incoming DNA substrate, which together would form the RNA/DNA hybrid required for telomere elongation. RNA/DNA pairing is a prerequisite of telomere synthesis in that it brings the 3'-end of the incoming DNA primer in proximity to the active site of the enzyme for nucleotide addition while the RNA component of the heteroduplex provides the template for the faithful addition of identical repeats of DNA at the ends of chromosomes. Strikingly, modeling of the RNA/DNA heteroduplex in the interior of the TERT ring places the 5'-end of the RNA substrate at the entry of the RNA-binding pocket and where TERT is expected to associate with TER while it places the 3'-end of the incoming DNA primer at the active site of TERT providing a snapshot of the organization of a functional telomerase elongation complex.

Example 3

Structure of *T. castaneum* Telomerase Catalytic Subunit TERT Binding to RNA Template and Telomeric DNA Methods for Expressing and Purifying Proteins. Wild-type and mutant (Asp251Ala) *T. castaneum*, full length TERT proteins were overexpressed and purified as described herein with subtle modifications that increased protein yield. Specifically, the proteins were over-expressed in *E. coli* Rosetta (DE3) pLysS (Novagen) at 30° C. for 5 hours with slow shaking (shaker/incubator setting, 120 rpm). Stock protein (10 mg/ml) was dialyzed in 10 mM Tris-HCl, 100 mM KCl, 1 mM TCEP, pH 7.5 prior to crystallization trials.

Methods for Preparing *T. castaneum* Extracts and Isolating RNA. Twenty *T. castaneum* larvae or pupae were ground in liquid $N_2$, homogenized with 200 μl of extraction buffer (25 mM Tris-HCl, 5 mM β-mercaptoethanol (β-ME), 1 mM EGTA, 0.1 mM benzamidine, 200 mM KCl, 10% (w/v) glycerol, 10 mM imidazole and RNasin (PROMEGA, Madison, Wis.), pH 7.5) and placed on ice for 30 minutes. After the homogenate was centrifuged at 12,000 g at 4° C. for 20 minutes, the supernatant was collected, flush frozen in liquid nitrogen and stored at −80° C. before use. The total RNA was then extracted from the *T. castaneum* homogenate using the RNEASY Protect Mini Kit (QIAGEN, Valencia, Calif.).

Methods for In Vitro Reconstitution of *T. castaneum* Telomerase. The telomerase RNA of *T. castaneum* had not been previously identified. Therefore, total RNA was isolated from beetle larvae and used with the recombinant TERT to assemble the telomerase complex in vitro. Twenty μg of the his-tagged TERT (25 mM Tris, 200 mM KCl, 10% (w/v) glycerol, 5 mM β-ME and 10 mM imidazole, pH 7.5) was mixed with 50 µl of *T. castaneum* larvae total RNA and the two were incubated in *T. castaneum* lysate for two hours at room temperature in the presence of RNasin. The telomerase complex was then purified over a Ni-NTA column and tested for activity using a modified TRAP assay (Sasaki & Fujiwara (2000) *Eur. J. Biochem.* 267:3025-3031) as described herein.

Telomerase Repeat Amplification Protocol (TRAP) Assays. The activity of the in vitro reconstituted *T. castaneum* telomerase was tested using the following TRAP assay. The telomerase elongation step was carried out in a 50 µl reaction mixture composed of 20 mM Tris-HCl (pH 8.3), 7.5 mM MgCl$_2$, 63 mM KCl, 0.05% (w/v) TWEEN 20, 1 mM EGTA, 0.01% (w/v) BSA, 0.5 mM of each dNTP, 1 µM DNA primer (5'-aag ccg tcg agc aga gtc-3'; SEQ ID NO:17) (Tcas-TS)) and 4 µg of Ni-NTA purified, *T. castaneum* telomerase. After incubation at 30° C. for 60 minutes, each reaction mixture was phenol-chloroform extracted and precipitated with ethanol. Each sample was re-suspended in 50 µl of PCR reaction buffer (10 mM Tris/HCl (pH 8.0), 50 mM KCl, 2 mM MgCl$_2$, 100 µM dNTPs (dATP dTTP dGTP), 10 µM [$^{32}$P]dCTP (80 Ci per mmol), 1 µM Tcas-CX primer (5'-gtg tga cct gac ctg acc-3'; SEQ ID NO:18) and HOTSTARTAQ DNA polymerase (QIAGEN). The PCR products were resolved on Tris-borate-EDTA (TBE)-polyacrylamide gels. The presence of multiple telomeric repeats (TCAGG)$_n$ was also confirmed by subcloning and sequencing the TRAP products.

RNA-DNA Hairpins. The RNA-DNA hairpins tested for TERT binding, activity and subsequently for structural studies are shown in Table 6. All three hairpins contain the putative RNA-templating region (5'-rCrUrGrArCrCrU-3') (one and a half times the telomeric repeat of *T. castaneum*, TCAGG) and the complementary telomeric DNA sequence (5'-GTCAGGT-3'). The RNA-templating region and the DNA complement were connected for stability with an RNA-DNA linker (loop). The hairpins were designed to contain a 5'-RNA overhang so that the telomerase complex could be trapped in its replication state upon co-crystallization with the complementary non-hydrolysable nucleotide(s). The only difference between the three hairpins is the length of the linker.

TABLE 6

| Hairpin Sequence (5'->3') | SEQ ID NO: |
|---|---|
| 21 mer rCrUrGrArCrCrUrGrACTTCGGTCAGGT | 19 |
| 17 mer rCrUrGrArCrCrUrGTTCGCAGGT | 20 |
| 15 mer rCrUrGrArCrCrUUTTCGAGGT | 21 |

*Underlined sequences represent linker sequences. Bold sequences form the loop of the hairpin.

TERT, Reverse Transcriptase (RT) Assays. Standard reverse transcriptase assays were carried out using the recombinant *T. castaneum* TERT and the RNA-DNA hairpin (Table 6) to test TERT's ability to replicate the end of the DNA substrate that includes part of the RNA-DNA hairpin. RT assays were carried out in telomerase buffer (50 mM Tris-HCl, 100 mM KCl, 1.25 mM MgCl$_2$, 5 mM DTT, 5% (w/v) glycerol, pH 8 at room temperature), 100 µM dNTPs (dATP dTTP dGTP), 10 µM [$^{32}$P]dCTP (80 Ci per mmol), 5 µM RNA-DNA hairpin and 1 µM recombinant TERT. The samples were incubated for two hours at room temperature, then phenol/chloroform extracted and ethanol precipitated. The DNA pellet was re-suspended in a solution composed of 90% (w/v) formamide and 10% (w/v) glycerol and the sample was run on a 12% (w/v) polyacrylamide-7 M urea gel in 1×TBE at 220V for 70 minutes at 4° C.

Protein Crystallization and Data Collection. The binary complex was prepared by adding to the dialyzed protein 1.2 molar excess nucleic acid (RNA-DNA hairpin purchased from Integrated DNA Technologies), 5 mM dNTPαS (Jena Biosciences GmbH) and 5 mM MgCl$_2$. Crystals of the monoclinic space group P2$_1$ that diffracted to 2.7 Å resolution appeared in three days and grew to final size in two weeks. Crystals were grown by the vapor diffusion, sitting drop method by mixing one volume of the ternary complex with one volume of reservoir solution containing 0.1 M HEPES, (pH 7.5) and 12% 1,6-hexanediol or PEG 4K and 0.2 M KCl. Crystals were transferred into cryoprotectant solution that contained 0.1 M HEPES (pH 7.5), 15% (w/v) 1,6-hexanediol or PEG 4K, 15% (w/v) glycerol, 0.2 M KCl and 1 mM TCEP and were harvested by flash freezing in liquid nitrogen. Data were collected at the NSLS, beam line X25 and processed with MOSFILM as implemented in WEDGER-ELVES (Holton & Alber (2004) *Proc. Natl. Acad. Sci. USA* 101:1537-1542) (Table 7). There is one monomer in the asymmetric unit.

TABLE 7

| TERT Complex | |
|---|---|
| Data Collection | |
| Space group | P2$_1$ |
| Cell dimensions | |
| a, b, c (Å) | 77.2 52.8 101.6 |
| α, β, γ (°) | 90 101.9 90 |
| Resolution (Å) | 20-2.7 (2.85-2.70)* |
| R$_{sym}$ or R$_{merge}$ | 11.4 (45.8) |
| I/σI | 7.9 (2.3) |
| Completeness (%) | 93.7 (96.1) |
| Redundancy | 2.8 (2.5) |
| Refinement | |
| Resolution (Å) | 20-2.7 |
| No. Reflections | 19815 |
| R$_{work}$/R$_{free}$ | 24.2/28.7 |
| Number of atoms | 4982 |
| Protein | 4982 |
| Ligand/Ion | 496/1 |
| Water | 54 |
| B-factors | |
| Protein | 45 |
| Ligand/Ion | 37 |
| Water | 21 |
| R.m.s. Deviations | |
| Bond lengths (Å) | 0.006 |
| Bond angles (°) | 0.887 |

*Number of crystals used - one.
*Values in parentheses are for highest-resolution shell.

Structure Determination and Refinement. Phases where calculated by molecular replacement (MR) using PHASER (Potterton, et al. (2003) *Acta Crystallogr D Biol Crystallogr* 59:1131-1137) as implemented in CCP4 suit of programs using the substrate-free TERT structure described herein as a search model. Maps calculated after one cycle of refinement by CNS-SOLVE revealed clear 2fo-fc density for all 596 residues of TERT and fo-fc density for the nucleic acid substrate at 3.0 σ contour level. Model building was carried out in COOT (Emsley & Cowtan (2004) *Acta Crystallogr D Biol Crystallogr* 60:2126-2132) and the model was refined using both CNS-SOLVE (Brunger, et al. (1998) *Acta Crystallogr. D Biol. Crystallogr.* 54:905-921) and REFMAC5 (Murshudov, et al. (1997) *Acta Crystallogr. D Biol. Crystallogr.* 53:240-255). The last cycles of refinement were carried out with TLS restraints as implemented in REFMAC5. The structure was refined to good stereochemistry with 84.3, 14.3 and 1.4 of the residues in the most favorable, additional allowed and generously allowed of the Ramachandran plot, respectively.

TERT Structure Overview. The full length (FIG. 1B), active, *T. castaneum*, TERT was co-crystallized with an RNA-DNA hairpin containing the putative RNA templating region (5'-rCrUrGrArCrCrU-3') and the complementary telomeric DNA (5'-GTCAGGT-3') joined together with a short RNA-DNA linker (Table 6). It is worth noting that the *T. castaneum* TERT lacks the TEN domain, required for activity and processivity in several eukaryotic telomerase genes, including human (Wyatt, et al. (2009) *PLoS One* 4:e7176) and *Tetrahymena thermophila* (Zaug, et al. (2008) *Nat. Struct. Mol. Biol.* 15:870-872; Finger & Bryan (2008) *Nucleic Acids Res.* 36:1260-1272). The absence of the TEN domain from *T. castaneum* could explain the reduced activity observed for this enzyme when compared to those containing this domain. The RNA component of *T. castaneum* telomerase has not been previously identified. Therefore, the following information was used to predict its templating region: The RNA templating region of telomerase is usually one and a half telomeric repeats (Lee & Blackburn (1993) *Mol. Cell. Biol.* 13: 6586-6599; Lingner, et al. (1994) *Genes Dev.* 8: 1984-1998; Shippen-Lentz & Blackburn (1990) *Science* 247: 546-552) and this sequence is known for many organisms (telomerase database). For example the mammalian telomerase templating region is "CUAACCCU" and the telomeric repeat is "TTAGGG". The telomeric repeat for *T. castaneum* is "TCAGG"(Osanai, et al. (2006) *Gene* 376:281-89; Richards, et al. (2008) *Nature* 452:949-955). The RNA-DNA hairpin was designed to contain a three-nucleotide overhang at the 5'-end of the RNA template, so that the enzyme could be trapped in its catalytic state upon co-crystallization of the protein-nucleic acid assembly with $Mg^{++}$ ions and non-hydrolysable nucleotides. In an effort to identify a hairpin suitable for crystallographic studies, a number of RNA-DNA hairpins were screened (15 mer, 18 mer and 21 mer; Table 6) where the templating region and the complementary DNA sequence were kept the same but the length of the linker was changed. Although, all three hairpins tested had the same binding affinity for TERT and reverse transcriptase activity, only the 21 mer was amenable to crystallographic studies. It was noted that in the structure, the hairpin linker extends out of the TERT ring and is only involved in crystal contacts with adjacent molecules. The crystals were also grown in the presence of the slowly hydrolysable nucleotide analogues dNTPaS and $Mg^{++}$ ions.

The structure was solved at 2.7 Å resolution using the method of molecular replacement with the substrate-free TERT described herein as a search model. All of the TERT molecule and the RNA-DNA hybrid were interpretable in electron density maps. Unexpectedly, there was extra density for three nucleotides at the 3'-end of the telomeric DNA, indicating that TERT had extended the 3'-end of the DNA substrate in the crystallization drop. There was no evidence for nucleotide at the active site of the enzyme, which was partially occupied by the nucleotide located at the 3'-end of the DNA substrate. Several lines of evidence indicate that the association of the RNA templating region and the DNA substrate with TERT in the structure presented here are biologically relevant. First, TERT is an active polymerase in the presence of the nucleic acid substrate used in this study both by standard reverse transcriptase assays and in the crystallization drop. Second, the RNA template makes contacts with conserved motifs that are hallmarks of this family of enzymes. Third, contacts between TERT and the RNA template position the solvent accessible bases adjacent to and above the active site of the enzyme for nucleotide binding thus facilitating selectivity. Moreover, TERT-RNA associations position the 5'-end of the RNA-template at the entry of the TRBD RNA-binding pocket and where the template boundary element located upstream of the RNA-template in many organisms is thought to bind. Fourth, interactions between the DNA substrate and the primer grip region (a characteristic shared among telomerase and HIV RTs) place the 3'-end of the DNA substrate at the active site of the enzyme where it is accessible for nucleotide addition. Fifth, TERT-nucleic acid associations are strikingly similar to those observed of HIV reverse transcriptase, TERT's closest structural homologue.

Figure 1C:
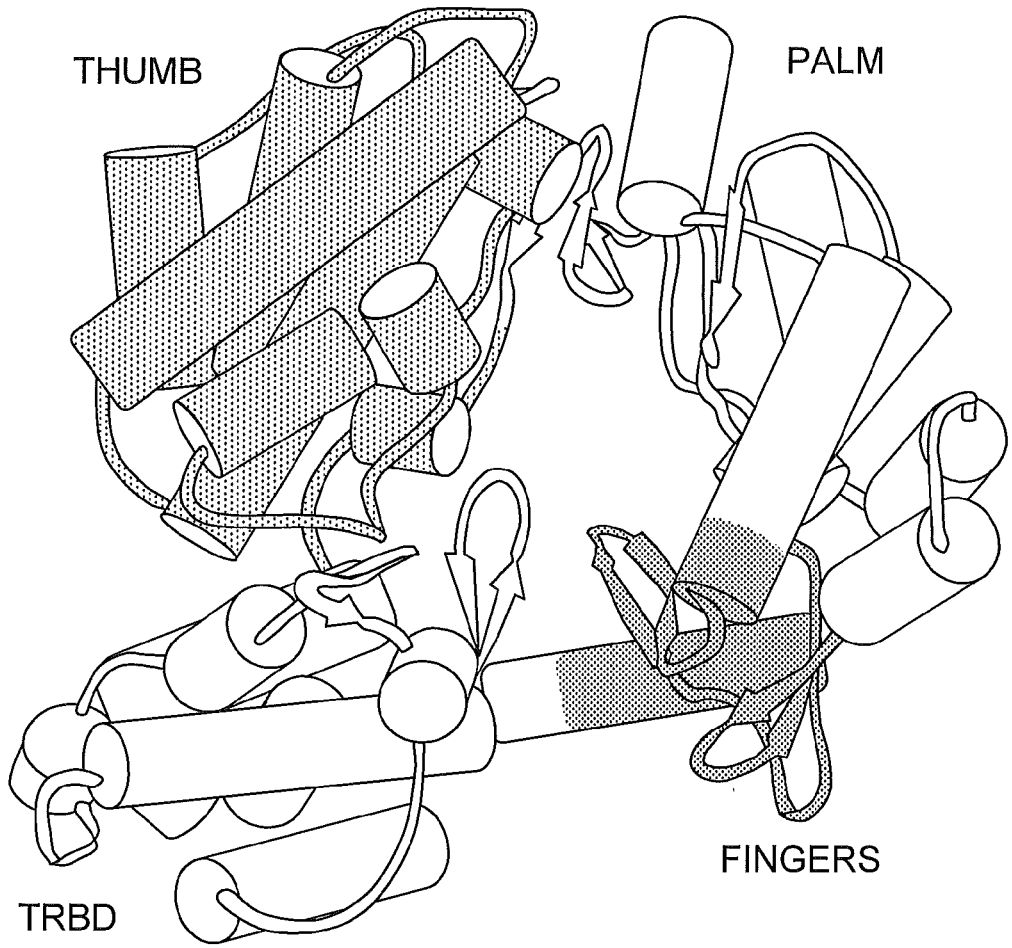
FIG. 1C shows TERT domain organization with the RNA-binding domain (TRBD), the reverse transcriptase domain composed of the "fingers" and "palm" subdomains, and the "thumb" domain depicted.

The four major TERT domains: the RNA-binding domain (TRBD); the fingers domain, implicated in nucleotide binding and processivity (Bosoy & Lue (2001) *J. Biol. Chem.* 276:46305-46312); the palm domain, which contains the active site of the enzyme; and the thumb domain, implicated in DNA binding and processivity (Hossain, et al. (2002) *J. Biol. Chem.* 277:36174-80), were organized into a ring configuration similar to that observed for the substrate-free enzyme described herein (FIG. 1C). The arrangement of the TERT domains created a highly positively charged cavity in the interior of the TERT ring, which was 22 Å wide and 21 Å deep and could accommodate seven bases of double stranded nucleic acid. Within this cavity binds one molecule of the RNA-DNA hybrid, which assembles together, via Watson-Crick base pairing into a helical structure similar to both the DNA-DNA and RNA-DNA structure bound to HIV reverse transcriptase (Huang, et al. (1998) *Science* 282:1669-75; Sarafianos, et al. (2001) *EMBO J.* 20:1449-61).

Figure 5:
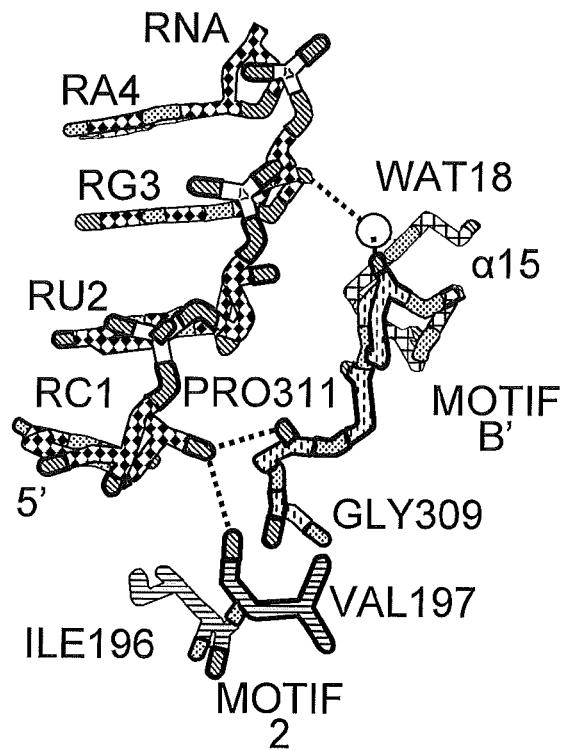
FIG. 5 depicts TERT RNA template associations. The nucleotide located at the 5'-end of the RNA template (rC1) is coordinated by Ile196 and Val197 of motif 2 and Gly309 of motif B'. rU2 interacts with Pro311 of motif B' and rG3 coordinates the backbone of helix α15 via a water molecule (Wat18).

TERT Nucleic Acid Associations. Structure analysis indicated that interactions between the protein and the RNA templating region were mediated by the fingers, the palm and thumb domains. The 5'-end RNA cytosine (rC1) and uracil (rU2) were located at the interface of the fingers and palm domains and were involved in a network of interactions with conserved residues (FIG. 3) of motifs 2 and B' both of which are located in proximity of the active site of the enzyme. In particular, the 2'-OH and the base carbonyl of rC1 is within hydrogen bonding distance of the backbone carbonyls of Val197 of motif 2 and Gly309 of motif B' while the pyrimidine base sits over the otherwise solvent exposed, hydrophobic side chain of the conserved Ile196 that also forms part of motif 2 (FIG. 5). Contacts between rU2 and the protein are mediated by the short aliphatic side chain of Pro311 and the ribose group (FIG. 5). Interactions between rC1 and rU2 with motifs 2 and B' place the cytosine base in proximity of the active site of the enzyme, where it is well-positioned for Watson-Crick base-pairing with the incoming nucleotide substrate.

Stabilization and placement of the 5'-end bases of the templating region above the active site of the enzyme was in large part mediated by the interactions of the remaining five ribonucleotides with the incoming DNA primer. Limited contacts between this part of the RNA and the protein were mediated via a water molecule (Wat18) which coordinates the 2'-OH of guanosine (rG3) with the backbone of helix α15 (FIG. 5). Notably, the structural organization of helix α15 was influenced by the IFD motif, a long insertion, composed of two helices (α13 and α14), between motifs A and B', which explains why mutations in this motif lead to loss of telomerase function (Lue, et al. (2003) *Mol. Cell. Biol.* 23:8440-49).

Figure 6:
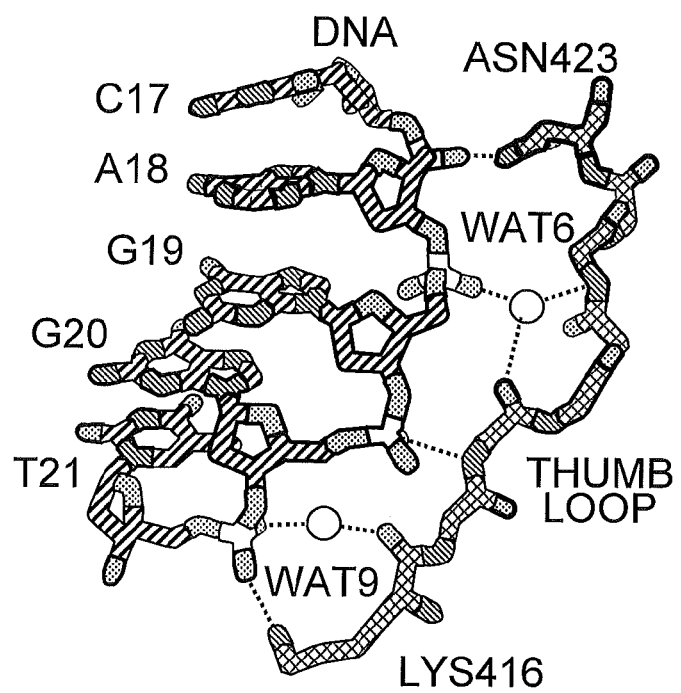
FIG. 6 depicts TERT telomeric DNA associations. Interactions between the thumb loop and the DNA are mostly backbone and solvent mediated. Also, the side chains of Lys416 and Asn423 that form part of the thumb loop extend toward the center of the ring and coordinate the DNA backbone.
Figure 7:
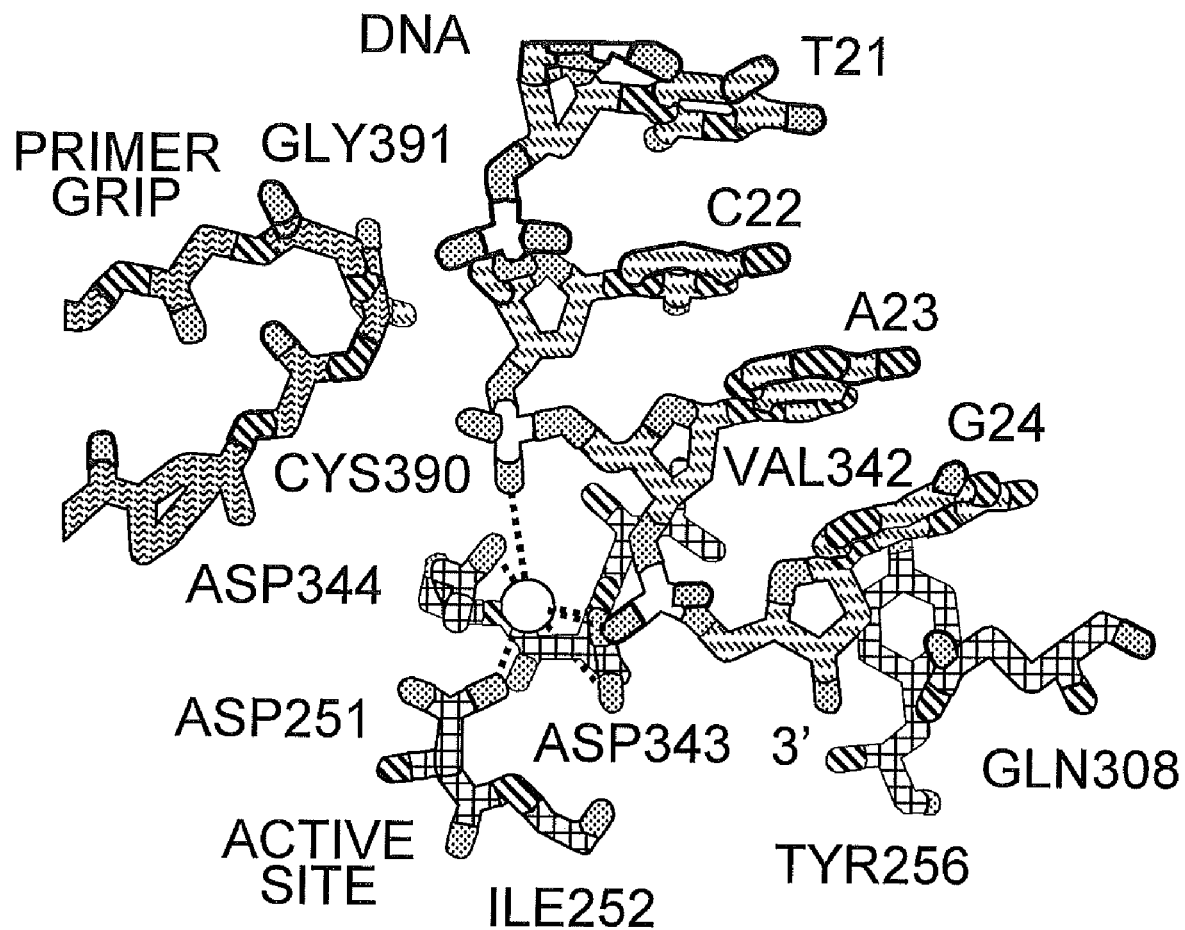
FIG. 7 depicts DNA interactions with the primer grip region and the active site. Shown is a stereo view of the DNA interactions with motif E and the active site residues. The tip of the primer grip region (loop shown on left), formed by the backbone of residues Cys390 and Gly391 abuts the ribose group of C22 and this interaction guides the 3'-end of the DNA at the active site of the enzyme for nucleotide addition. The active site bound magnesium ion (sphere) coordinates the DNA backbone formed by the last two nucleotides. The nucleotide binding pocket of TERT, which is partially occupied by the last DNA nucleotide, is in part formed by the highly conserved residue Val342 and the invariant Tyr256 and Gly308.

Contacts between TERT and the DNA substrate were mediated in large part via backbone interactions with the thumb loop and helix. The thumb helix, as described herein, sits in the minor groove of the RNA-DNA heteroduplex, making extensive contacts with the phosphodiester backbone and the ribose groups of the RNA-DNA hybrid. The mode of action of the thumb helix of telomerase appears to be similar to that proposed for the equivalent helix (helix H) of retroviral reverse transcriptases (Jacobo-Molina, et al. (1993) *Proc. Natl. Acad. Sci. USA* 90:6320-24; Kohlstaedt, et al. (1992) *Science* 256:1783-1790). Another conserved element of the thumb domain, known as the thumb loop, runs almost parallel to the curvature of the DNA primer and the two are involved in a network of backbone and solvent mediated interactions (FIG. 6). Interactions between the DNA and the thumb loop included the side chains of Lys416 and Asn423, both of which extended toward the center of the ring and were within hydrogen bonding distance of the DNA backbone. Contacts between the thumb domain and the DNA position the nucleotides located at its 3'-end within coordinating distance of the primer grip region (motif E), a short, rigid loop located at the interface of the palm and thumb domains, and in proximity of the active site of the enzyme (FIG. 7). The backbone of the tip of this loop formed by the conserved residues Cys390 and Gly391 abuts the ribose group of C22 and this interaction guides the 3'-end DNA nucleotides toward the active site of the enzyme (FIG. 7). The active site of the enzyme, and where the incoming nucleotide is projected to bind, is partially occupied by the nucleotide (G24) located at the 3'-end of the DNA (FIG. 7). The ribose group, and to a certain extend the guanosine base of G24, which makes Watson-Crick pairing interactions with the rC1 located at the 5'-end of the RNA template, sit in a well-defined hydrophobic pocket formed by the side chains of the invariant Tyr256, Gln308 and conserved Val342 of motifs A, B' and C respectively, while the α-phosphate is coordinated by the magnesium ion occupying the active site aspartates (FIG. 7). The important role of Val342 in telomerase selectivity has been shown for the human telomerase holoenzyme (Drosopoulos & Prasad (2007) *Nucleic Acids Res.* 35:1155-1168).

TERT Domain Rearrangements Upon Nucleic Acid Binding. Comparisons of the nucleic acid bound and substrate-free TERT structures indicate that TERT nucleic acid associations induce small rigid-body changes in orientation between subunits of the enzyme that lead to a 3.5 Å decrease of the diameter of the interior cavity of the ring. The decrease in the diameter of the central cavity arises from a 6° inward rotation together with a 3.5 Å translation, of the thumb domain with respect to the fingers and palm domains. Translation of the thumb domain toward the center of the ring is accompanied by the TRBD, which is also shifted 3.5 Å toward the finger domain creating a more narrow RNA-binding pocket than the substrate-free enzyme. The role of this subtle structural rearrangement may have implications for TERT association with the full-length RNA, TER.

Common Aspects of Substrate Binding Between TERT and HIV RTs. It has been postulated that telomerase uses a mechanism of DNA replication that resembles that of other retroviral reverse transcriptases, a suggestion supported by the structure of the TERT-nucleic acid complex presented here. Structural comparison of the RNA-DNA bound TERT and HIV RT (PDB ID: 1HYS36) shows a striking similarity in the overall domain organization and nucleic acid binding between the two structures. Like HIV RTs, telomerase-dependent telomere replication requires pairing of the templating region with the incoming DNA primer and placement of the 3'-end of the DNA into the enzyme's active site for nucleotide addition. Moreover, TERT- or HIV RT-nucleic acid associations are accompanied by domain rearrangements that facilitate the formation of a tight, catalytic, protein nucleic acid assembly and positioning of the DNA 3'-end at the active site of the enzyme for catalysis (Kohlstaedt, et al. (1992) supra; Rodgers, et al. (1995) *Proc. Natl. Acad. Sci. USA* 92:1222-1226; Steitz (1997) *Harvey Lect.* 93:75-93). Contacts between the protein and the RNA templating region are specific and involve telomerase key signature motifs (motif 2 and B' of the fingers and palm domains, respectively) that are hallmarks of these families of enzymes and are required for positioning of the solvent accessible bases of the RNA template in proximity of the active site for nucleotide binding and selectivity. Contacts between the protein and the DNA substrate are mediated by the thumb domain and despite the lack of sequence homology in this region between the two families of enzymes, the mode of action of the thumb helix of telomerase is similar to that proposed for helix H of HIV RTs (Jacobo-Molina, et al. (1993) supra; Kohlstaedt, et al. (1992) supra; Beese, et al. (1993) *Science* 260: 352-355). Placement of the DNA 3'-end at the active site of the enzyme is further facilitated by the primer grip region another highly conserved motif between TERT and HIV RTs44 (FIG. 7).

Although the enzyme was not trapped in its catalytic state, the partially occupied active site of the enzyme, formed by a number of invariant (Asp251, Tyr256, Gln308, Asp343, Asp344) or highly conserved residues (Val342), by the nucleotide G24 located at the 3'-end of the DNA (FIG. 7) suggests the mechanism of nucleotide binding and selectivity of telomerase during the replication process. In a similar manner, the invariant Tyr256 and Gln308 are also present in HIV RTs where, like in TERT, they are involved in nucleotide binding and selectivity through positioning for interactions with the templating region (Huang, et al. (1998) supra; Cases-Gonzalez, et al. (2000) *J. Biol. Chem.* 275:19759-19767), further supporting common mechanistic aspects of DNA replication between these families of enzymes.

TERT Rigid Conformational Changes and Function. Domain re-organization, upon nucleic acid binding, are a common feature of RNA-, DNA-polymerases and retroviral reverse transcriptases, and are geared toward the formation of a tight, catalytic protein nucleic acid assembly and positioning of the DNA 3'-end at the active site of the enzyme for catalysis (Kohlstaedt, et al. (1992) supra; Rodgers, et al. (1995) supra; Steitz (1997) supra). Unlike HIV RTs, telomerase appears to exist, at least in the absence of the full-length integral RNA component, in a closed ring configuration, an arrangement mediated by extensive contacts between the TRBD and the thumb domains. Comparison of the nucleic acid bound and substrate-free TERT structures indicate that TERT nucleic acid associations induce subtle, rigid-body changes in orientation between subunits of the enzyme that lead to a 3.5 Å decrease of the diameter of the interior cavity of the ring. These observations were unexpected because in most polymerases, including the HIV RT, the fingers and thumb domains undergo significant conformational changes required for substrate binding and function (Steitz (1997) supra; Ding, et al. (1998) *J. Mol. Biol.* 284:1095-1111; Steitz (1999) *J. Biol. Chem.* 274:17395-98). For example, the fingers domain, which is known to bind and position the nucleotide at the active site of the enzyme, undergoes significant conformational changes referred to as the open and closed states (Ding, et al. (1998) supra). It is therefore possible that the interactions between the TRBD and the thumb domains lock the fingers domain in place, thus preventing the conformational rearrangements observed in other polymerases, which would indicate the possibility of a preformed active site. A preformed active site has been observed for the Hepatitis C viral RNA polymerase (NS5B)(Bressanelli, et al.

(2002) *J. Virol.* 76:3482-92), a close structural homologue of TERT but also the Y-family DNA polymerases (Ling, et al. (2001) *Cell* 107:91-102). Another possibility is that the substrate-free TERT enzyme was trapped in the closed fingers conformation. Assuming the later is true, significant movement of the fingers domain of TERT would most likely require that the TRBD and the thumb domains are splayed apart. Contacts between the TRBD and the thumb domain are extensive and would require significant energy to force them apart. This could be accomplished by accessory proteins that possibly act in a similar manner to that of the sliding clamp loader of DNA polymerases (Jeruzalmi, et al. (2002) *Curr. Opin. Struct. Biol.* 12:217-224).

Repeat Addition Processivity. Telomerase, unlike most polymerases, has the ability to add multiple identical repeats of DNA to the ends of chromosomes, known as repeat addition processivity. This unique characteristic of telomerase has been attributed in part to the association of the N-terminal portion of TERT with TER and the telomeric overhang as well as the IFD motif (Lue, et al. (2003) supra). The TEN domain, present in several organisms, and its weak interaction with the DNA substrate is thought to be a determinant of repeat addition processivity (Wyatt, et al. (2007) *Mol. Cell. Biol.* 27:3226-40; Moriarty, et al. (2004) *Mol. Cell. Biol.* 24:3720-33), while most recently the TRBD and its stable association with TER has also been shown to be involved in this process (see data presented herein). In the complex presented here, the RNA does not directly engage the RNA-binding pocket of TRBD. The structure shows that TERT-RNA contacts position the 5'-end of the templating region at the entry of the RNA-binding pocket of TRBD. This arrangement would place the template boundary element (Chen &7 Greider (2003) *Genes Dev.* 17:2747-2752; Lai, et al. (2002) *Genes Dev.* 16:415-20; Tzfati, et al. (2000) *Science* 288:863-867) present in most organisms or the short oligonucleotide overhang of rodent TER51 within the RNA binding pocket of TRBD. The stable association of TER with the TRBD would force the enzyme to stall when reaching the nucleotide located at the 5'-end of the RNA template thus preventing replication beyond this point. Stalling of the enzyme for extended periods would lead to destabilization and dissociation of the RNA-DNA heteroduplex and initiation of another round of telomere replication.

Collectively, the data presented here supports common mechanistic aspects of substrate binding and DNA replication between telomerase and HIV reverse transcriptases, indicating an evolutionary link between these families of enzymes. It also provides novel insights into the basic mechanisms of telomere replication and length homeostasis by telomerase. Moreover, the structure presented here provides a detailed picture of the physical contacts between TERT and its nucleic acid substrates, information of use in the design of small molecule inhibitors of telomerase having therapeutic value in the treatment of cancer and other diseases associated with cellular aging.

Example 4

Modulators of Telomerase Activity

The X-ray crystal structure (complex of TERT with RNA-DNA, nucleotides and magnesium ions) showed that the organization of the fingers and palm domains between the substrate-free and substrate-bound TERT molecules is highly similar, indicating that like the Hepatitis C viral RNA polymerase (NS5B), telomerase has a preformed active site. This observation is surprising since in most polymerases, including the HIV reverse transcriptase, the fingers domain undergoes significant conformational changes referred to as the open and closed states. In HIV RTs, conformational rearrangements of the fingers domain with respect to the palm domain are essential for nucleotide binding and positioning at the active site of the enzyme and their absence from telomerase suggests possible mechanistic differences in nucleotide binding and selectivity between these families of enzymes.

The organization of the fingers and palm domains of TERT creates a deep, well-defined narrow mostly hydrophobic Fingers-Palm pocket (FP-pocket; residues Y170, F193, A195, D254, W302, H304, L307, Q308) that opens into the interior cavity of the TERT ring and is solvent accessible. Moreover, the entry of this pocket is located in close proximity of the active site (D251, D343 and D344) of the enzyme, which is absolutely essential for telomerase function. Alanine mutants of any of the above three invariant aspartates that form the active site of the enzyme completely abolishes telomerase activity.

Based on the fact that the FP-pocket is a stable, well-defined, solvent accessible cavity and is located in close proximity of the active site of the enzyme indicates that it is likely a useful target for the identification of small molecule inhibitors-activators that modulate telomerase activity. Based on the structure of the FP-pocket, it is expected that inhibitors will occlude the active site of telomerase thus interfering with nucleotide association and therefore telomere replication. On the other hand, activators are expected to be in close proximity to the active site of the enzyme without occluding the active site of the enzyme. These compounds could therefore be involved in favorable interactions with the incoming nucleotide substrate producing a tight and stable catalytic active complex thus increasing telomerase activity.

Example 5

Fluorescence Polarization Binding Assay

The TERT protein was expressed and purified as described herein. Protein was concentrated to 4.72 mg ml-1 using an AMICON 30K cutoff filter (Millipore) and stored at −80° C. for binding assays.

For the binding assay, TERT protein was diluted to a 500 nM concentration in a solution of 50 mM Tris-HCl, pH 7.5, 200 mM KCl, and 20% glycerol. A 1.2-fold molar excess of the Chim21m RNA-DNA hybrid (Integrated DNA Technologies), containing the template for telomere extension (5'-rCrUrG rArCrC rUrGrA rCTT CGG TCA GGT-3'; SEQ ID NO:19), was then added to these samples and kept on ice. The cyanine 5-dCTP (Perkin Elmer) for the binding study was made up to a 20 nM concentration in sterile, RNase, DNase free water with 40 nM $MgCl_2$.

Compound screens were carried out as 30.5 µl reactions in a 384-well, round bottom plate (Thermo). Fifteen µl of TERT-Chim21m complex was first added to each well. Then 0.5 µl of library compound (ChemBridge) was added to this solution. Finally, 15 µl of the nucleotide-MgCl2 sample was added, and the solution mixed to provide final concentrations of 250 nM protein-nucleic acid, 10 nM cyanine 5-dCTP, and 20 nM $MgCl_2$. Final compound concentrations were 50 µM and 5 µM. All additions were completed using a Janus 96/384 Modular Dispensing Tool (Perkin Elmer), performed in triplicate, and equilibrated for 40 minutes. Fluorescence polarization was measured at $\lambda_{ex}$=620 nm and $\lambda_{em}$=688 nm on an EnVision Xcite Multilabel plate reader (Perkin Elmer). Polarization was calculated using the standard equation: P=(V−H)/

Example 6

Efficacy of Telomerase Inhibitors

Novel telomerase inhibitors of the instant invention can be analyzed in a variety of systems. The compounds can be assessed in defined well-known model systems used to assess cellular permeability, toxicity, and pharmacodynamic effects. These assays include both cell-based and animal based assays.

Cell-Based Assay. Cells from a P388 cell line (CellGate, Inc., Sunnyvale, Calif.) or human malignant melanoma cell line SK-MEL-2 are grown in RPMI 1640 cell medium containing fetal calf serum (10%), L-glutamine, penicillin, streptomycin and are split twice weekly. All compounds are first diluted with DMSO. Later serial dilutions are done with a phosphate-buffered saline solution. All dilutions are done in glass vials and the final DMSO concentration is generally below 0.5% by volume. Final two-fold dilutions are done in a 96-well plate using cell media so that each well contains 50 µL. All compounds are assayed over multiple concentrations. Cell concentration is measured using a hemacytometer and the final cell concentration is adjusted to about $1 \times 10^4$ cells/mL with cell medium. The resulting solution of cells (50 µL) is then added to each well and the plates are incubated for 5 days in a 37° C., 5% $CO_2$, humidified incubator. MTT solution (3-[4,5-dimethylthiazol-2-yl]-2,5-diphenyltetrazolium bromide, 10 µL) is then added to each well and the plates are re-incubated under identical conditions for 2 hours. To each well is then added acidified isopropanol (150 µL of i-PrOH solution containing 0.05 N HCl) and mixed thoroughly. The plates are then scanned at 595 nm and the absorbances are read (Wallac Victor 1420 Multilabel Counter). The resulting data is then analyzed to determine an $ED_{50}$ value. Compounds that kill cancer cells, but fail to kill normal cells, find application in the prevention or treatment of cancer.

Mouse Ovarian Carcinoma Zenograft Model. Compounds of the invention are evaluated in an ovarian carcinoma xenograft model of cancer, based on that described by Davis, et al. ((1993) *Cancer Research* 53:2087-2091). This model, in brief, involves inoculating female nu/nu mice with $1 \times 10^9$ OVCAR3-icr cells into the peritoneal cavity. One or more test compounds are administered, e.g., prior to or after tumor cell injection, by the oral route as a suspension in 1% methyl cellulose or intraperitoneally as a suspension in phosphate-buffered saline in 0.01% TWEEN-20.

At the conclusion of the experiment (4-5 weeks) the number of peritoneal cells are counted and any solid tumor deposits weighed. In some experiments tumor development is monitored by measurement of tumor specific antigens.

Rat Mammary Carcinoma Model. Compounds of the invention are evaluated in a HOSP.1 rat mammary carcinoma model of cancer (Eccles, et al. (1995) *Cancer Res.* 56:2815-2822). This model involves the intravenous inoculation of $2 \times 10^4$ tumor cells into the jugular vein of female CBH/cbi rats. One or more test compounds are administered, e.g., prior to or after tumor cell injection, by the oral route as a suspension in 1% methyl cellulose or intraperitoneally as a suspension in phosphate-buffered saline and 0.01% TWEEN-20. At the conclusion of the experiment (4-5 weeks) the animals are killed, the lungs are removed and individual tumors counted after 20 hours fixation in Methacarn.

Mouse B16 Melanoma Model. The anti-metastatic potential of compounds of the invention is evaluated in a B16 melanoma model in C57BL/6. Mice are injected intravenously with $2 \times 10^5$ B16/F10 murine tumor cells harvested from in vitro cultures. Inhibitors are administered by the oral route as a suspension in 1% methyl cellulose or intraperitoneally as a suspension in phosphate-buffered saline pH 7.2 and 0.01% TWEEN-20. Mice are killed 14 days after cell inoculation and the lungs removed and weighed prior to fixing in Bouin's solution. The number of colonies present on the surface of each set of lungs is then counted.

---

What is claimed is:

1. A method for identifying a compound which modulates the activity of telomerase comprising (a) using a computer program to generate a three-dimensional structure of the Fingers-Palm pocket of a telomerase protein of SEQ ID NO:9 in complex with an RNA template and complementary telomeric DNA, wherein said Fingers-Palm pocket consists of amino acid residues 170, 193, 195, 254, 302, 304, 307 and 308 of SEQ ID NO:9 and said three-dimensional structure has a space group of $P2_1$ and unit cell parameters of a=77.2 Å, b=52.8 Å, c~101.6 Å, α=90 Å, β=101.9 Å, and γ=90 Å at a resolution of 2.7 Å;

(b) designing or screening for a compound that binds to said pocket; and (c) testing the compound designed or screened for in (b) by in vitro or in vivo assay for its ability to modulate the activity of telomerase, thereby identifying a compound that modulates the activity of telomerase.

* * * * *